US009029149B2

(12) United States Patent
Nain

(10) Patent No.: US 9,029,149 B2
(45) Date of Patent: May 12, 2015

(54) METHODS, APPARATUS, AND SYSTEMS FOR FABRICATION OF POLYMERIC NANO- AND MICRO-FIBERS IN ALIGNED CONFIGURATIONS

(75) Inventor: Amrinder Singh Nain, Christiansburg, VA (US)

(73) Assignee: Carnegie Mellon University, Pittsburgh, PA (US)

( * ) Notice: Subject to any disclaimer, the term of this patent is extended or adjusted under 35 U.S.C. 154(b) by 1013 days.

(21) Appl. No.: 12/512,893

(22) Filed: Jul. 30, 2009

(65) Prior Publication Data

US 2010/0028999 A1    Feb. 4, 2010

Related U.S. Application Data

(60) Provisional application No. 61/137,498, filed on Jul. 31, 2008, provisional application No. 61/223,746, filed on Jul. 8, 2009.

(51) Int. Cl.
| | |
|---|---|
| *C12N 5/071* | (2010.01) |
| *B28B 21/52* | (2006.01) |
| *B32B 5/00* | (2006.01) |
| *D01F 6/22* | (2006.01) |
| *A61L 27/38* | (2006.01) |
| *B81C 99/00* | (2010.01) |
| *C12N 5/00* | (2006.01) |
| *D01D 5/04* | (2006.01) |

(52) U.S. Cl.
CPC ............... *D01F 6/22* (2013.01); *A61L 27/3804* (2013.01); *A61L 27/3895* (2013.01); *B81C 99/003* (2013.01); *C12N 5/0068* (2013.01); *C12N 2533/30* (2013.01); *D01D 5/04* (2013.01)

(58) Field of Classification Search
CPC ........... A61L 27/3804; C12N 2533/30; C12N 5/0068; D01D 5/04; D01F 6/22
USPC ........................... 435/398, 396; 364/145, 164
See application file for complete search history.

(56) References Cited

U.S. PATENT DOCUMENTS

| | | | | |
|---|---|---|---|---|
| 6,872,311 | B2 * | 3/2005 | Koslow ..................... | 210/502.1 |
| 7,235,295 | B2 * | 6/2007 | Laurencin et al. ............. | 428/364 |
| 7,815,855 | B2 * | 10/2010 | Harttig ........................... | 422/422 |
| 2003/0146537 | A1 | 8/2003 | James et al. | |
| 2003/0201579 | A1 | 10/2003 | Gordon et al. | |

FOREIGN PATENT DOCUMENTS

WO        WO 9927167 A1 *  6/1999  ................. D01F 4/00

OTHER PUBLICATIONS

Common Solvents and Non-solvents of Polystyrene. Adapted from Brandrup and Immergut. eds. 1975 Polymer Handbook 2$^{nd}$ Ed. p. 1 (downloaded on May 29, 2012 from www.bangslabs.com/sites/default/files/bangs/docs/pdf/Solvent_Listing.pdf).*
Nain et al. 2007. Dry Spinning Polymeric Nano/microfiber Arrays using Glass Micropipettes with Controlled Porosities and Fiber Diameters. Proceedings of the 7th IEEE International Conference on Nanotechnology. Aug. 2-5, 2007, Hong Kong. p. 728-732.*
Calvert et al. Direct Spinning and Fabrication: The Robospider . National Textile Center Research Briefs: Jun. 2007 p. 1-2.*
Calvert et al. NTC Project No: F05-MD09. Direct Spinning and Fabrication: the Robospider. National Textile Center Annual Report: Nov. 2006. p. 1-10.*
Thapa et al., Nano-structured polymers enhance bladder smooth muscle cell function, Biomaterials, 2003, pp. 2915-2926, vol. 24.
Wang et al., Scaling Laws in Electrospinning of Polystyrene Solutions, Macromolecules, 2006, pp. 7662-7672, vol. 39.
Wnek et al., Electrospinning of Nanofiber Fibrinogen Structures, Nano Letters, 2003, pp. 213-216, vol. 3, No. 2.
Xu et al., Microfabricated Quill-Type Surface Patterning Tools for the Creation of Biological Micro/Nano Arrays, Biomedical Microdevices, 2004, pp. 117-123, vol. 6, No. 2.
Yaffe et al., Serial passaging and differentiation of myogenic cells isolated from dystrophic mouse muscle, Nature, Dec. 1977, pp. 725-727, vol. 270.
Zhang et al., Recent development of polymer nanofibers for biomedical and biotechnological applications, Journal of Materials Science: Materials in Medicine, 2005, pp. 933-946, vol. 16.
Zhong et al., An aligned nanofibrous collagen scaffold by electrospinning and its effects on in vitro fibroblast culture, Journal of Biomedical Materials Research Part A, 2006, pp. 456-463.
Berrier et al., Cell-Matrix Adhesion, Journal of Cellular Physiology, 2007, pp. 565-573, vol. 213.
Block et al., Population Expansion, Clonal Growth, and Specific Differentiation Patterns in Primary Cultures of Hepatocytes Induced by HGF/SF, EGF and TGFα in a Chemically Defined (HGM) Medium, Journal of Cell Biology, Mar. 1996, pp. 1133-1149, vol. 132, No. 6.
Boland, et al., Tailoring Tissue Engineering Scaffolds Using Electrostatic Processing Techniques: A Study of Poly(glycolic acid) Electrospinning, J. Macromol. Sci.-Pure Appl. Chem., 2001, pp. 1231-1243, vol. A38, No. 12.
Brandrup et al., Polymer Handbook, Fourth edition, 1999, 3 pages, John Wiley & Sons, Inc., New York.

(Continued)

*Primary Examiner* — Taeyoon Kim
(74) *Attorney, Agent, or Firm* — The Webb Law Firm

(57)    ABSTRACT

Provided herein are apparatus and systems for fabricating highly aligned arrays of polymeric fibers having isodiameters ranging from sub 50 nm to microns with lengths of several millimeters. The approach disclosed herein uses (e.g.) a micropipette to deliver polymeric solution which is collected in the form of aligned fibers on a rotating and linearly translating substrate. The methods deposit polymeric fibers on spherical surfaces and gapped surfaces with precise control, thus heralding new opportunities for a variety of applications employing polymeric fibers. The design workspace for depositing fibers disclosed herein is dependent upon processing parameters of rotational/linear translational speeds and material properties of solution rheologies. Techniques for fabrication of multilayer fiber arrays, for fabrication of cell growth scaffolds and for attachment of particles to the fiber arrays are also disclosed.

45 Claims, 55 Drawing Sheets

(56) References Cited

OTHER PUBLICATIONS

Doufas et al., Simulation of melt spinning including flow-induced crystallization Part I. Model development and predictions, Journal of Non-Newtonian Fluid Mechanics, 2000, pp. 27-66, vol. 92.
Engler et al., Matrix Elasticity Directs Stem Cell Lineage Specification, Cell, Aug. 25, 2006, pp. 677-689, vol. 126.
Flemming et al., Effects of synthetic micro- and nano-structured surfaces on cell behavior, Biomaterials, 1999, pp. 573-588, vol. 20.
Gou et al., A Comparison of Newtonian and Viscoelastic Constitutive Models for Dry Spinning of Polymer Fibers, Journal of Applied Polymer Science, 2003, pp. 2136-2145, vol. 87.
Graessley, Polymeric Liquids and Networks: Structure and Properties, Garland Science, 2004, 3 pages, New York.
Graessley, Polymer chain dimensions and the dependence of viscoelastic properties on concentration, molecular weight and solvent power, Polymer, Mar. 1980, pp. 258-262, vol. 21.
Graham et al., Microscopic theory of linear, entangled polymer chains under rapid deformation including chain stretch and convective constraint release, J. Rheol. Sep./Oct. 2003, pp. 1171-1200, vol. 47, No. 5.
Guhados et al., Measurement of the Elastic Modulus of Single Bacterial Cellulose Fibers Using Atomic Force Microscopy, Langmuir, 2005, pp. 6642-6646, vol. 21.
Gupta et al., Electrospinning of linear homopolymers of poly(methyl methacrylate): exploring relationships between fiber formation, viscosity, molecular weight and concentration in a good solvent, Polymer, 2005, pp. 4799-4810, vol. 46.
Gustafson et al., Studies on the Cellular Basis of Morphogenesis in the Sea Urchin Embryo: Directed Movements of Primary Mesenchyme Cells in Normal and Vegetalized Larvae, Experimental Cell Research, 1999, pp. 288-295, vol. 253.
Harfenist et.al., Direct Drawing of Suspended Filamentary Micro- and Nanostructures from Liquid Polymers, Nano Letters, 2004, pp. 1931-1937, vol. 4, No. 10.
Heo et al., The scaling of zero-shear viscosities of semidilute polymer solutions with concentration, J. Rheology, Sep./Oct. 2005, pp. 1117-1128, vol. 49, No. 5.
Huang et al., A review on polymer nanofibers by electrospinning and their applications in nanocomposites, Composites Science and Technology, 2003, pp. 2223-2253, vol. 63.
Huang et al., Electrospun polymer nanofibres with small diameters, Nanotechnology, 2006, pp. 1558-1563, vol. 17.
Jarvik et al., CD-Tagging: A New Approach to Gene and Protein Discovery and Analysis, BioTechniques, May 1996, pp. 896-904, vol. 20, No. 5.
Jarvik et al., Epitope Tagging, Annu. Rev. Genet., 1998, pp. 601-618, vol. 32.
Katagiri et al., Bone Morphogenetic Protein-2 Converts the Differentiation Pathway of C2C12 Myoblasts into the Osteoblast Lineage, The Journal of Cell Biology, Dec. 1994, pp. 1755-1766, vol. 127, No. 6, Part 1.
Larson, The Structure and Rheology of Complex Fluids, 1999, 4 pages, Oxford University Press, New York.
Lee et al., The change of bead morphology formed on electrospun polystyrene fibers, Polymer, 2003, pp. 4029-4034, vol. 44.
Lee et al., Characterization of nano-structured poly(ε-caprolactone) nonwoven mats via electrospinning, Polymer, 2003, pp. 1287-1294, vol. 44.
Liu et al., Tensile Mechanics of Electrospun Multiwalled Nanotube/Poly(methyl methacrylate) Nanofibers, Advanced Materials, 2007, pp. 1228-1233, vol. 19.
McFarland et al., Chemical Sensing With Micromolded Plastic Microcantilevers, Journal of Microelectromechanical Systems, Dec. 6, 2005, pp. 1375-1385, vol. 14, No. 6.
McKee et al., Correlations of Solution Rheology with Electrospun Fiber Formation of Linear and Branched Polyesters, Macromolecules, 2004, pp. 1760-1767, vol. 37.
Milasincic et al., Anchorage-dependent control of muscle-specific gene expression in C2C12 mouse myoblasts, In Vitro Cell. Dev. Biol.-Animal, Feb. 1996, pp. 90-99, vol. 32.
Miller et al., Mechanism(s) of increased vascular cell adhesion on nanostructured poly(lactic-co-glycolic acid) films, J Biomed Mater Res, 2005, pp. 476-484, vol. 73A.
Moissoglu et al., Integrin signalling in directed cell migration, Biol. Cell, 2006, pp. 547-555, vol. 98, No. 9.
Moutos et al., A biomimetic three-dimensional woven composite scaffold for functional tissue engineering of cartilage, Nature Materials, Feb. 2007, pp. 162-167, vol. 6.
Nain et al., Control of Cell Behavior by Aligned Micro/Nanofibrous Biomaterial Scaffolds Fabricated by Spinneret-Based Tunable Engineered Parameters (STEP) Technique, Small, 2008, pp. 1153-1159, vol. 4, No. 8.
Nain et al., Drawing suspended polymer micro-/nanofibers using glass micropipettes, Applied Physics Letters, 2006, pp. 183105-1 to 183105-3, vol. 89.
Nain et al., Microrobotically Fabricated Biological Scaffolds for Tissue Engineering, Proc of IEEE Int Conf on Robotics and Automation (ICRA), Apr. 2007, 3 pages.
Nain et al., Proximal Probes Based Nanorobotic Drawing of Polymer Micro/Nanofibers, IEEE Transactions on Nanotechnology, Sep. 2006, pp. 499-510, vol. 5, No. 5.
Norman et al., Methods for Fabrication of Nanoscale Topography for Tissue Engineering Scaffolds, Annals of Biomedical Engineering, Jan. 2006, pp. 89-101, vol. 34, No. 1.
Papenburg et al., One-step fabrication of porous micropatterned scaffolds to control cell behavior, Biomaterials, 2007, pp. 1998-2009, vol. 28.
Pedicini et al., Mechanical behavior of electrospun polyurethane, Polymer, 2003, pp. 6857-6862, vol. 44.
Pham et al., Electrospinning of Polymeric Nanofibers for Tissue Engineering Applications: A Review, Tissue Engineering, 2006, pp. 1197-1211, vol. 12, No. 5.
Radisic et al., High-Density Seeding of Myocyte Cells for Cardiac Tissue Engineering, Biotechnol Bioeng, 2003, pp. 403-414, vol. 82.
Reneker et al., Nanometre diameter fibres of polymer, produced by electrospinning, Nanotechnology, 1996, pp. 216-223, vol. 7.
Riboldi et al., Electrospun degradable polyesterurethane membranes: potential scaffolds for skeletal muscle tissue engineering, Biomaterials, 2005, pp. 4606-4615, vol. 26.
Rothstein et al., A comparison of the stress and birefringence growth of dilute, semi-dilute and concentrated polymer solutions in uniaxial extensional flows, Journal of Non-Newtonian Fluid Mechanics, 2002, pp. 275-290, vol. 108.
Shenoy et al., Role of chain entanglements on fiber formation during electrospinning of polymer solutions: good solvent, non-specific polymer-polymer interaction limit, Polymer, 2005, pp. 3372-3384, vol. 46.
Silver et al., Biomaterials Science and Biocompatibility, 1999, 5 pages, Springer-Verlag, New York.
Tan et al., Effects of annealing on the structural and mechanical properties of electrospun polymeric nanofibers, Nanotechnology, 2006, pp. 2649-2654, vol. 17.
Tan et al., Novel approach to tensile testing of micro- and nanoscale fibers, Review of Scientific Instruments, Aug. 2004, pp. 2581-2585, vol. 75, No. 8.
Tan et al., Physical properties of a single polymeric nanofiber, Applied Physics Letter, Mar. 1, 2004, pp. 1603-1605, vol. 84, No. 9.
Tan et al., Tensile test of a single nanofiber using an atomic force microscope tip, Applied Physics Letter, 2005, pp. 073115-1 to 073115-3, vol. 86.
Tan et al, Tensile testing of a single ultrafine polymeric fiber, Biomaterials, 2005, pp. 1453-1456, vol. 26.
Zhao et al. Study on correlation of morphology of electrospun products of polyacrylamide with ultrahigh molecular weight. J. Polymer Sci. Part B: Polymer Physics 2005, pp. 2190-2195, vol. 43.
Ramakrishna et al. An Introduction to Electrospinning and Nanofilbers. World Scientific Publishing Co. Pte. Ltd., Singapore, 2005, pp. 112-113.

* cited by examiner

METHODS, APPARATUS, AND SYSTEMS FOR FABRICATION OF POLYMERIC NANO- AND MICRO-FIBERS IN ALIGNED CONFIGURATIONS

CROSS-REFERENCE TO RELATED APPLICATIONS

This application claims the benefit under 35 U.S.C. §119 (e) to U.S. Provisional Patent Application Nos. 61/137,498, filed on Jul. 31, 2008 and 61/223,746, filed on Jul. 8, 2009, both of which are incorporated herein by reference in its entirety.

Methods are provided herein for fabrication of polymeric nano- and micro-fibers. Additionally, a platform for achieving control on fiber diameters ranging from sub-50 nm to several microns is described herein. Polymeric fiber arrays are deposited in aligned configurations in single and multiple layers. Also provided herein are methods of attachment of particles to the fibers. Methods for fabricating polymeric fibrous scaffolds of single and multiple layer configurations are provided for tissue engineering applications.

Nanofibers have found increasing number of applications and hold the potential to revolutionize diverse fields of tissue engineering, smart textiles, sensors and actuators to name a few. Fabricating fibers for textiles has been one of the oldest known technologies producing repeatable and aligned fibers. Well-established techniques of spunbounding, meltblowing, dryspinning, conjugate spinning and $CO_2$ laser thinning produce fibers for textiles having diameters in the micron lengthscales and with lengths in excess of meters. However, aligning and producing long fibers in the sub-micron and nanoscale diameters has been challenging due to fragility of polymeric materials, which makes it difficult to deposit them as one dimensional structures and also to interface them with other systems. Recently, numerous techniques have emerged for fabricating ultra fine fibers of different polymeric systems, with the aim of depositing them in highly aligned configurations. The most popular of these techniques are: electrospinning, template synthesis, phase separation and micro dry spinning. These versatile techniques have been used to demonstrate deposition of a wide variety of polymeric fibers for different applications. However, aligning and depositing fibers of consistent diameters in high densities has been challenging, which limits the development of technologies employing polymeric nanofibers.

Synthetically engineered fibers are traditionally prepared by extruding a polymer solution through a narrow orifice and the extruded filament is then collected on a rotating spindle as a fiber either by wet, dry or melt spinning process. These processes are limited to producing fibers having diameters ranging from tens of micrometers to millimeters. Recently three dimensional point to point fibers having sub-micrometer diameters of Poly-methyl acrylate (PMMA) [Nain A S, et al., IEEE Trans. on Nanotechnology. 2006; 5(5):499-510; Harfenist S A, et. al., Nano Letters. 2004; 4(10):1931] and Polystyrene (PS) [Nain A S et al. Appl Phys Lett. 2006; 89:183105-7] have been demonstrated. However, these recent techniques are limited by the sequential creation of fiber arrays, which is time consuming and additionally, does not provide a precise control on the final fiber diameter. This limits exploiting the advantages of nanoscale building blocks in developing new technologies.

Electrospinning is a common technique for fabricating sub-micrometer fibers [Reneker D H, Chun I., Nanotechnology. 2006; 7:216] and fiber arrays formed by electrospinning are currently used in diverse applications. However, a major drawback of electrospinning is the deposition of fibers in a non woven mat requiring specialized techniques for fiber alignment and the non uniformity in fiber diameters [Huang Z M, et al. Comp Sci Techn. 2003; 63:2223].

Accordingly, there is a need for improved methods, apparatuses, and systems for the fabrication of nano- and micro-fibers with controlled diameters and controlled orientation. Also, there is a need for fabrication of nano- and micro-fibers which have particles attached. Those and other advantages of the methods and apparatus described herein will be described in more detail below.

SUMMARY

Methods and systems are provided for preparing polymeric nano- and micro-fibers, and for optionally attaching particles to said fibers. In this technique, polymer solution is continuously ejected from a micropipette and the fibers are deposited as continuous arrays in parallel and complex geometrical configurations on a substrate, such as a rotating substrate mounted onto a translation stage. As the polymer solution exits the micropipette, solvent evaporation causes solidification of fiber which is then deposited on the rotating form or substrate. For a given polymer, altering the processing and material parameters allows depositing fiber arrays with highly tunable porosities and uniform fiber diameters. The attachment of particles to the fibers adds additional functionality.

Provided herein are methods of preparing high aspect ratio polymeric fibers. In one non-limiting embodiment, the method comprises determining a $C_e$ for a first polymer solution comprising a first polymer and a first good solvent for the first polymer, and pulling a fiber from a first polymer solution comprising the first polymer having a concentration of at least $C_e$ in the first good solvent for the first polymer. More than one polymer can be simultaneously or sequentially deposited by the described methods. Further, irregularities, such as polymer beads can be deposited onto a form or fibers on the form, by depositing a second polymer in a solution in which the concentration of the second polymer is below the $C_e$ for the second polymer.

Optionally, the methods further comprise determining a velocity to pull the fiber to obtain a desired fiber diameter. The fiber can be pulled by any useful method, where non-limiting examples include: contacting the fiber to a target at a contact point; wrapping the fiber about a form; and changing the angle of deposition of the fiber. In one non-limiting embodiment, the contact point is on a rotatable form, wherein one or more of the source of the fiber and the target are attached to a positionable stage. The form can be of any useful configuration. Non-limiting embodiments of the form include a frame comprising one or more perimeter elements defining an opening or a form that is square, circular, oval, rectangular or virtually any custom shape. Frames having fibers wrapped about them can be stacked, or otherwise assembled into larger apparatus, assemblies, etc., such as in filtration elements for filtration devices, such as respirators and or for high strength fabrics due to improved material properties.

As described herein, methods of preparing high aspect ratio polymeric fibers can further comprise depositing a particle onto the fiber. For example and without limitation, the particle is an activated carbon particle.

The polymeric fibers can be formed from any useful polymer. Non-limiting examples of polymers include one or more of a polystyrene, a polyester, a polyurethane, a polyacrylamide, a poly(methyl methacrylate), a polylactic acid, a poly(lactic-co-glycolic acid), fibrinogen and mixtures and copolymers thereof.

Described herein are methods of forming a nonwoven mesh or cell growth scaffold of fibers. For example and without limitation, the method further comprises depositing collagen onto the fibers. Also described herein are methods of growing cells comprising culturing cells on a fiber produced according to the methods of preparing high aspect ratio polymeric fibers. For example and without limitation, the cells are totipotent, pluripotent, or multipotent. Non-limiting examples of cells include neural precursor cells, muscle precursor cells, and hepatocytes. In another non-limiting embodiment, the method comprises fibers in a first layer comprising a first polymer and a second layer comprising a polymer that is the same or different from the first polymer. For example and without limitation, the layers can be parallel or criss-crossed. Cells can be differentiated effectively using the culture methods described herein, as well as maintained for long time periods in a differentiated state, such as is the case with hepatocytes in the example below Also provided is a method of directing cellular migration in a cell growth scaffold, comprising orienting fibers produced as described herein in a geometrical configuration to determine cell migration. In one embodiment, the fibers are oriented in a substantially parallel configuration to direct cell growth along the fibers, as in the formulation of neurons or myotubules. In another embodiment, the fibers are crossed to allow cellular migration across different layers of scaffold. In another embodiment, fibers are oriented in special configurations such as diverging 'V' to inhibit cell migration along the fibers. In another method of inhibiting cell migration along the fibers, particles or polymer beads may be added to the structure.

Also provided herein are methods of preparing cantilevered polymeric fibers, comprising depositing the fibers onto a substrate, typically with fixed boundaries and breaking the fibers by striking the fibers with a suitable microprobe. Atomic force microscopy can be utilized for this purpose, where the fibers can be broken by rapid movement, such as lateral movement of a probe.

BRIEF DESCRIPTION OF THE DRAWINGS

FIG. 1A is a schematic illustrating a non-limiting embodiment of a system with one spinneret. FIG. 1B is a schematic illustrating another non-limiting embodiment of a system with two spinnerets. FIG. 1C is an elevated side view of a non-limiting embodiment of a form. FIG. 1D shows a scanning electron micrograph of aligned fibers with inset at higher magnification.

FIG. 8A is a graph showing the effect of effect of rotational speed (ω) on fiber diameter (data averaged for each rotational speed over approximately 40 fiber diameters). FIG. 8B shows optical images showing the effect of vertical translational speed on fiber spacing: (i, iii) PMMA fibers deposited on spherical geometries and (ii, iv) corresponding doubling in spacing by doubling the linear speed. Average fiber diameter~350 nm.

FIG. 32A is a schematic of spinneret-based point-to-point sequential technique with double attachment strategy shown by a star. FIG. 32B is a scanning electron micrograph of fibers fabricated using the point-to-point sequential technique.

FIG. 38A is a graph showing diameter vs. concentration for PS 860K. Data was averaged over 40 fibers. FIGS. 38C-38D show scanning electron micrographs of fibers deposited at different concentrations of PS 860K.

DETAILED DESCRIPTION

Described herein are polymeric nano- and micro-fibers with controlled diameter and orientation and methods, apparatus, and systems for fabrication of polymeric nano- and micro-fibers with controlled diameter and orientation. The polymeric fibers are deposited in highly aligned configurations on substrates either in single or multiple layers with variable geometrical spacing between them.

In certain embodiments of the methods described herein, a viscous polymer solution composed of a polymer dissolved in a good solvent is pumped continuously through a micropipette spinneret, which is brought in contact with a rotating substrate and retracted, thus stretching the extruded polymer solution volume and forming a solidified fiber by the rapid evaporation of the solvent. The solidified fiber is then collected continuously on the substrate in aligned configurations with user defined geometrical spacing (See FIG. 1A, described in further detail below).

Figure 2:
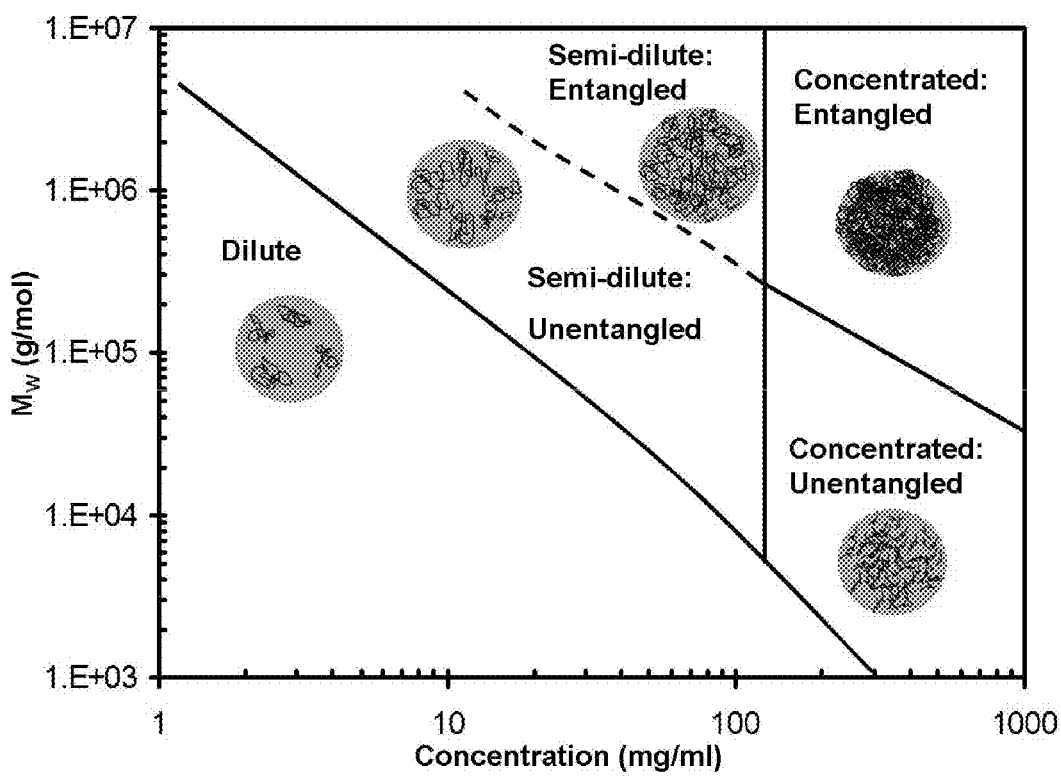
FIG. 2 is a Graessley diagram showing the classification of polymer solutions according to concentration and molecular weight ($M_w$).
Figure 5:
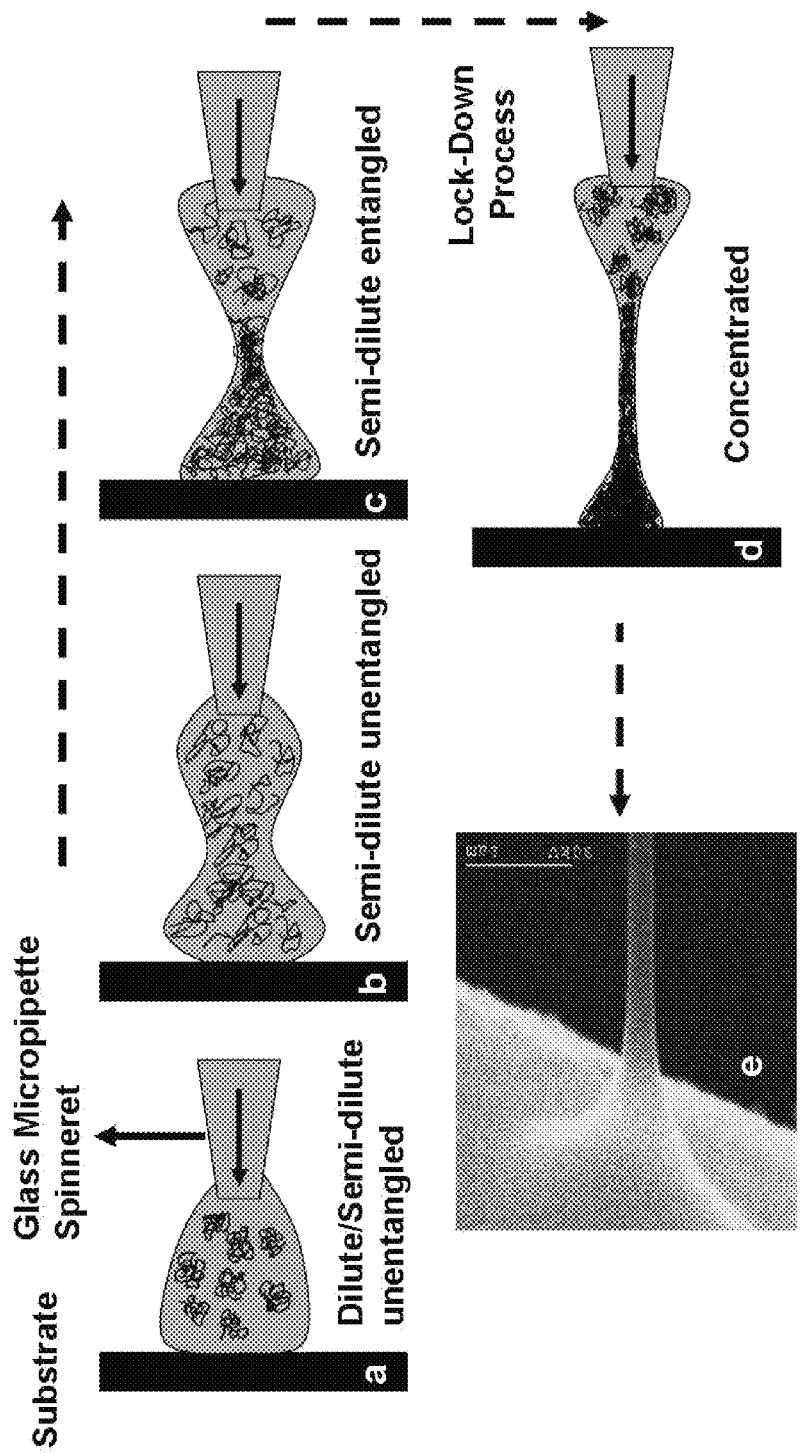
FIG. 5 is a schematic representation of the fiber formation process at different solution rheologies.

Fabrication and deposition of polymeric fibers constitutes a wide design space encompassing automation (processing) and material parameters. Automation parameters of angular speed of rotation and vertical linear speed of translation of the substrate coupled with the material rheological parameters of polymer solution concentration can be optimized to obtain fibers of desired dimensions distributed at tunable geometrical spacing. Fiber formation occurs after a series of complex transformations involving different polymeric concentration domains. At low polymeric concentration in the binary polymer-solvent solution in the dilute solution concentration regime, there are not enough entanglements present to form a continuous fiber and the solution is extruded in the form of droplets. Increasing the polymeric concentration, increases the entanglements and leads to formation of fibers with beaded structures. Smooth and uniform diameter fibers are obtained at the boundary of semi-dilute unentangled and semi-dilute entangled concentration domains as shown in FIGS. 2 and 5. The polymeric fiber diameter dependence on the molecular weight of the polymer follows a similar pattern, whereby higher molecular weight species form bigger diameter fibers compared to lower molecular weight species of the same polymer at the same concentrations. Thus, a comprehensive diagram encompassing different concentrations and molecular weights of the same polymer can be mapped for existence of nanofibers similar to the Graessley diagram for PS (FIG. 2.) [Graessley W W. Polymer chain dimensions and the dependence of viscoelastic properties on concentration, molecular weight and solvent power, Polymer. 1980; 21(3): 258-62].

In one embodiment of a system useful in preparing a scaffold comprising fibers, a micropipette is mounted onto a three degree of freedom stage and is mounted perpendicular to a substrate, or at any suitable angle. The substrate is mounted onto a DC motor, which in turn is mounted onto a motorized three degree of freedom stage. Polymer solution is pumped continuously through the micropipette and the fibers are collected continuously on the rotating substrate.

A "positionable stage" is a stage, substrate, surface, platform, etc. to which an element, such as the source or the target and its associated target assembly, is attached. The stages are translational and/or rotational stages that are positionable in that they can be moved in one, two or three dimensions, permitting and facilitating relative motion of, for example, the target and the source. Movement of the stages in one, two or three dimensions may be accomplished manually or by use of mechanical or electromechanical controllers. The motion of the stage(s) can be computer-controlled, such that tasks such as movement of the target and source relative to each-other can be precisely controlled and repeated—thereby facilitating manufacture of products using the technologies described herein. Design of appropriate and effective mechanical, electrical, computer and robotic systems for performing the steps described herein are well within the abilities of those of ordinary skill in the art of mechanical, electrical, computer and robotic systems design. Commercial sources of stages include Newport Corporation of Irvine Calif.

In the context of translational movement of a stage, the direction of the movement may be said to have a vector in any direction, meaning it can move in any direction that exhibits movement along the stated axis. For example, in the context of movement of a rotating form (target) in a direction having a vector parallel to the axis of rotation of the form, the form can be moved along the axis of rotation, or in any direction so long as the movement is not on a plane that is perpendicular to the axis of rotation, such that there is no movement in the direction of (or parallel to) the axis of rotation. Translational movement in any axis other than in the direction of the axis of rotation would only serve to change the distance between the source and the target. Rotating a spinning form in relation to the polymer so that an angle between the axis of rotation (spin) of the form and the fiber is increased also will have an effect on the deposition pattern.

As used herein, a "polymer" is a compound formed by the covalent joining of smaller molecules, which are referred to herein as residues, or polymer subunits, when incorporated into a polymer. Unless specifically excluded, "polymers" include copolymers, which are polymers comprising two or more different residues, such as block-copolymers. Prior to incorporation into a polymer, the residues typically are described as monomers. Polymers can may have any topology, including, without limitation, straight-chain, branched-chain, star, dendritic, comb, etc. A non-limiting list of useful polymers in the methods and structures described herein includes: polystyrene (PS), polyester, polyurethane, polyacrylamide, poly(methyl methacrylate) (PMMA), poly(2-hydroxyethylmethacrylate) (polyHEMA), polylactic acid (PLA), poly(glycolic acid) (PGA), poly(lactic-co-glycolic acid) (PLGA), poly(caprolactone), etc. A non-limiting list of useful biological polymers include fibrinogen, hyaluronic acid, collagen, gelatin, elastin, and polysaccharides, such as cellulose, amylose, dextran, chitin, chitosan, glycosaminoglycans.

In certain embodiments, the polymers are preferably biocompatible. By "biocompatible," it is meant that a polymer composition and its normal in vivo degradation products are cytocompatible and are substantially non-toxic and non-carcinogenic in a patient within useful, practical and/or acceptable tolerances. By "cytocompatible," it is meant that the copolymers or compositions are substantially non-toxic to cells and typically and most desirably can sustain a population of cells and/or the polymer compositions, scaffolds, devices, copolymers, and degradation products thereof are not cytotoxic and/or carcinogenic within useful, practical and/or acceptable tolerances. For example, a copolymer composition when placed in a human epithelial cell culture does not adversely affect the viability, growth, adhesion, and number of cells. In one non-limiting example, the co-polymers, compositions, and/or devices are "biocompatible" to the extent they are acceptable for use in a human veterinary patient according to applicable regulatory standards in a given legal jurisdiction. In another example the biocompatible polymer, when implanted in a patient, does not cause a substantial adverse reaction or substantial harm to cells and tissues in the body, for instance, the polymer composition or device does not cause necrosis or an infection resulting in harm to tissues organs or the organism from the implanted compositions.

As used herein the term "good solvent" is an art-recognized term, referring to a solvent in which a given polymer chain is more expanded, as opposed to a "bad solvent" where the polymer chain segments stay close to each other. Non-limiting examples of good solvents for polystyrene include xylene, toluene, chloroform, and combinations thereof. Non-limiting examples of good solvents include aromatic hydrocarbons, such as benzene toluene, xylene, and ethylbenzene; and chlorinated aliphatic hydrocarbons, such as methylene chloride, chloroform, and carbon tetrachloride; and other solvents, such as pyridine, acetone, dioxane, dimethylformamide, methyl ethyl ketone, diisopropyl ketone, cyclohexanone, tetrahydrofuran, n-butyl phthalate, methyl phthalate, ethyl phthalate, tetrahydrofurfuryl alcohol, ethyl acetate, butyl acetate, 1-nitro-propane, carbon disulfide, tributyl phosphate, cyclohexane, methylcyclohexane, and ethylcyclohexane, as well as combinations thereof.

As used herein, "$C_e$" or "Ce" refers to the entanglement concentration for a given polymer/solvent combination. "$C_L$" refers to the lock-down concentration for a given polymer/solvent combination. At local polymer concentrations above $C_L$, individual chain mobility is resisted, and the fiber is set in its dry form. As used herein, polymer solutions can be pulled at polymer concentrations at or above the $C_e$, but below the $C_L$, to reproducibly prepare micron or sub-micron diameter high aspect ratio fibers. $C_e$ and $C_L$ can be determined by measuring the viscosity of a polymer dissolved in a good solvent, sa shown in the examples, below.

In one aspect of the methods described herein, for any given polymer/solvent (good solvent) combination, an isodiametric model may be produced which predicts a diameter of the fibers in relation to the concentration of the polymer in a given solvent (see, e.g., Example 7, FIG. 5). In general, for any given polymer/solvent combination:

Diameter (nm)=$x[C/C_e]^{1.5-1.6}$, or Diameter (nm)~$x[C/C^*]^{1.5-1.6}$, where x is a constant specific to the given polymer/solvent combination (see, e.g., Example 7, FIG. 3).

Figure 1A:
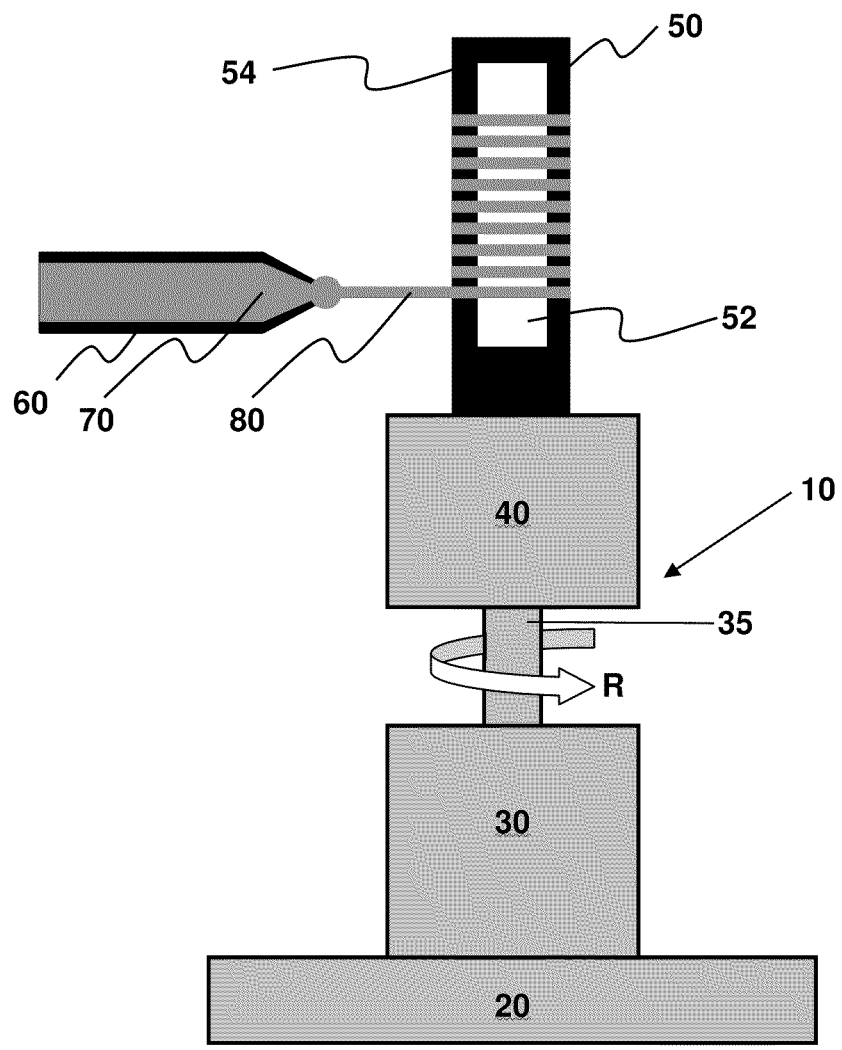
FIGS. 1A-D shows non-limiting examples of systems for preparing high aspect ratio fibers.

In reference to FIG. 1A, one embodiment of a system 10 for preparing high aspect ratio (length/diameter >2000) fibers is depicted schematically. A translatable and/or rotatable stage 20 is attached to a motor 30, such as an electric DC motor. Motor 30 comprises an axle 35 which rotates in direction R. Mount 40 is attached to axle 35. A form 50 is attached to the mount 40. The mount can comprise any useful fastener for attaching a form to the mount, such as a clip or clamp.

Form 50 can have any useful shape. Because certain fibers cannot be elongated beyond a specific length, for example some fibers of less than 100 nm in diameter, the width of any opening in any form having such an opening, should be less than the maximum length of the fibers, to prevent premature breakage of the fiber. Depicted in FIG. 1A is a form 50 that comprises four perimeter elements 54 defining an opening 52. The perimeter elements 54 are arranged in a rectangular fashion, two perimeter elements parallel to each-other, and perpendicular to two other perimeter elements. A rectangular form such as that shown in FIG. 1A may be suitable for use in a filter element, such as in a respirator.

Also shown in FIG. 1A is a spinneret 60, for example consisting of a pipette tip. The pipette can be made of any useful material, such as glass or metal. Polymer solution 70 is fed through the spinneret 60. As described herein, the polymer solution comprises a polymer in a good solvent for the polymer. In use, polymer solution 70 is fed into spinneret 60 and is contacted with the form 50. The spinneret 60 is then moved away from the form 50 (or the form is moved away from the spinneret, or both are moved) thereby forming a fiber 80. Form 50 is then spun in direction R to wrap the fiber 80 about the form 50. Polymer solution is fed through the spinneret at a rate sufficient to compensate for the amount of polymer used to produce the fiber. In one embodiment, the spinerette(s) are sufficient distance from the form or substrate upon which the fibers are to be deposited so that the concentration of the polymer in the polymer solution forming the fiber reaches approximately $C_L$ prior to contacting or wrapping the form or substrate. In an alternate embodiment, where the spinnerette(s) are close enough to the form or substrate, such that $C_L$ is not reached before contact with the form or substrate, a newly-originated fiber will form, which may be desirable under certain circumstances.

Multiple spinnerets may be used to wrap a single form. In reference to FIG. 1B, one embodiment of a system 110 for preparing high aspect ratio fibers with multiple spinnerets is depicted schematically. Similar to the system 10 shown in FIG. 1A, a translatable and/or rotatable stage 120 is attached to a motor 130. Motor 130 comprises an axle 135 which rotates in direction R. Mount 140 is attached to axle 135. A form 150 is attached to the mount 140, where form 150 comprises four perimeter elements 154 defining an opening 152.

Also shown is polymer solution 170 fed through a spinneret 160, and another polymer solution 175 fed through another spinneret 165. In use, polymer solution 170 and another polymer solution 175 is contacted with the form 150. Polymer solution 170 and 175 are fed through their respective spinnerets 160 and 165 at a rate sufficient to compensate for the amount of polymer used to produce the fibers. The spinnerets 160 and 165 are then moved away from the form 150 (or the form is moved away from the spinnerets, or both are moved) thereby forming a fiber 180 of polymer solution 170 and a fiber 185 of polymer solution 175. Spinnerets 160 and 165 can have any useful orientation. For example and without limitation, the orientation of the spinnerets can be modified to optimize the distance between spinneret 160 with respect to spinneret 165. In another non-limiting example, the orientation can be modified to optimize the distance between the spinnerets 160 and 165 with respect to the frame 150.

In system 110, form 150 is then spun in direction R to wrap the fibers 180 and 185 about the form 150. In another non-limiting embodiment, the system 110 comprises a rod 190, where one end of rod 160 is attached to the translatable and/or rotatable stage 120. The other end of rod 160 comprises a pivoting fastener 191, wherein the fastener 191 attaches to the form 150. In certain situations, rod 160 may be used to provide extra support for the form 150 to provide a more rigid structure. The pivoting fastener 191 can have any useful shape, so long as it provides attachment between the rod 160 and the form 150 and as long as it does not significantly hinder the axle 135 which rotates in direction R.

Figure 1B:
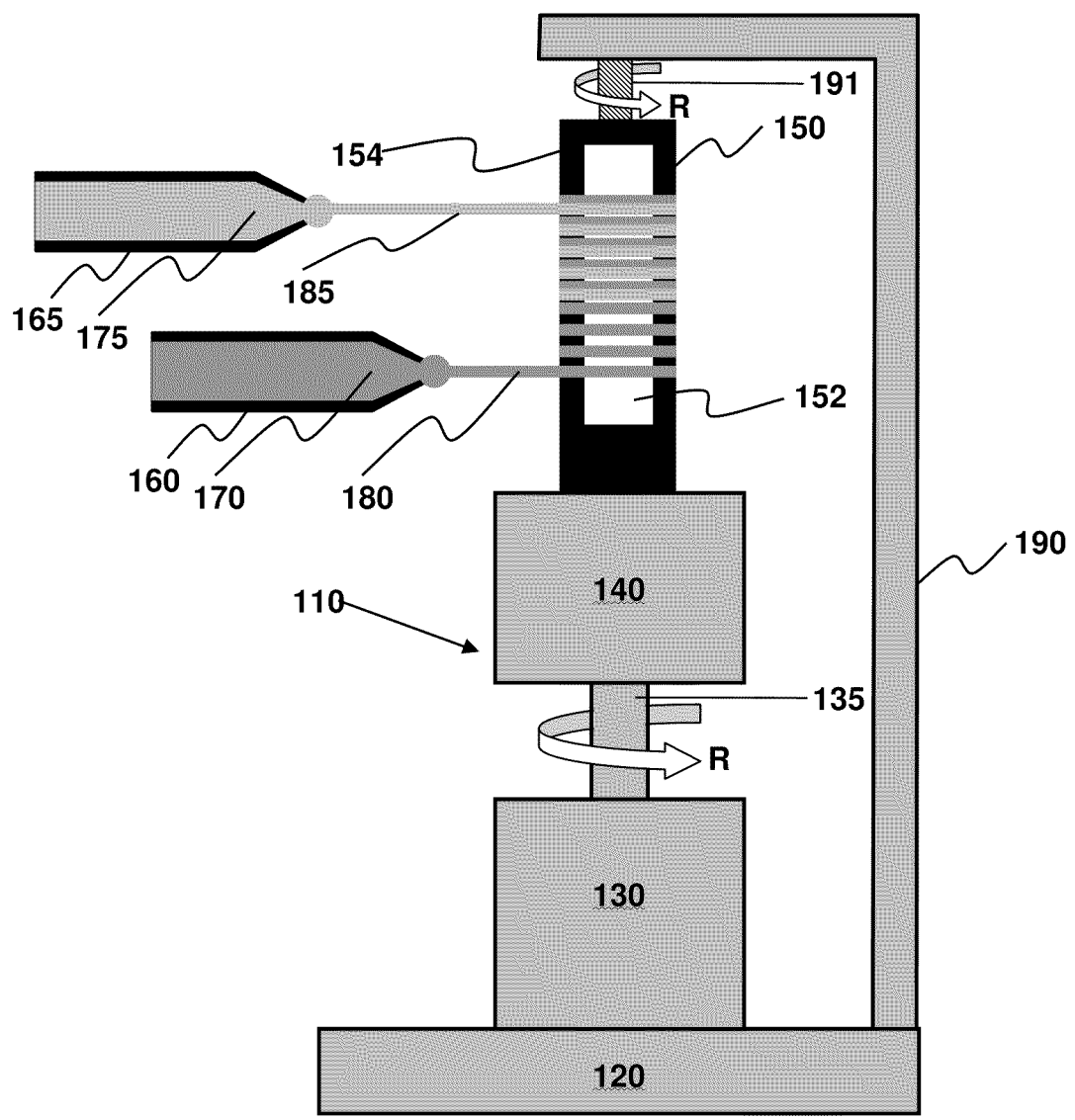
Figure 1C:
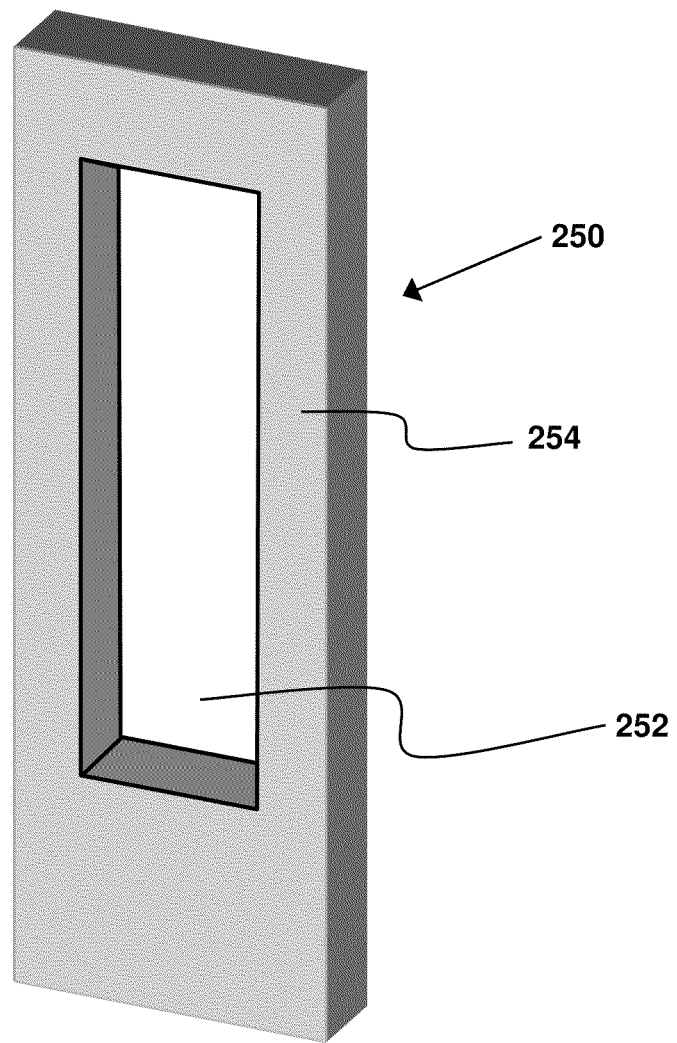

Depicted in FIG. 1C is an elevated side view of a frame 250 that comprises four perimeter elements 254 defining an opening 252. The perimeter elements 254 are arranged in a rectangular fashion, two perimeter elements parallel to each-other, and perpendicular to two other perimeter elements.

The speed of uptake of the fibers by the form or substrate can vary greatly. Above a certain speed or RPM we do not observe change in fiber diameter (see, e.g., FIG. 8A). For a frame of given dimension, such as those described in the examples below, it can be calculated easily for 350 RPM and above. However, it should be noted that we can achieve control on fiber diameter not only through material properties (molecular weight, concentration), but also by rotational speed. Only at very low speeds, we will get non-uniform diameters. Smooth uniform diameter fibers can start forming around 50 rpm or less. In terms of linear speed, smooth fibers can start forming around 5 mm/sec and no change in further diameter are observed at speeds of around 90 mm/sec. and above. In one non-limiting embodiment, the fibers are pulled at a speed at or above a speed in which substantially no further changes in diameter are achieved by increasing the speed. In this embodiment, the identities of the polymer and solvent as well as the concentration of the polymer in the solvent primarily dictate polymer diameter. A method of preparing cantilevered polymeric fibers also is provided herein. A cantilevered fiber refers to a fiber that is bound on one end and free on the other. Accurate and reproducible production of submicron diameter cantilevered fibers, such as for production of nano-probes, is difficult. Methods are provided comprising depositing one or more polymeric fibers on a substrate, and breaking the fiber using a nanometer-scale probe. For example and without limitation, as shown in the examples below, a probe for an atomic force microscope can be used to break polymer fibers that are deposited onto a suitable substrate, such as a transmission electron microscope mesh or a silicon or silicon nitride substrate.

Described herein are scaffolds comprising high aspect ratio fibers and methods of preparing scaffolds comprising high aspect ratio fibers. In one non-limiting example, the scaffold comprises high aspect ratio fibers that can find use as filter units, wherein the scaffold can optionally include particles. In another non-limiting example, the scaffold comprises high aspect ration fibers that can find use as a biological scaffold. For example and without limitation, the biological scaffold is used to culture hepatocytes.

As used herein, the term "aspect ratio" refers to the ratio of the average length of fibers in a scaffold (L) and the average diameter of the fibers within the scaffold (D). The term "high aspect ratio" refers to an aspect ratio of L/D to be more than 2000. For example and without limitation, fibers with an average diameter of 500 nm should have an average length more than 1 mm. In another non-limiting example, fibers with an average diameter on the nanometer scale should have an average length on the millimeter scale.

As used herein, "scaffold" refers to a matrix of high aspect ratio fibers. The matrix can be of any useful geometry and orientation. For example and without limitation, the matrix can comprise nanofibers, a single layer of fibers, or multiple layers of fibers. In one non-limiting example, the matrix comprises fibers that are oriented generally parallel to one another. In another non-limiting example, the matrix comprises fibers that are oriented perpendicular to one another or criss-crossed. Depicted in FIG. 1D is a non-limiting example of a scaffold, where the scanning electron micrograph shows generally parallel fibers with inset at higher magnification.

Figure 1D:
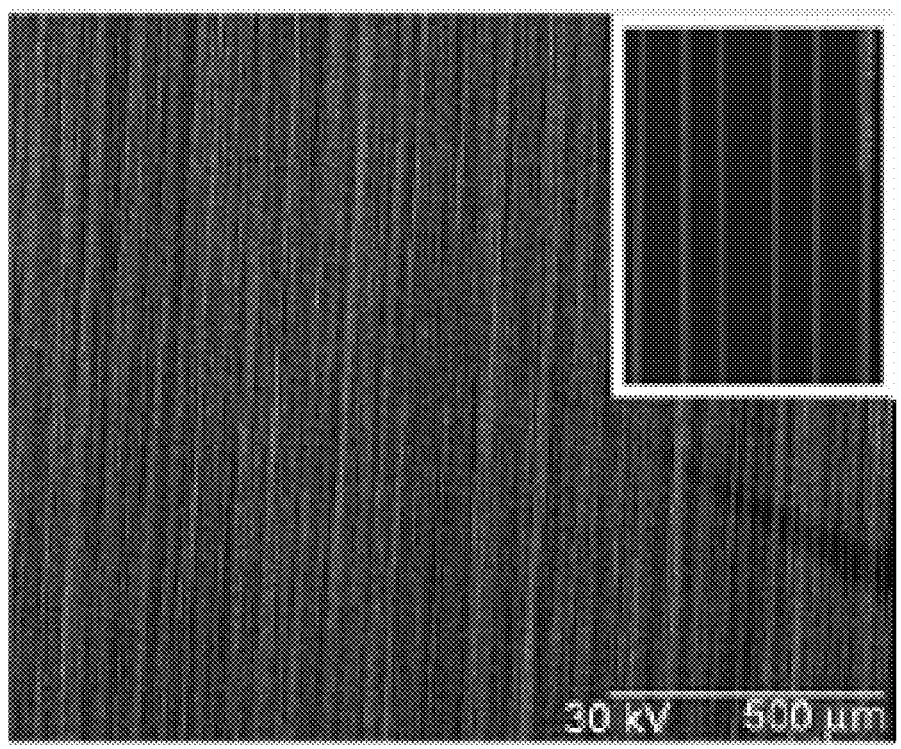

Forms having a frame-structure and wound with a polymer fiber matrix, such as is shown in FIGS. 1A, 1B and 1D can find use in, for example and without limitation, as filter units for filtering a gas or liquid. The minimum size of particles retained by the matrix can be determined by the winding pattern of fibers about the form. Also, the polymers used to wrap the form can be selected for their overall charge to assist in trapping gas- or liquid-borne particles. As described below, particulates may be affixed to the mesh, for instance as described below, by depositing the particulates onto the mesh after it is wound about the form. For example and without limitation, crushed (comminuted) activated carbon particles can be affixed to a wound polymer mesh to increase adsorptive capacity of the mesh.

According to one aspect of the methods described herein, biological scaffolds and methods of preparing biological scaffolds are provided. As used herein, "biological scaffold" refers to a scaffold to be used with biological materials, such as proteins, cells, or organisms. Nonlimiting examples of cells include myocytes, hepatocytes, neurons, and cell precursors, such as cardiac stem cells, myoblasts, neuronal stem cells, and mesenchymal stem cells.

Biological scaffolds are typically biocompatible and may be bioerodable. Bioerodible scaffolds dissolve over a fixed time period when placed in vivo and/or in culture in vitro. Copolymers useful in preparing cell growth scaffolds are well-known known in the art, and include, without limitation, PLGA, PLA, PMMA, polyesters, natural polymers, such as fibrinogens, collagens, extracellular matrix (ECM)-derived polymers and mixtures thereof. In the context of the fabrication methods described herein, layers of varying fiber orientations and compositions, can be manufactured using single and multiple spinneret (that is, one or more polymer types) systems. For example, a matrix or scaffold can be manufactured using a first layer of PS, with a mixture of PLGA and fibrinogen in a second layer. The biological scaffold can be made from any useful material, such as biocompatible materials, including biological polymers; biocompatible polymers; ceramics; metal; metal oxides, such as titanium, tantalum, nitinol; and combinations thereof.

In one non-limiting embodiment, the biological scaffold can be further treated to provide a biocompatible surface. For example and without limitation, the scaffold can be treated to provide a sterilized surface for proteins and/or cells. Non-limiting examples of sterilization treatments include: exposure to ultraviolet light; autoclave; exposure to high heat; irradiation, such as gamma irradiation; exposure to aseptic solvents, such as ethanol; and exposure to plasma. In another non-limiting example, the scaffold can be treated with an agent to provide for a biocompatible and/or cytocompatible surface. Non-limiting examples of agents include: proteins, such as collagen, vitronectin, laminin, fibronectin, fibrinogen, gelatin, and alginate; polymers, such as poly(ethylene glycol), poly(lysine), poly(ornithine); peptides, such as those incorporating RGD or YIGSR; and growth factors, such as one or more of: basic fibroblast growth factor (bFGF), acidic fibroblast growth factor (aFGF), vascular endothelial growth factor (VEGF), hepatocyte growth factor (HGF), insulin-like growth factors 1 and 2 (IGF-1 and IGF-2), platelet derived growth factor (PDGF), stromal derived factor 1 alpha (SDF-1 alpha), nerve growth factor (NGF), ciliary neurotrophic factor (CNTF), neurotrophin-3, neurotrophin-4, neurotrophin-5, pleiotrophin protein (neurite growth-promoting factor 1), midkine protein (neurite growth-promoting factor 2), brain-derived neurotrophic factor (BDNF), tumor angiogenesis factor (TAF), corticotrophin releasing factor (CRF), transforming growth factors α and β (TGF-α and TGF-β), interleukin-8 (IL-8), granulocyte-macrophage colony stimulating factor (GM-CSF), interleukins, and interferons.

In use, biological scaffolds as described herein, may be deposited on any suitable cell culture vessel, including plastic or glass vessels, such as flasks, plated, bottles, or any suitable container for culturing cells or tissue.

According to one aspect of the methods described herein, methods of growing cells are provided. As used herein, "growing cells" refers to maintaining cells in culture, including but not limited to adhesion, proliferation, migration, differentiation, and/or aggregation of cells. As described herein, cell migration, orientation and shape can be dictated by the fiber orientation of the scaffold prepared according to the methods described herein. In one non-limiting embodiment, myotubules can be manufactured by depositing a muscle precursor cell onto bundles of substantially parallel fibers of PS or other polymers. Liver cells can be grown crossed layers of polymers. Neurons from neural stem cells could be harnessed in higher concentrations on such scaffolds. Cell migration is seen along fibers and is inhibited by imperfections in the fibers, such as beading. Thus, a benefit of the fiber and matrix fabrication methods described herein is that high quality fibers and bundles and matrices thereof can be fabricated, that permit un-hindered cell migration, yet imperfections, such as beads or particulates, can be manufactured into the matrix to produce barriers to cell migration, while increasing cellular attachment density.

Cells can be grown in culture media appropriate for growth and differentiation of any given cell type. Growth factors and cytokines, as are known in the art, can be used to induce cellular growth and differentiation. The choice of cells to propagate within the matrix depends on the intended use. Stem cells (totipotent, pluripotent or multipotent) or other precursor cells would be useful for producing many cell types. Muscle progenitor cells would be useful for producing muscle tissue. Hepatocytes would be useful for producing liver tissue. Aortic cells or cardiomyocytes would be useful for producing aortic or cardiac muscle tissue. Neural stem cells would be useful for producing nerve tissue. Different form shapes can be manufactured for different end uses. The matrices may be wrapped upon a sacrificial for, such as one made from a starch, salt or sugar that can be dissolved once deposited on the form, leaving a lumen. Matrices prepared by any method described herein can be compressed into forms to produce larger structures.

As is shown, the relative position of the form and the spinneret may be moved so that the fiber is spaced on the form in a desired pattern. To do so the spinneret and/or the form may be moved in a direction having a vector parallel to the axis of rotation of the form. If the movement is steady (does not vary substantially), the spacing of the fibers on the form will be regular. A criss-crossed pattern can be generated in a two-step (or more) process. The first step deposits fibers in one direction, essentially as shown in FIG. 1A. For the second step, the form is removed, rotated 90° and reattached to the mount so that the already-deposited fibers are aligned (e.g.) 90° to the direction the second layer are to be deposited (which would be vertically in the context of FIG. 1A). Other patterns may be generated by altering the position of the form in relation to the spinneret(s) and/or rotating the frame in the mount.

As described above, the concentration of the polymer in the polymer solution is at or above the $C_e$ for the particular polymer/solvent combination. As the fiber is pulled from the polymer solution, the solvent evaporates, thereby increasing the local concentration of the polymer until $C_L$ is reached, at which point, the fiber is formed (see FIG. 5). As described herein, the speed at which the fiber is pulled and the distance between the spinneret and the form is optimized empirically so that the fiber is deposited correctly onto the form. FIG. 1D shows the exceptional quality of the fibers produced by methods described herein.

The entire process, including relative motion of the spinneret(s) and form, and rotation of the form can be controlled manually. Nevertheless, in order to scale up the process for commercial manufacturing, the motion of the respective elements of the device can be controlled by a computer. A computer includes any implementation of computing processes, and may be implemented on a single Personal Computer (PC), laptop, workstation, PDA, etc. A computer comprising one or more processes for controlling motion of the respective elements of the systems described herein includes, without limitation, any configuration of computer(s), computer hardware, processors, computer software and/or data storage (temporary, such as RAM, or long-term, such as hard drive) that is useful in performing the stated tasks/processes. Implementation of algorithms and tasks described herein is well within the abilities of those of skill in the art using suitable software and/or hardware.

Figure 4:
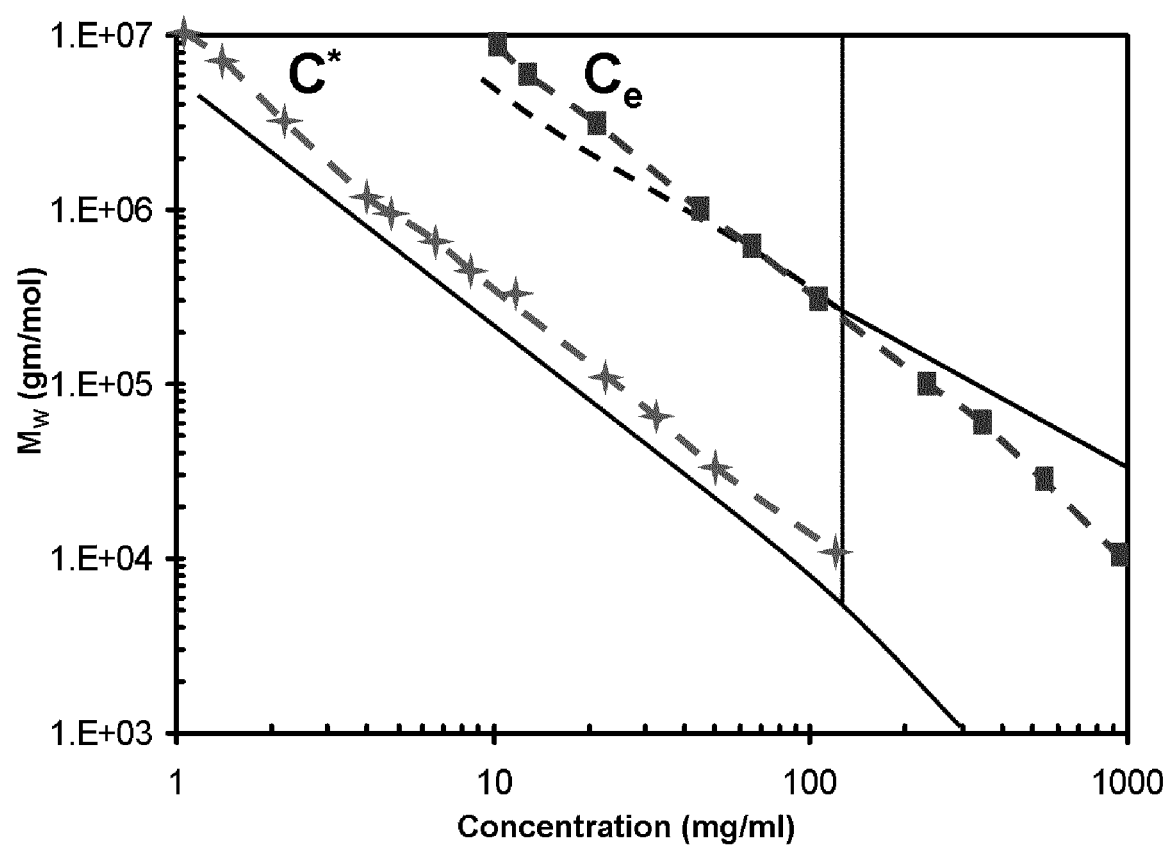
FIG. 4 is a graph showing critical chain overlap concentration (C*) and critical entanglement concentration ($C_e$) plotted on the Graessley diagram.

Thus described herein is a method of preparing a high aspect ratio polymeric fiber comprising determining a $C_e$ (e.g., obtained by mapping mathematically on a Graessley diagram for respective polymer, see, e.g., FIG. 4) for a polymer solution comprising a polymer and a good solvent for the polymer, and pulling a fiber from a polymer solution comprising the polymer having a concentration of at least $C_e$ in the good solvent for the polymer. The method may further comprise determining a velocity to pull the fiber in order to obtain a desired fibered diameter and pulling the fiber at the rate.

Parameters constituting the design space for fabricating fibers with desired attributes can be divided into two categories: material and processing. Material parameters of polymer solution concentration, polymer structure, polymer molecular weight and processing parameter of angular speed of rotation of the substrate at a given flow rate can be optimized to obtain fibers of desired fiber dimensions. Methods are disclosed to repeatably deposit high aspect fibers having diameters ranging from sub 50 nm to microns (µ), and having lengths in excess of several millimeters. The control parameters disclosed herein for representative polymers, can be extended to other polymeric systems Example 1

The effects of material parameters of solvent, viscosity, molecular weight and concentration have been studied using electrospinning process [McKee M G, et al. Macromolecules. 2004; 37:1760; Gupta P et al., Polymer. 2005; 46:4799] and scaling laws based upon experimental observations have been reported. Polystyrene (PS) polymer solutions can be classified into five different regimes according to concentration and molecular weights as shown in FIG. 2 (Graessley diagram (GD)), [Graessley W W, Polymer, 1980; 21:258]. The master curves in FIG. 2, can be used to investigate the design space for fiber formation process using a pseudo dry spinning process for PS. It is of interest to deposit fibers of required dimensions having molecular weights ranging from tens of thousands to several million gm/mol. Low molecular weight polymer fibers lack the strength of high molecular weight fibers and can be used to develop sensors in the form of fibers which break at very low strains and conversely the high molecular weight polymer fibers can be used for sensing requiring higher strains or for strengtheners in developing advanced materials and fabrics.

For homogeneous solutions of a linear polymer, the dimensionless product of intrinsic viscosity, [η] with the polymer concentration c is referred to as the Berry number, $B_e$. The significance of this number arises from the fact, that for solutions to have chain entanglements (i.e in the semi-dilute regime), $B_e > 1$. In dilute solutions, $B_e \sim 1$, with no chain entanglements. The intrinsic viscosity, [η] can be related to the molecular weight (M) of a linear polymer by the Mark-Houwink-Sakurada equation:

$$[\eta] = KM^a \quad (1)$$

where the constants K and a depend on the polymer, solvent and temperature. Intrinsic viscosity also gives a measure of the critical chain overlap concentration c*, which is defined as the crossover from the dilute to the semi-dilute unentangled concentration regimes. The critical concentration can be expressed as [Graessley W W, Polymer. 1980; 21:258]

$$c^* = \frac{6^{3/2} M}{8 N_a R^3(0)} \quad (2)$$

where $R^2(0)$ is the mean-squared end-to-end distance at zero concentration. The intrinsic viscosity can be described using the Fox-Flory equation:

$$[\eta] = \phi \frac{R^3(0)}{M}. \quad (3)$$

The Flory constant φ is independent of the polymer-solvent system for linear chains and $\phi \approx 2.5 \times 10^{23}$ (c.g.s units). Equation 3 can be substituted in equation 2 to obtain the important relationship:

$$c^* = \frac{0.77}{[\eta]} \sim \frac{1}{[\eta]} \quad (4)$$

From equation 4, it is clear that c*[η]~1 scales in the dilute solution limit and can be used to estimate the onset of chain entanglements in a polymer solution. Intrinsic viscosity can be calculated using equation 1, provided the constants are available.

Figure 3A:
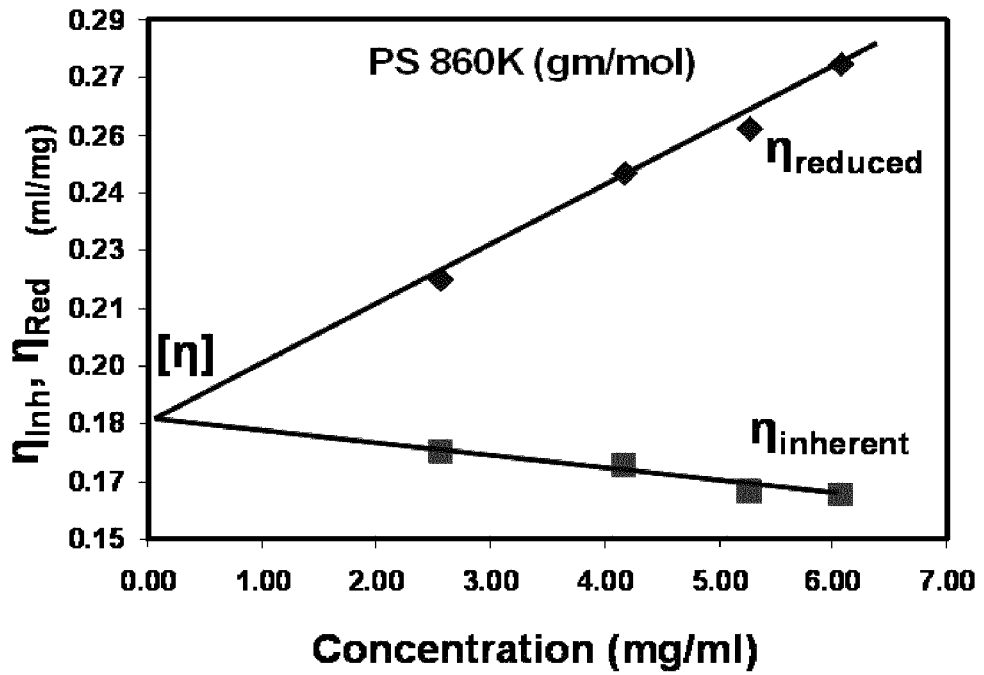
FIGS. 3A-3B are graphs showing the calculation in intrinsic viscosity and calculation of Mark-Houwink-Sakurada constants from intrinsic viscosities of a series of molecular weights.
Figure 3B:
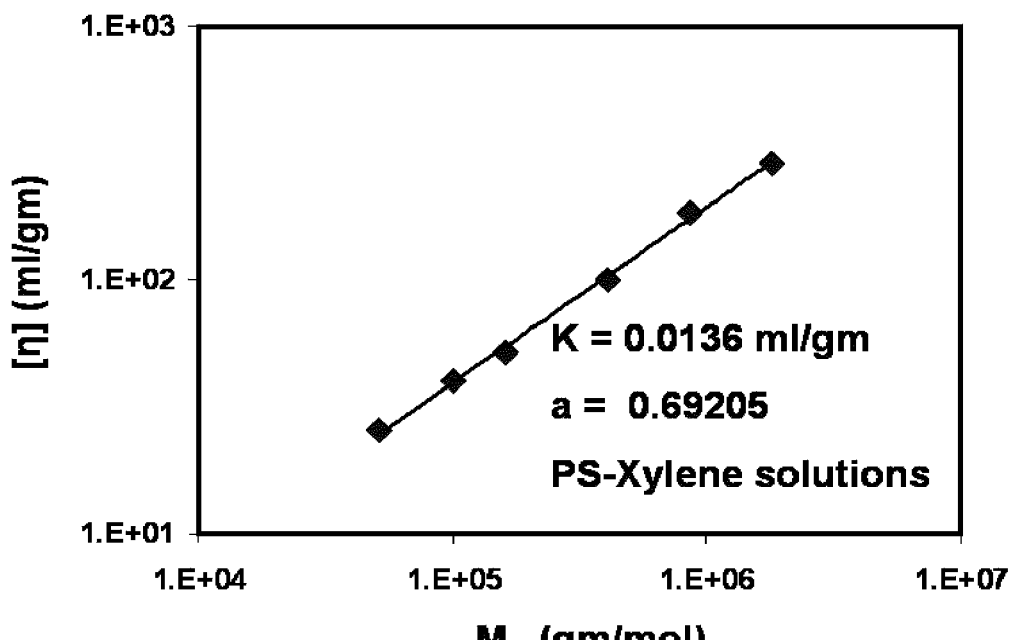

To accurately determine the onset of chain entanglements, PS solutions were dissolved in Xylene at low concentrations~1% by weight in xylene and dilute solution viscometry experiments on different molecular weights of PS (50, 100, 160, 411, 860 and 1800K (gm/mol)) were conducted @ 30° C. to obtain the intrinsic viscosity and also the Mark-Houwink-Sakurada constants. The intrinsic viscosity is calculated from the plot of dimensionless reduced and inherent viscosities as shown in FIG. 3A. A plot of inherent viscosities of a range of molecular weights in dilute solutions provides the Mark-Houwink-Sakurada constants as shown in FIG. 3B. The obtained constants (K=0.0136 ml/gm and a=0.69205 @ 30° C.) are in close agreement with the reported constants of PS-Toluene systems (K=0.00848 ml/gm and a=0.748 @ 25° C.) (Brandrup J & Immergut E H, eds. Polymer Handbook, 2nd ed., Wiley-Interscience, New York 1975). Using equation 1, the intrinsic viscosities and critical chain overlap concentrations for a series of PS molecular weights are tabulated in Table 1.

TABLE 1

Intrinsic viscosity ([η]) and critical chain overlap concentration (C*) for PS with varying molecular weights (Mw).

| Mw (gm/mol) | [η] (ml/gm) | C* (gm/ml) |
|---|---|---|
| 5000 | 4.94 | 0.2026 |
| 50000 | 24.29 | 0.0412 |
| 100000 | 39.25 | 0.0255 |
| 290000 | 82.00 | 0.0122 |
| 411000 | 104.38 | 0.0096 |
| 650000 | 143.34 | 0.0070 |
| 860000 | 173.98 | 0.0057 |
| 1650000 | 273.12 | 0.0037 |
| 1800000 | 290.07 | 0.0034 |
| 2000000 | 312.01 | 0.0032 |

Four molecular weights (100, 411, 860 and 1800K (gm/mol) were then selected for fiber deposition experiments. These molecular weights provide enough design space spanning from dilute to semi-dilute to concentrated regimes for demonstrating the effects of solution rheologies of linear polymers towards fabricating fibers of diameters ranging from sub-50 nm to micron length scales as shown in FIG. 4.

Example 2

Fiber Fabrication

The critical chain overlap concentration obtained experimentally for the selected molecular weights is plotted on the master curve GD as shown in FIG. 4. It is evident from the figure that the experimentally observed critical overlap concentrations match with the master curve of GD. To determine the design space for fiber fabrication, experiments were conducted to identify processing and material parameters. Fiber formation occurs by a locked down glassy state of entangled polymer chains in the concentrated polymer solution regime. Schematic representation of fiber formation from dilute to concentrated regimes is shown in FIG. 5. Initially the solution is in the dilute/semi-dilute concentration regime, with the polymer molecules swollen in a good solvent and at large distances from each other (FIG. 5(a)). Solvent evaporation causes the local concentration to increase rapidly, leading to semi-dilute unentangled concentration regime (FIG. 5(b)). Further evaporation leads to more entanglements and lock down state of the fiber formation begins (FIG. 5(c)). At some point in the process, the concentration transitions over to the concentration regime, where by the molecular chains lose their individual mobility and are locked down, leading to fiber formation (FIG. 5 (d)), and a characteristic neck in the beginning of fiber is formed which transitions to a one dimensional fiber structure (FIG. 5(e)).

Figure 6:
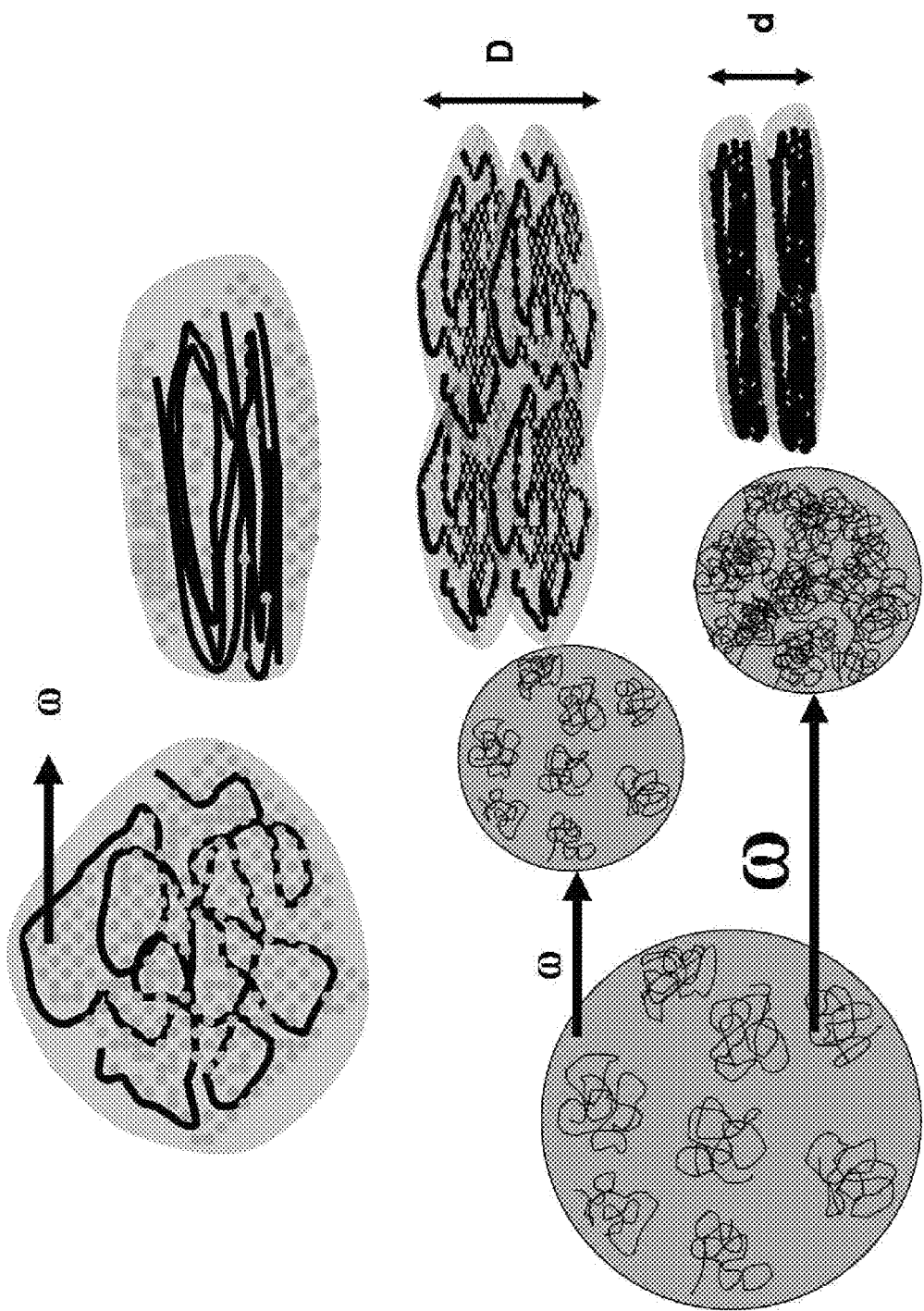
FIG. 6 is a schematic representation of the effect of rotational speed (ω) on solvated molecules and on fiber diameter (d and D).

It is important to note that the initial polymer solution can be in any concentration domain, but the lock down process occurs by transitioning over to the concentrated regime. Hence, the fiber diameter is strongly a function of solution rheology and molecular weight of the polymer species. Similarly, thought experiments can be schematically represented for the effect of processing parameters (rotational speed) on the fiber formation process (FIG. 6). A solvated molecule can be thought of being surrounded in a sea of solvent molecules with the assumption of partially draining molecules for lower molecular weight species with the solvent molecules penetrating inside the molecule. Upon application of an external field, such as a velocity field, the solvent molecules apply a shear force on the polymeric chains resulting in possible short order chain orientation and elongation (FIG. 6A). The entropic tensile forces of the molecules being stretched, lead to molecular chains getting unentangled and coil-stretch experiments on dilute solutions have shown chains stretching completely at high strain rates [Larson R G., The structure and rheology of complex fluids, Oxford University Press, 1999]. The higher the rotational speed, the larger the drag forces exerted by the solvent molecules on the polymer chains, which leads to larger deformation of the chains leading to lower diameter of the fiber (FIG. 6B). In entangled systems, at high strain rates, the partially oriented chains lead to strain hardening which limits the effect of rotational speed [Rothstein J P & McKinley G H, J Non-Newtonian Fluid Mech. 2002; 108:275]. Thus, by appropriate combination of material and processing parameters, the strategy described herein provides a unique platform for depositing nano/micro fibers.

Figure 7A:
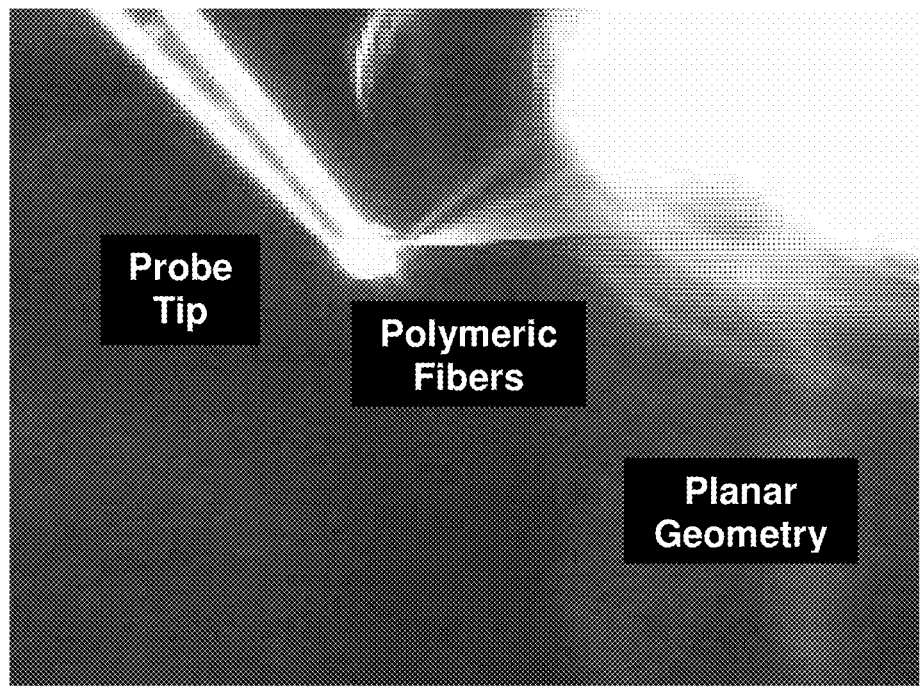
FIGS. 7A-7B are optical images of the fiber deposition process (A) on a planar geometry and (B) on a spherical geometry.
Figure 7B:
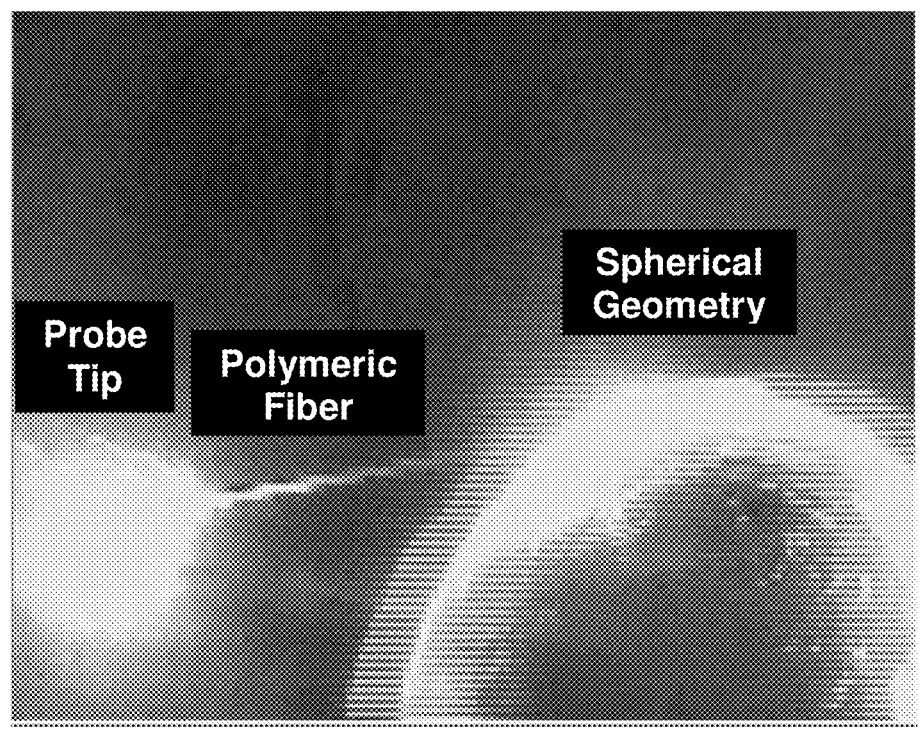

The key processing parameters of interest are the rotational and the linear speed of the substrate and they can be optimized to obtain the desired porosity or geometrical spacing between fibers. In the present example, the probe tip can be mounted at an angle or perpendicular to the rotating substrate (FIG. 7A-B). Glass probe tips can be short lived, hence the setup can be easily improved by using metallic probe tips and proper alignment strategies. This coupled with conducting the experiments in a controlled environment of temperature, humidity and impurities can greatly increase the repeatability of experiments, besides the survivability of deposited fibers.

Rotational speed, on the other hand, has a pronounced effect on the fiber diameter, besides the obvious geometrical spacing. The effect of rotational speed on the fiber diameter is demonstrated in FIG. 8A. Fiber diameter is observed to decrease rapidly with the increase in the rotational speed and reaches a plateau. It can be hypothesized that the slow takeup speeds do not provide enough shear forces for the solvent molecules to stretch the molecules by disentanglement. Additionally, the tensile forces within the fiber are not constant and they increase with the length of the fiber. The small tensile forces at low takeup speeds do not aid in the stretchability of the fiber. However, increasing the speed provides for chains partially disentangling and the increased tensile forces stretch the fiber, thus decreasing the fiber diameter. At even higher speeds, the increased tensile forces and the increased convective air transport over the fiber surface, forces a locked down situation, whereby the diameter remains constant. These findings are in agreement with the traditional diameter profiles of fibers in dry and melt spinning [Gou Z, et al., J Appl Polymer Science. 2003; 87:2136; Doufas A K et al. J. Non-Newtonian Fluid Mech. 2000; 92:27]. The importance of rotational speed in the overall design space of fabricating fibers using the proposed technique lies in the ability to deposit fibers having diameters from micron lengthscales to sub-500 nanometers for a concentrated solution of high molecular weight. To investigate the design space from 50-500 nm of other molecular weights, material parameters were investigated and the processing parameter of rotational speed was kept constant at 550 rpm.

Figure 8A:
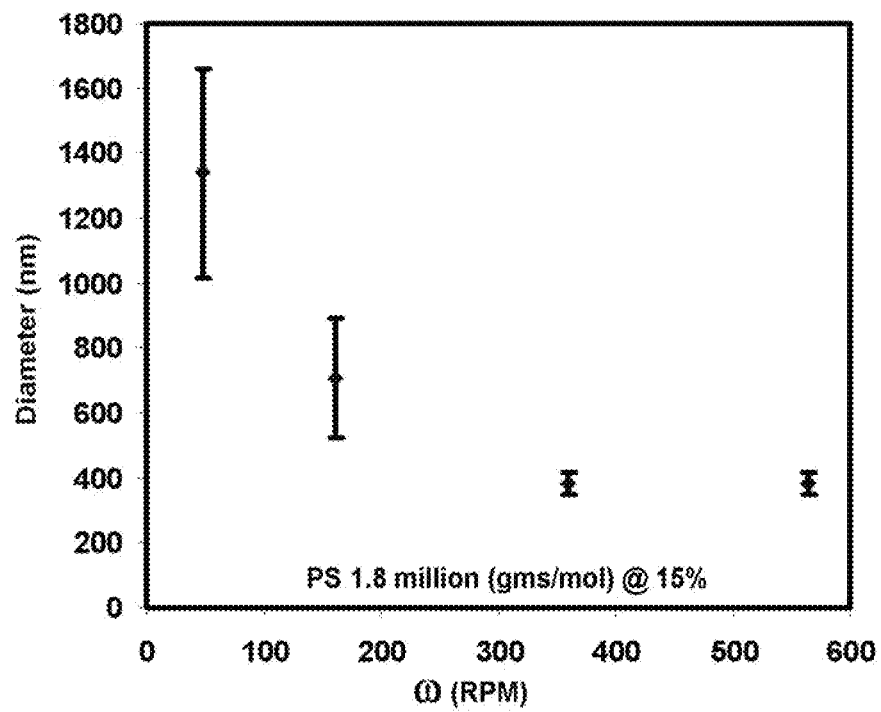
FIGS. 8A-8B show the effect of the processing parameters on fiber formation.
Figure 8B:
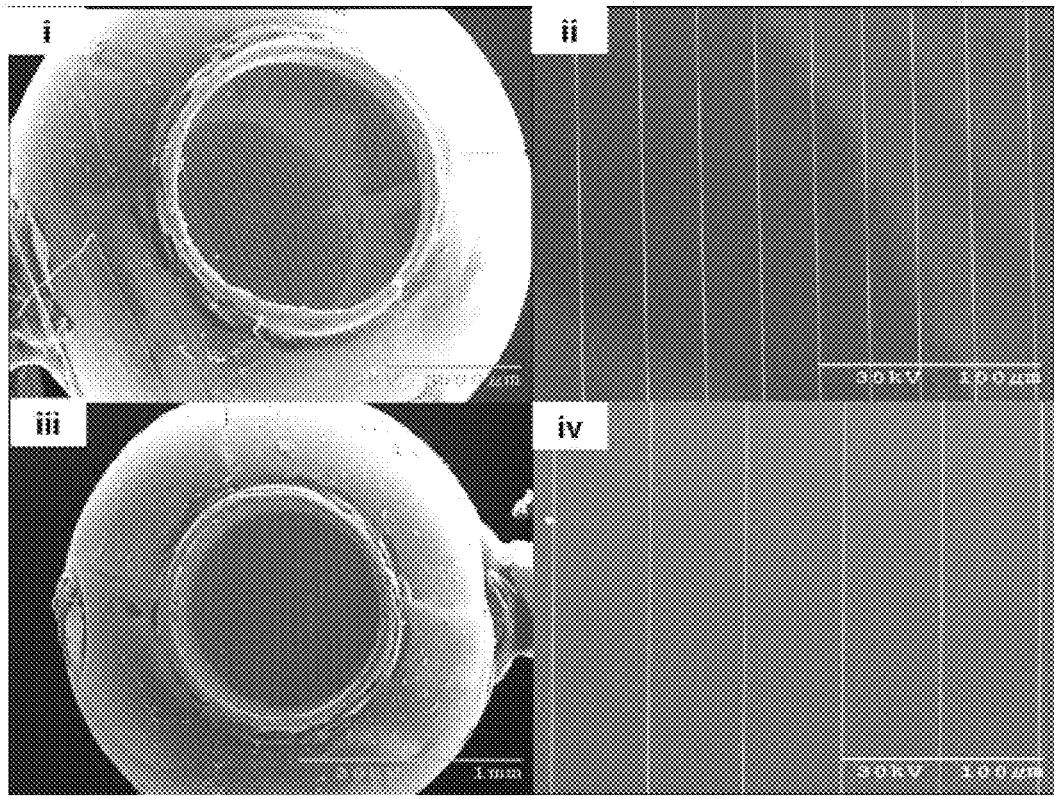

Using the setup shown in FIG. 7B, PMMA fibers were deposited on spherical surfaces as shown in FIG. 8B. The effect of doubling the linear speed (FIG. 8B(i, iii)) is demonstrated by the increase in the geometrical spacing in between the fibers deposited on the spherical substrates (FIG. 8B(ii, iv)). Thus, linear speed of the vertical translating stage can be used to deposit fibers of constant diameter with tunable geometrical spacing between the fibers. The ability to deposit aligned fibers in planar and spherical geometrical configurations in high densities makes this technique very attractive for developing next generation biological scaffolds, novel sensors, filters and fabrics.

Material Parameters:

Another important aspect is the determination of the effect of solution concentration and molecular weight on fiber diameter for a given length of fiber. Best results were obtained when the fiber lengths were several millimeters. Electrospinning has been used extensively to understand the formation, shape, texture and morphology of deposited fibers and it is the current state of the art technology for depositing fibers having diameter ranges from 50-500 nm. Previous studies on electrospinning have shown that for many polymer/solvent systems, increasing the solution concentration or viscosity decreases the number of bead defects and increases the overall fiber diameter. Similar trends in decrease of fiber diameter with the decrease in molecular weight have been reported as well and experimental scaling laws of diameter vs. concentration for electrospinning have been proposed [McKee M G et al., Macromolecules. 2004; 37:1760; Gupta P, et al. Polymer. 2005; 46:4799].

Figure 9A:
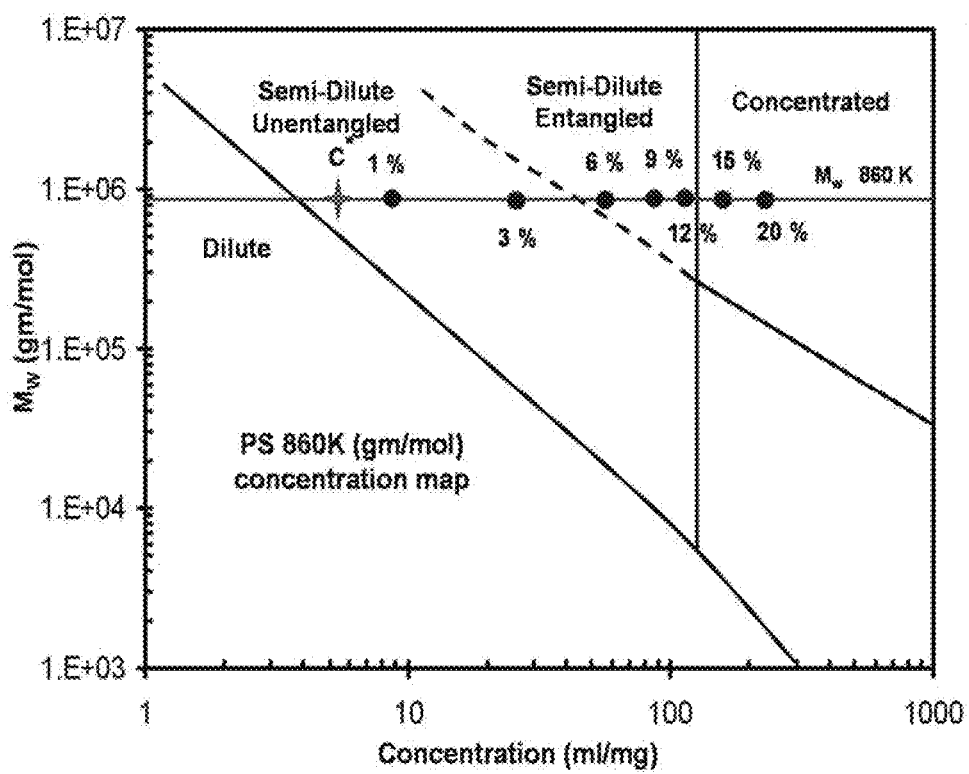
FIGS. 9A-9B are graphs showing (A) Polystyrene (PS)_860K (gm/mol) polymer solution maps for experiments spanning different concentration domains with C* (chain overlap concentration), and (B) $R_G$ (radius of gyration), $M_E$ (entanglement density), and experimentally obtained $D_{Experiment}$ (diameter) of fibers as a function of solution polymer concentration. Data for diameters was averaged over 40 fibers for each concentration. Onset of uniform diameter (defect-free) fibers was observed approximately at 6% solution concentration.
Figure 9B:
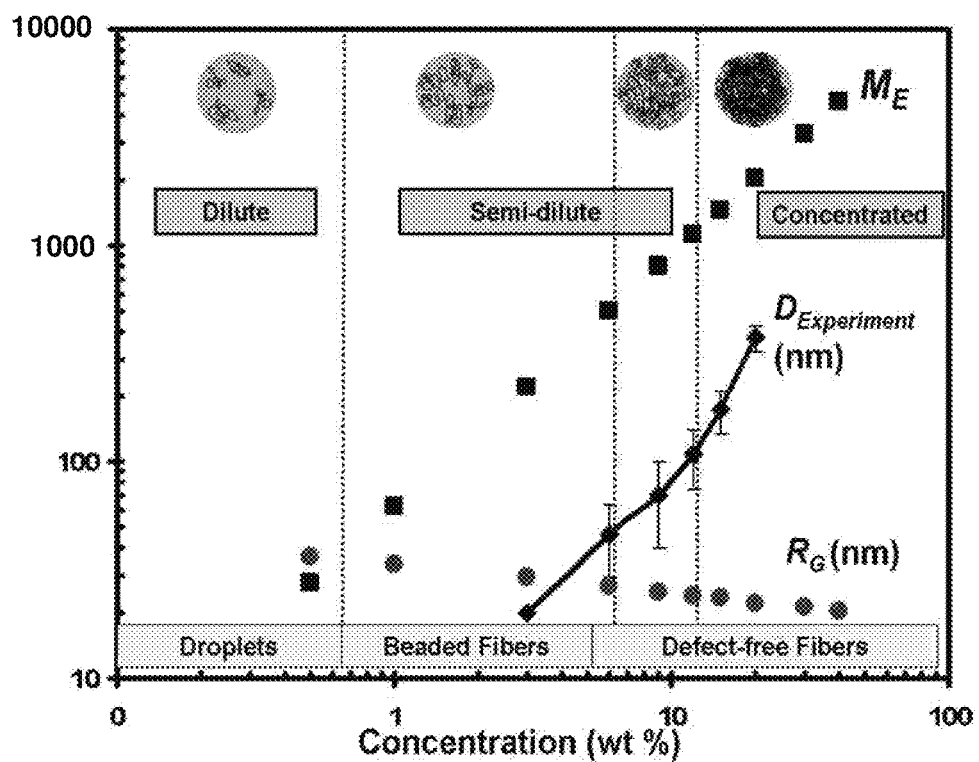
Figure 10:
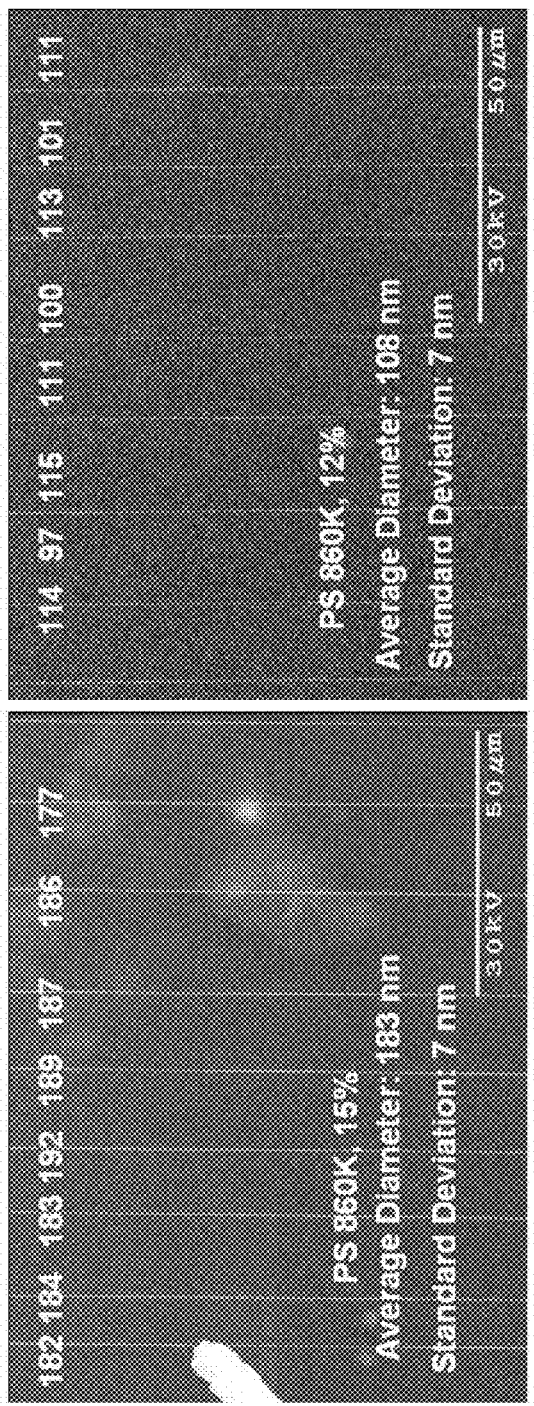
FIGS. 10A-C are scanning electron micrographs showing the repeatability of the fiber fabrication technique at different concentrations of PS 860K.
Figure 10:
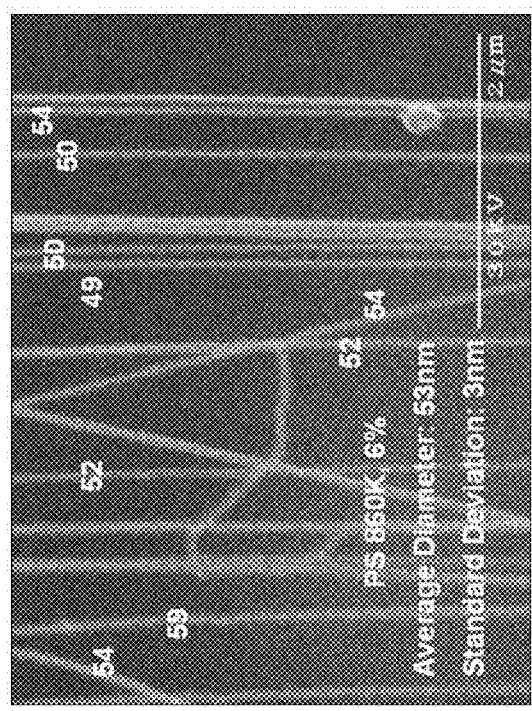
Figure 11:
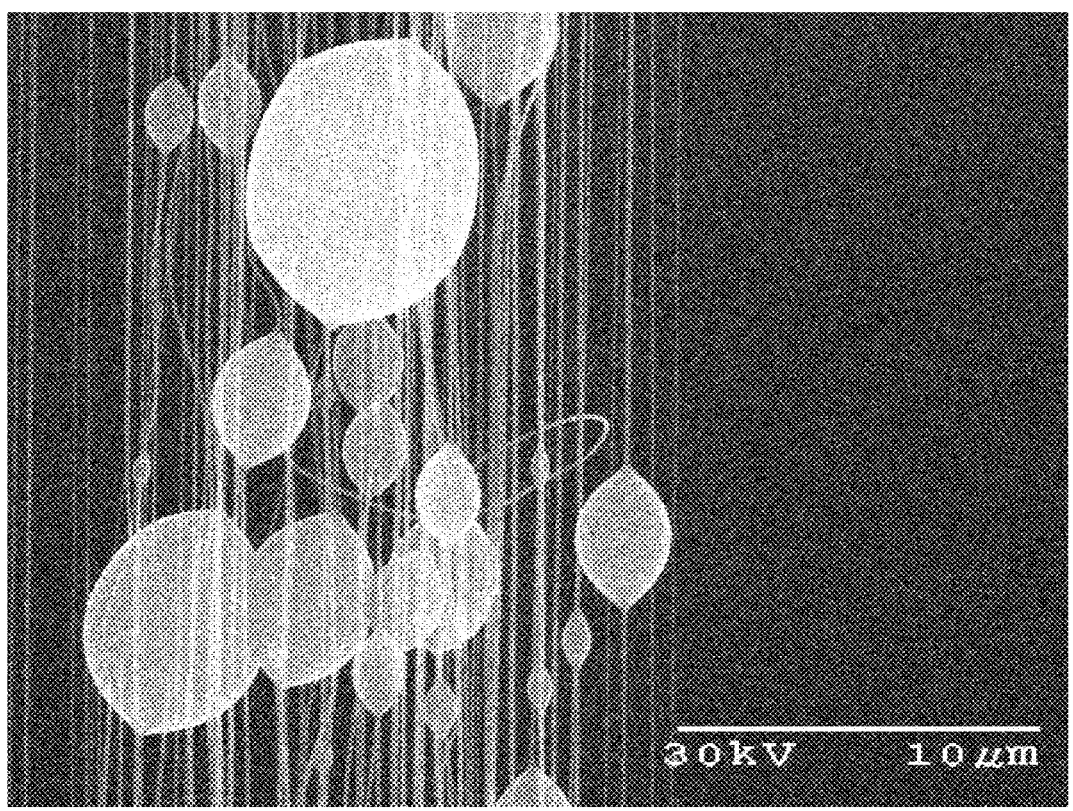
FIG. 11 is a scanning electron micrograph showing beaded fibers formed at low concentrations.

In this example, the first material parameter to be controlled is the solution concentration. The effects of the control of this material parameter can be observed from the following example: PS 860K (gm/mol) polymer was dissolved in xylene in concentrations ranging from semi-dilute unentangled to concentrated as shown on the master curve of GD (FIG. 9A). Fibers were deposited on planar geometries (FIG. 7A at 550 rpm. The chosen concentrations provide insights in the design workspace, as a marked decrease in the fiber diameter was obtained with decreasing the concentration. At below the 6% concentration (semi-dilute unentangled) regime, beaded fibers were observed to form with a mix of diameters. Additionally, these fibers could not be pulled over several millimeters in length without beaded structures. The fiber diameter ranges from sub 50 nm to 500 nm by varying the concentration of the polymer solution as shown in FIG. 9B. Higher concentration polymer solutions in the semi-dilute entangled and concentrated regimes do not have sufficient solvent to allow for partial chain elongations, and lock down process for fiber fabrication process occurs with rapid strain hardening. The exceptional repeatability attainable by the presented invention is shown in FIG. 10. At lower concentrations in the semi-dilute unentangled regimes, beaded fibers are formed as shown in FIG. 11.

Uniform fibers with no beads were observed at 6% and higher concentrations. This concentration lies on the border between semi-dilute unentangled and semi-dilute entangled regimes. $C_e$, the entanglement concentration is the boundary between semi-dilute unentangled and semi-dilute entangled concentration regimes and is defined as the point when significant entanglements of the polymer chains restrict the mobility of the individual polymer chains. Following the procedure outlined for developing scaling relationships for electrospinning fibers, the concentrations were normalized by the critical chain overlap concentration (C*) [McKee M. et al., Macromolecules. 2004; 37:1760; Gupta P, et al. Polymer. 2005; 46:4799]. Defect-free fibers started forming around 6% concentration, suggesting that $C_e$ scaled as C/C*~10, which is in agreement with the master curve of GD. Additionally, plotting the diameter as a function of normalized concentration provides scaling law for fabricating defect-free fibers ranging from 50 nm to 500 nm. The scaling law (FIG. 12):

$$\text{Fiber Diameter} \sim (C/C^*)^{1.5-1.6} \text{ Fiber Diameter} \sim (C/C_e)^{1.5-1.6} \quad (5)$$

shows a weaker dependence as compared to the electrospinning studies ([McKee M. et al., Macromolecules. 2004; 37:1760] (2.6) and [Gupta P, et al. Polymer. 2005; 46:4799] (3.1)). The scaling law is unique to the process described herein and is for a higher molecular weight species compared to the other studies. Detailed studies in the future will allow for establishing scaling laws for fiber fabrication of various polymeric systems using the fabrication technique presented herein. The fabrication technique is robust, repeatable and deposits fibers with high accuracy in the design workspace of the fiber solution concentrations.

Figure 13A:
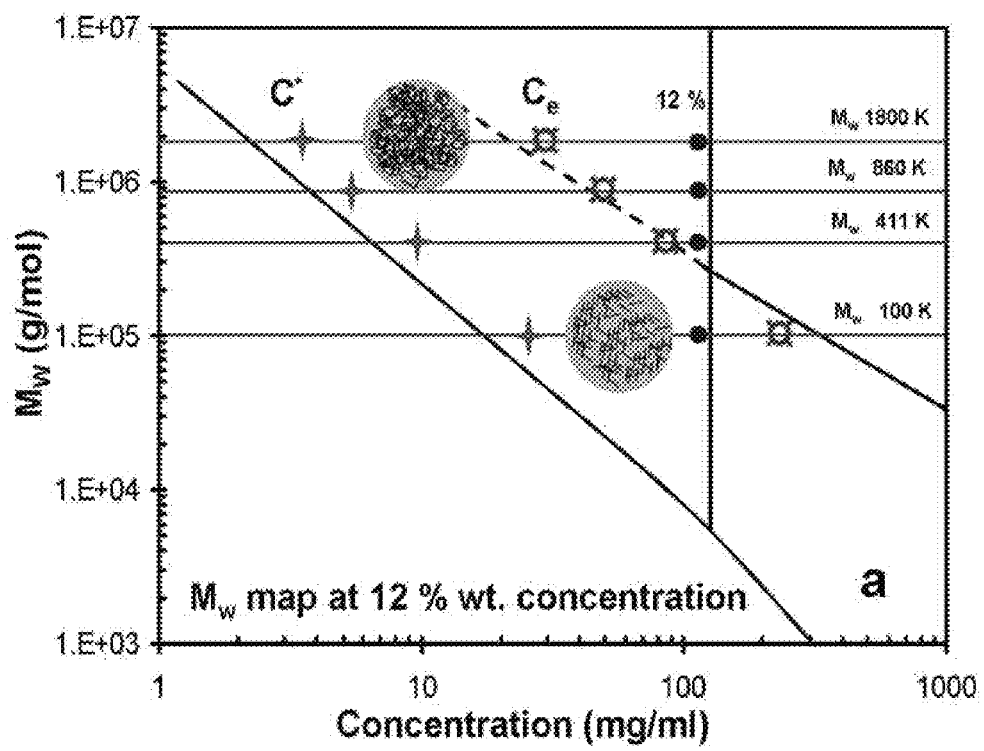
FIGS. 13A-13B are graphs showing (A) four different molecular weights at 12% wt. concentration with respective critical overlap (C*) and molecular entanglement concentrations ($C_e$); and (B) diameter variation with molecular weight. Data was averaged over 40 fibers) and 100K sample produced beaded fibers.
Figure 13B:
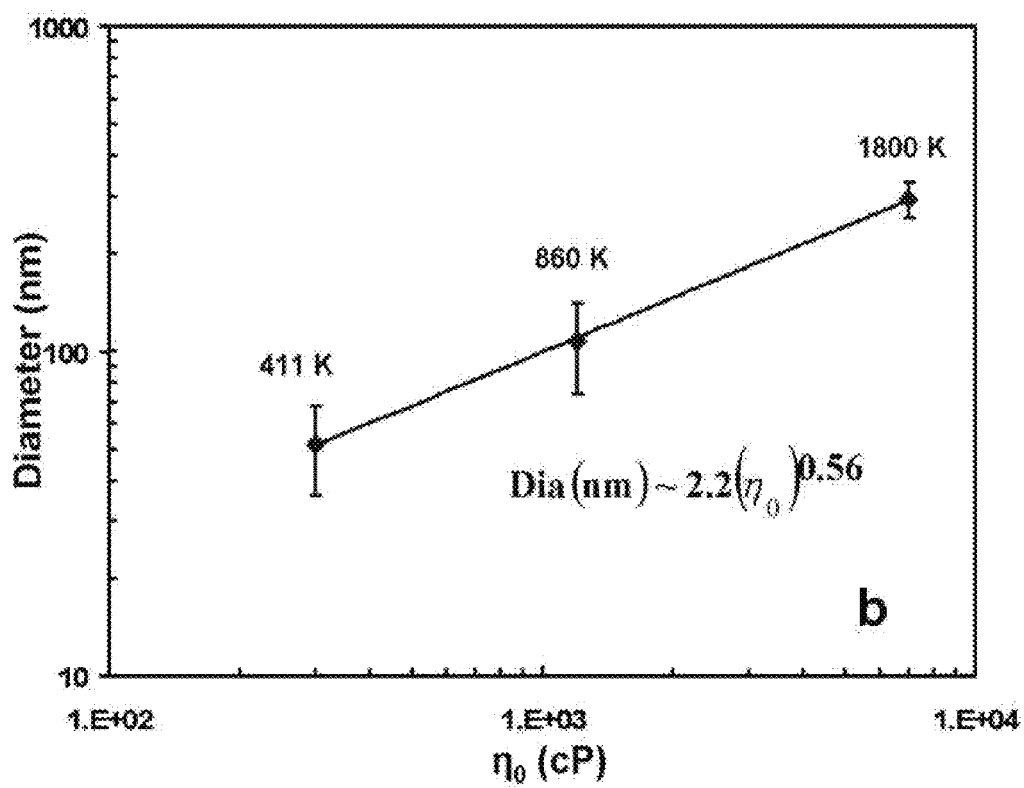

In this example, the second material parameter to be controlled is the molecular weight of the polymer species at a constant concentration. The effects of the control of this material parameter can be observed from the following examples. Four different molecular weight (100, 400, 860 and 1800K (gm/mol) of PS) solutions were prepared 12% by weight in xylene and mapped on the master curve of GD as shown in FIG. 13A. The diameter of fibers at constant rotational speed decreases with the decrease in molecular weight (FIG. 13B). 400, 860 and 1800K molecular weights at 12% concentration lie within the semi-dilute entangled regimes and 100K (gm/mol) is in the semi-dilute unentangled regime. Even though the chosen concentration of 12%, puts them close to the concentrated regime, beaded fibers were observed for 100K (gm/mol), thus suggesting that semi-dilute entangled domain is preferred for fabricating nanofibers. Higher molecular weight polymer chains having a higher density of entanglements compared to lower molecular weights at the same concentration can resist the shear deformation of the solvent molecules, thus leading to bigger diameter fibers.

This leads to the design criteria that a higher molecular weight polymer species at reduced concentrations and a lower molecular weight polymer species at increased concentrations can provide a platform for equaling the entanglements in the system, which can then lead to similar diameter fibers. The following experimental data support this approach: PS860K 15% concentration was chosen as model solution (Table 2).

TABLE 2

PS 860K solution concentrations and C/C* values

| Solution(%) | C (mg/ml) | C/C* |
|---|---|---|
| 1.00 | 8.74 | 1.59 |
| 3.00 | 26.75 | 4.87 |
| 6.00 | 55.21 | 10.05 |
| 9.00 | 85.55 | 15.57 |
| 12.00 | 117.95 | 21.47 |
| 15.00 | 152.65 | 27.78 |
| 20.00 | 216.25 | 39.35 |

The remainder molecular weight species (100K, 411K and 1800K (gm/mol)) were then formulated into polymer solutions in such a way that the ratio of C/C* of each species equaled that of the model solution (Table 3).

TABLE 3

Calculated concentration values of different molecular weights at same C/C*

| Mw (gm/mol) | C* (mg/ml) | C/C* | C (mg/ml) |
|---|---|---|---|
| 100000 | 25 | 27.79 | 694.75 |
| 411000 | 9.95 | 27.79 | 276.51 |
| 860000 | 5.49 | 27.79 | 152.57 |
| 1800000 | 3.45 | 27.79 | 95.88 |

Figure 14A:
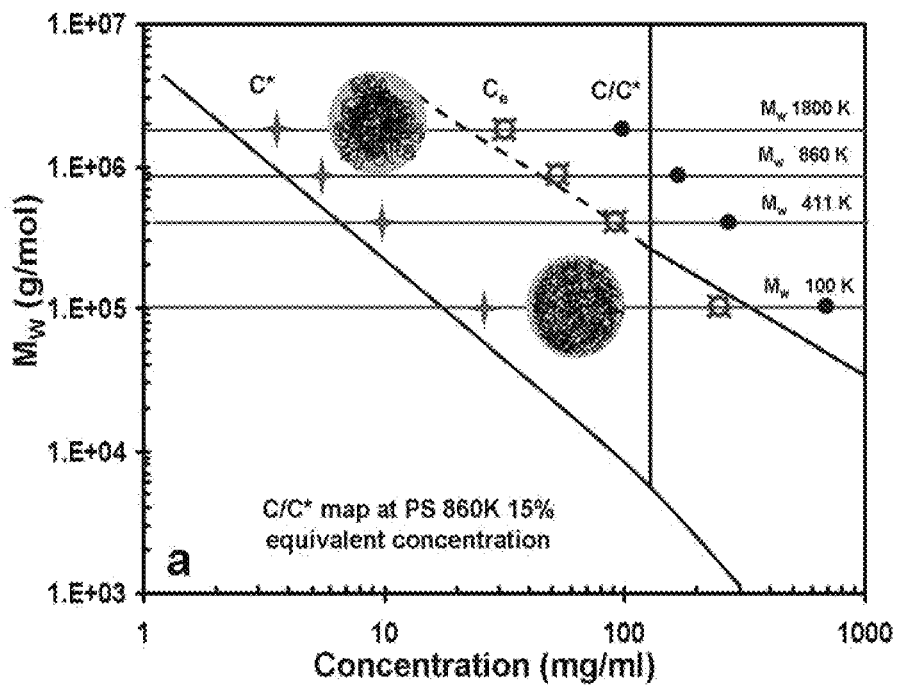
FIGS. 14A-14B are graphs showing (A) similar diameters of different molecular weights that were obtained by equilibrating entanglement concentration corresponding to the C/C* value for PS860K (g/mol) at 15% (wt) concentration. (B) The experimentally obtained equivalent diameters with the appropriate solution concentration (wt %) for the different molecular weights
Figure 14B:
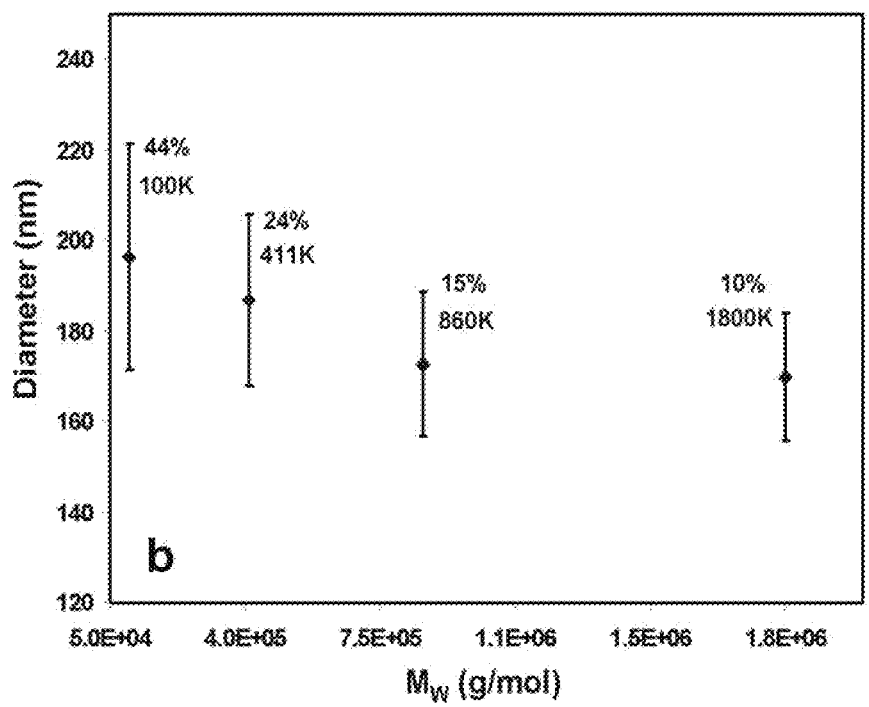

The obtained concentrations were then mapped on the master curve GD as shown in FIG. 14A. Fibers were deposited on planar geometries at constant rotational speed of 550 rpm and the experimentally obtained fiber diameters are shown in FIG. 14B. Thus, it is possible to deposit fibers of similar dimensions by increasing the entanglement density in low molecular weight species.

Design Workspace.

The fabrication of nano- and micro-fibers can greatly benefit if a design workspace encompassing different molecular weights and solution concentrations can be generated for depositing nanoscale fibers having diameters ranging from 50-500 nm and several millimeters in length. These high aspect ratio (length over diameter) fibers can then find useful applications and can be quickly integrated to develop novel technologies. Experiments as described above on fabricating fibers have shown the importance of several concentrations: dilute, semi-dilute unentangled, semi-dilute entangled and concentrated. The exact role of concentrated unentangled and entangled regimes in fabricating aforementioned fibers is partially understood and these concentrations become increasingly important for lower molecular weight species. Critical overlap concentration (C*) and the entanglement concentration ($C_e$) provide useful information on the design workspace for fabricating fibers. At C* the polymer chains are barely able to sustain entanglements, which does not allow fiber fabrication and at $C_e$ the onset of fiber fabrication is observed. At values lower than $C_e$ beaded fibers are obtained and at significantly higher concentrations than $C_e$ lock down of the polymer chains is observed due to absence of shear forces by solvent molecules, leading to bigger diameter fibers. Clearly, then the design workspace for fabricating fibers of desired dimensions involves identifying these concentrations for a given polymer of different molecular weights. The radius of gyration of a PS polymer chain can be calculated from equation 2 or can be estimated by [Heo Y & Larson R G, J Rheology, 2005; 49(5):1117]:

$$R_g = 0.012 M^{0.585} \text{ (nm)} \quad (6)$$

Figure 15A:
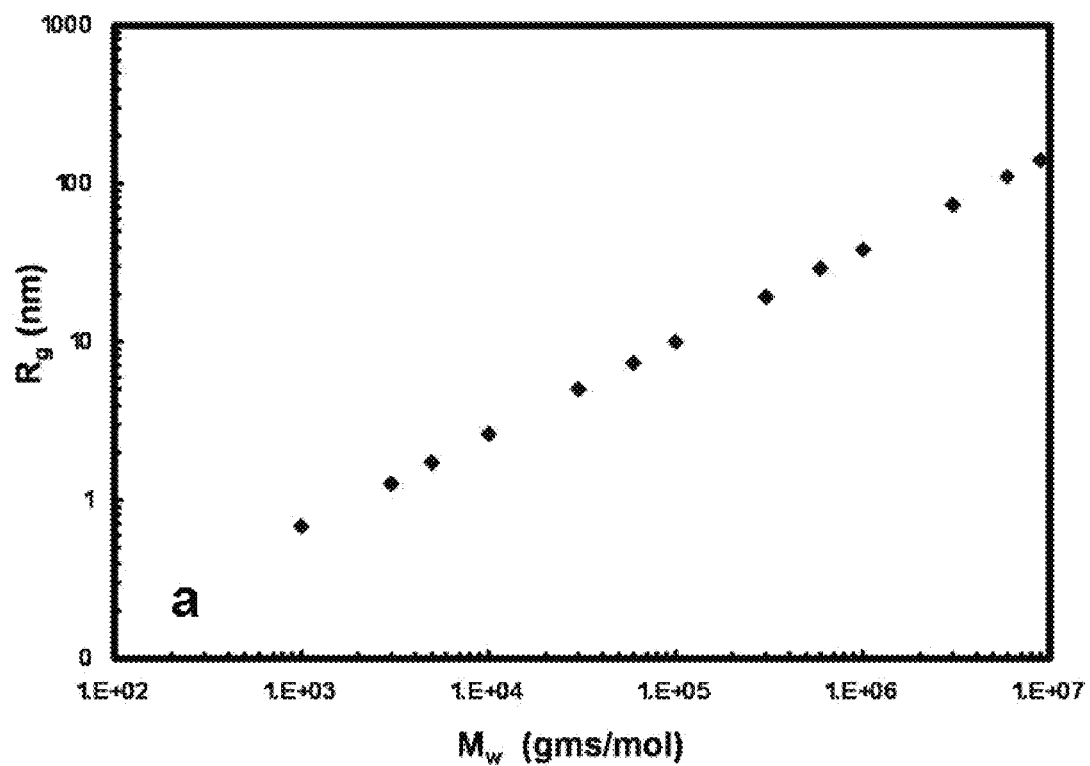
FIGS. 15A-15B are graphs showing (A) variation of Rg for different molecular weights at same dilution and (B) variation of Rg at given molecular weight for different dilutions showing fiber formation regions.

The radius of gyration increases with increasing molecular weight at the same dilution for a given polymer as shown in FIG. 15A. For a given polymer molecular weight, increase in solution concentration decreases $R_g$, with the extremes of highest radius in the dilute concentration regime and lowest unperturbed value in the melt (FIG. 9B). For good solvents, $R_g$ is defined as [Graessley W G, Polymeric liquids and networks: structure and properties, Garland Science, 2003]:

$$R_g^2(C) = R_g^2(o)(C/C^*)^{-1/4} \quad (7)$$

Figure 15B:
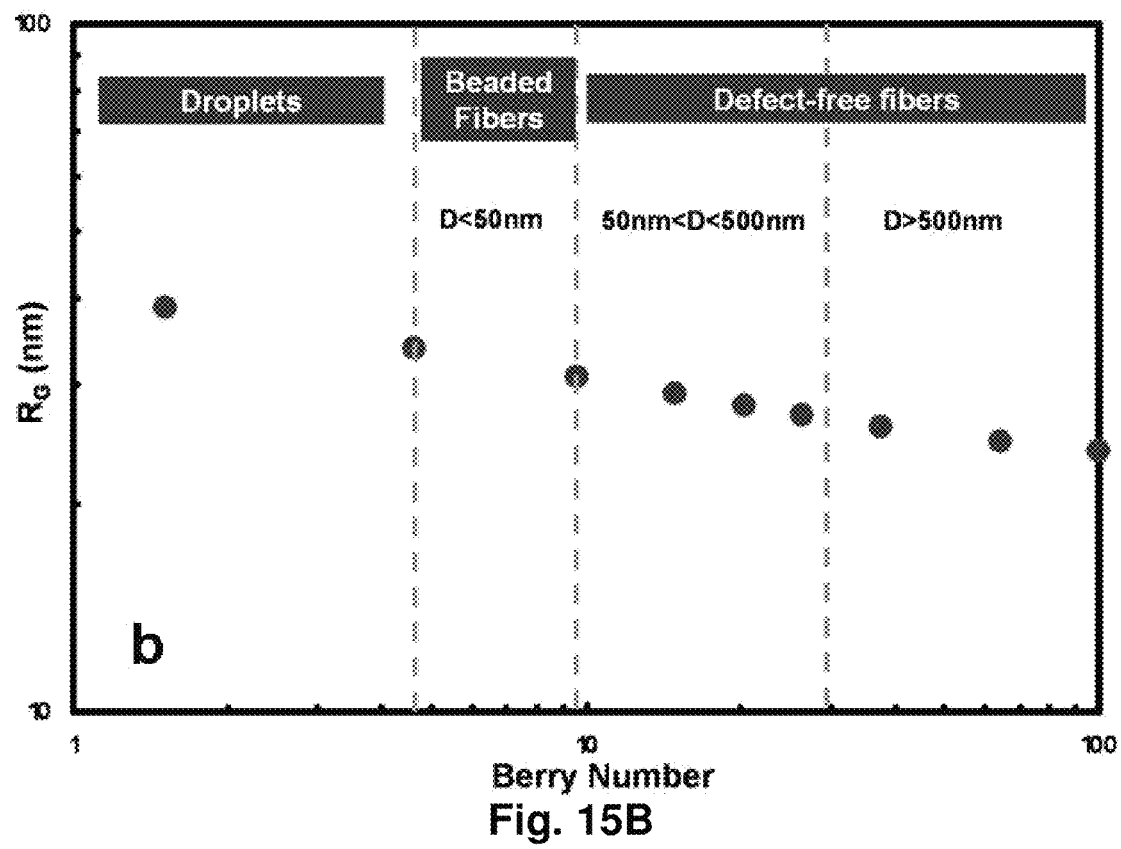

The decrease in radius at higher concentrations leads to higher number of entanglements and an early lock down in the fiber formation process giving rise to bigger diameter fibers. At moderately low concentrations, the shear force applied by solvent allows chains to partially disentangle, thereby forming smaller diameter fibers. At even smaller concentrations, absence of entanglements leads to breakup of solution volume into droplets and no fibers can be formed. A map for a given polymer molecular weight can then be generated as a function of dimensionless Berry number (product of C* and [η]), showing the possible regions of fiber formation along with the experimentally observed fiber diameter values (FIG. 15B).

Now, the entanglement concentration $C_e$ can be calculated as:

$$C_e = n_e^{(3v-1)}/M_w A_2 \quad (8)$$

where $n_e$ is the number of monomers between entanglements and is defined as $$n_e = M_e/m_o \quad (M_e = 13{,}309 \text{ gm/mol for PS}) \quad (9)$$

and v is the excluded volume exponent calculated as:

$$v = (a+1)/3 \quad (10)$$

with a being the Mark-Houwink-Sakurada constant obtained from dilute solution viscometry (0.69205) and $M_w A_2$ are calculated as:

$$C^* = \frac{5.3}{M_w A_2} \quad (11)$$

The calculated values of C* (from Mark-Houwink-Sakurada) and $C_e$ for PS-Xylene system are tabulated in Table 4. The calculated entanglement concentration value of 50.32 mg/ml of PS 860K (gm/mol) is in excellent agreement with the experimentally observed value of ~57 mg/ml (C*/C~10) where defect-free fibers are first observed. Thus, the calculated values of $C_e$ can be regarded as regions where defect-free nanofibers can be expected to form for PS for different molecular weights. This concept to a first approximation can then be mapped on the master curve GD along with C* values as shown in FIG. 4.

TABLE 4

C* and $C_e$ calculated for PS at different molecular weights to determine the design workspace

| Mw (gm/mol) | [η] (ml/mg) | C* (mg/ml) | Rg (nm) | MwA2 (ml/mg) | Ce (mg/ml) |
|---|---|---|---|---|---|
| 1000 | 0.002 | 617.04 | 0.68 | 0.01 | 5401.78 |
| 3000 | 0.003 | 288.48 | 1.29 | 0.02 | 2525.49 |
| 5000 | 0.005 | 202.58 | 1.74 | 0.03 | 1773.43 |
| 10000 | 0.008 | 125.39 | 2.60 | 0.04 | 1097.71 |
| 30000 | 0.017 | 58.62 | 4.95 | 0.09 | 513.21 |
| 60000 | 0.028 | 36.29 | 7.43 | 0.15 | 317.66 |
| 100000 | 0.039 | 25.48 | 10.01 | 0.21 | 223.07 |
| 300000 | 0.084 | 11.91 | 19.04 | 0.44 | 104.29 |
| 600000 | 0.136 | 7.37 | 28.56 | 0.72 | 64.55 |
| 860000 | 0.174 | 5.75 | 35.26 | 0.92 | 50.32 |
| 1000000 | 0.193 | 5.18 | 38.51 | 1.02 | 45.33 |
| 3000000 | 0.413 | 2.42 | 73.23 | 2.19 | 21.19 |
| 6000000 | 0.667 | 1.50 | 109.84 | 3.54 | 13.12 |
| 9000000 | 0.884 | 1.13 | 139.24 | 4.68 | 9.91 |

The mapping on the GD curve includes the points of previous experiments. The C* and $C_e$ predictions and experimental observations are in close agreement, thus confirming that this mapping can be utilized to a first approximation for determining the solution rheologies for nanoscale defect-free fibers using the fabrication technology described herein. As the molecular weight increases, lower concentrations would be required to form the desired fibers and conversely for smaller molecular weights, very high concentrations would be required. At very low molecular weights, the solution concentrations would have to be in the concentrated regime to be able to form fibers and on the other limit at very high molecular weights semi-dilute unentangled regimes would form nanoscale fibers.

Figure 16A:
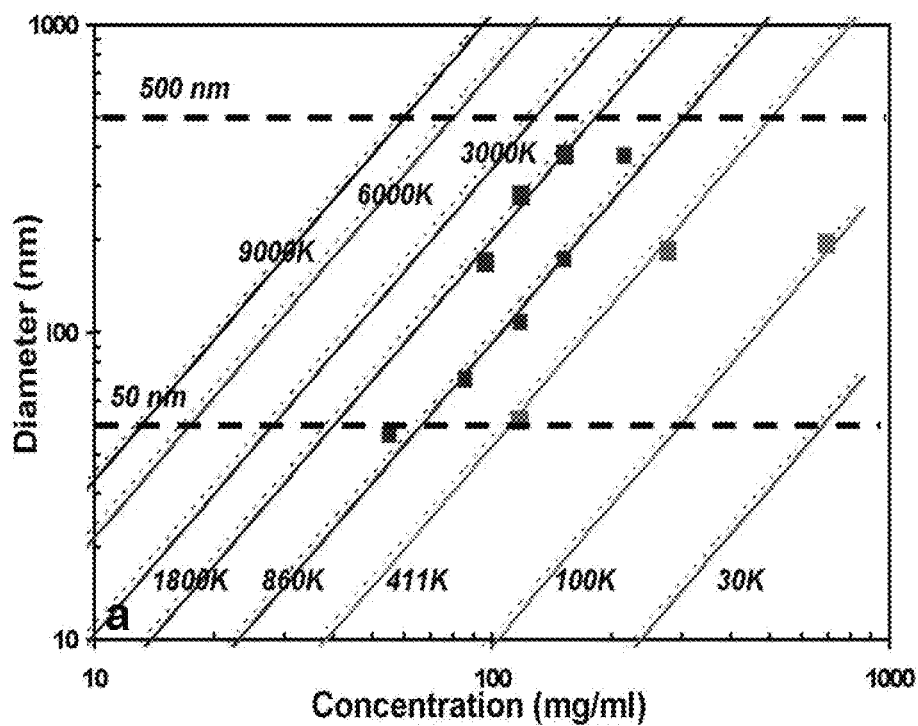
FIG. 16A-16B are graphs showing (A) predictions from scaling laws (see Equation 5, below) developed for critical concentration (bold lines) and critical entanglement concentration (dashed line) and superimposed with experimental results (squares) for different molecular weights; and (B) isodiameters ranging from 20-900 nm mapped on the design space. Shaded region signifies polymer deposition in the form of droplets or beaded fibers. Smooth, uniform diameter and defect-free fibers several millimeters in length are obtained at solution rheologies approaching $C_e$ shown by bold line.
Figure 16B:
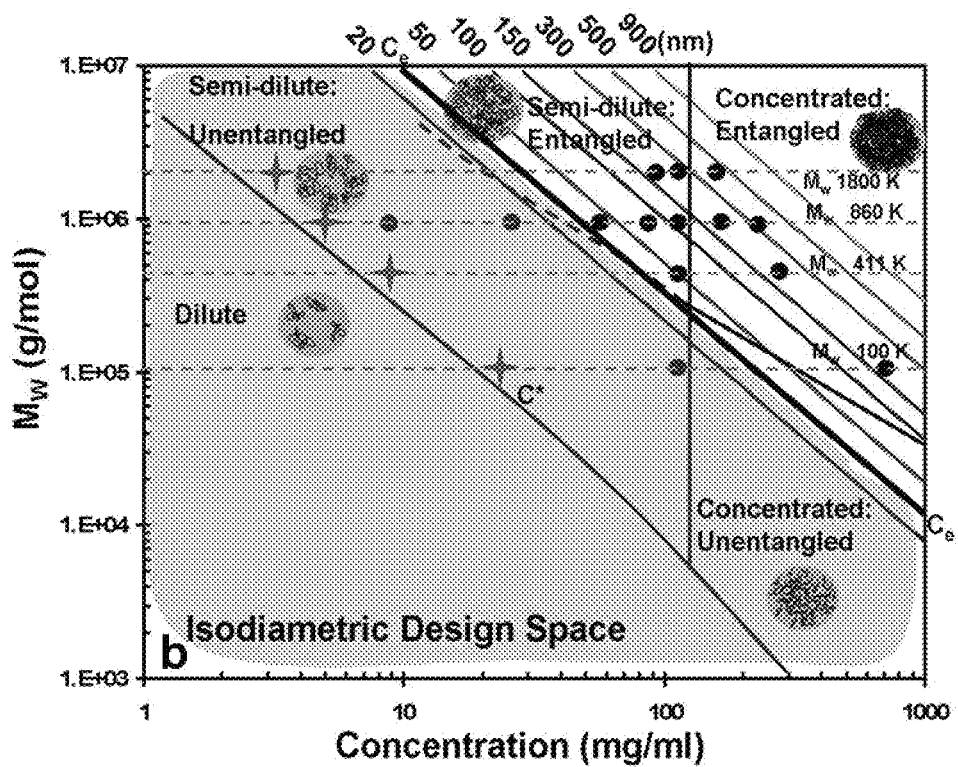

Scaling laws from equation (5) were used to determine the fiber diameters for several molecular weights at different concentrations and were found to be in agreement with experiments as shown in FIG. 16A. This lead to generating isodiameters spanning the entire solution rheological design space by using equations (1-11) as shown in FIG. 16B. Lower molecular weights require higher concentrations to achieve the desired entanglement density to form fibers and conversely higher molecular weights require lower concentrations to form smooth, defect-free, uniform diameter fibers having lengths of several millimeters. Predictions from the isodiametric design space clearly indicate that lower molecular weight species (10K and less) lack the ability to be employed for successful integration in nano-enabled technologies utilizing high aspect ratio (length/diameter) fibers. Thus, by visual inspection of the mapped design space, it is straightforward to determine regions of solution rheologies where fabrication of smooth, defect-free and uniform diameter fibers having lengths of several millimeters is expected. Deposition of polymeric material in the form of droplets or beaded fibers occurs within the shaded region bound by bold line of $C_e$ as shown in FIG. 16B. Additionally, by tracing the isodiameter contours it is possible to distinguish if fiber formation will occur at a given molecular weight. For example, the 20 nm isodiameter line clearly shows that fiber formation will not occur at all molecular weights, as it falls below the threshold $C_e$. Hence the isodiametric design space significantly compliments the polymeric nanomanufacturing platform for depositing aligned fiber arrays of desired dimensions and mechanical properties (molecular weights) in known locations.

Figure 17:
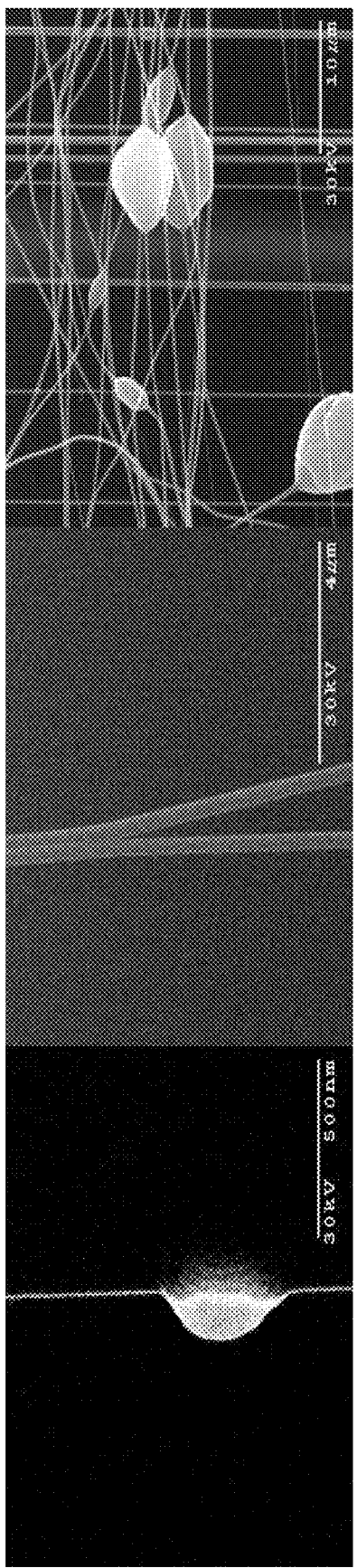
FIG. 17 shows scanning electron micrographs showing fibers fabricated with (left) sub 20 nm diameter; (middle) merging of such sub 20 nm fibers, and (right) fiber deposition in layers.

At very low dilutions, beaded fibers having diameters approaching less than 20 nm are possible. The fiber diameters which can be fabricated as described herein have been shown to be in the sub 20 nm range as shown in FIG. 17 (left). Other problems associated with fibers of this scale are the geometrical spacing between the fibers and the survivability. Sub 30 nm fibers are prone to breakage under current measurement techniques and also fuse with the neighboring fibers, which makes it difficult to get an accurate measurement of the fiber diameter as shown in FIG. 17 (middle). Survivability of such fibers can be increased by fiber deposition in layers (which can be sacrificial) as shown in FIG. 17 (right).

Figure 18:
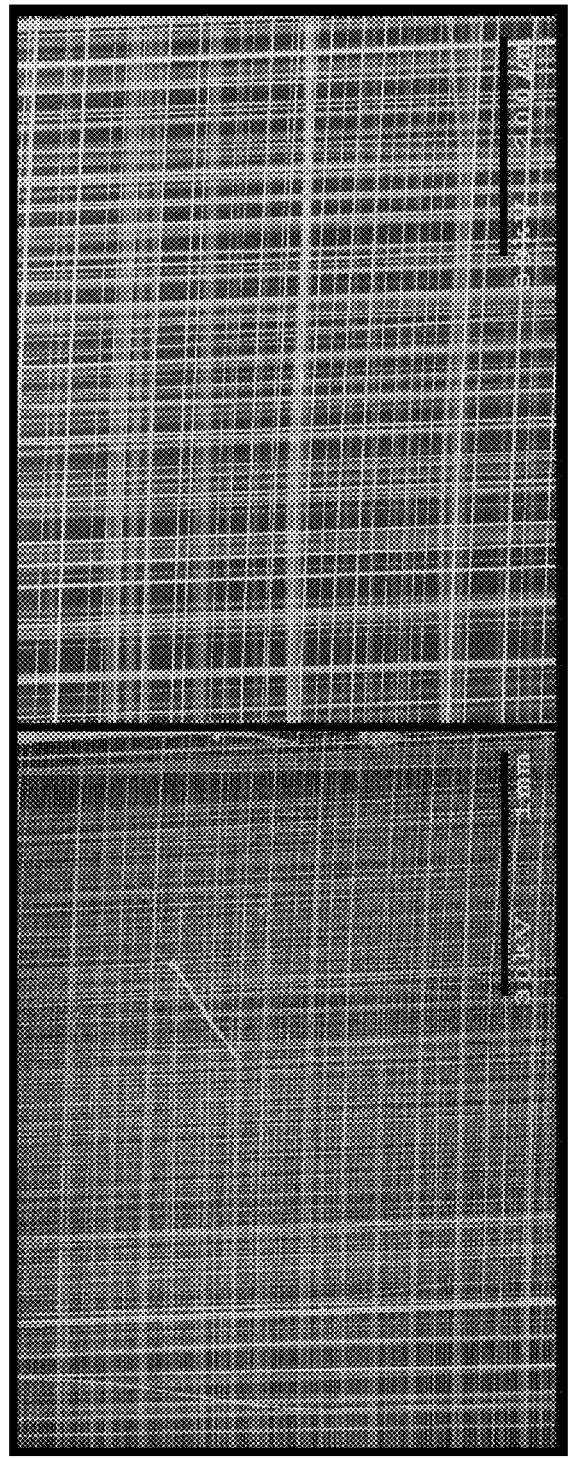
FIG. 18 shows scanning electron micrographs of highly aligned multi-layer fibers.

For any given molecular weight, looking at the design workspace, one can determine the concentration required to dry spin nanofibers in advance. The scaling laws obtained are the first ones to the best of our knowledge in depositing nanoscale fibers using dry spinning techniques and are envisioned to aid in developing nanoscale fiber deposition platforms. Scaling laws and design space for other polymeric systems follow from the approach described herein. Some of the applications enabled by using the fabrication technique include, but are not limited to making biomaterial scaffolds for tissue engineering, smart textiles, reinforcing material, sensors, filters etc. to name a few. In FIG. 18, the ability to deposit highly aligned multi-layer fibers, which can be used as filters, textiles, scaffolds or reinforcing material is demonstrated.

Example 3

Deposition of Particulates onto High Aspect Ratio Fibers

One goal of our product design is to functionalize the fibers with crushed activated carbon for use in filters. Activated carbon is a porous material that removes organic compounds from liquids and gases by a process known as "adsorption." In adsorption, organic molecules contained in a liquid or gas are attracted and bound to the surface of the pores of the activated carbon as the liquid or gas is passed through. Filters functionalized with activated carbon provide advantages over traditional filters by removing odors and hazardous gaseous vapors such as carbon monoxide and inorganic vapors in addition to traditional particulate matter.

Figure 19:
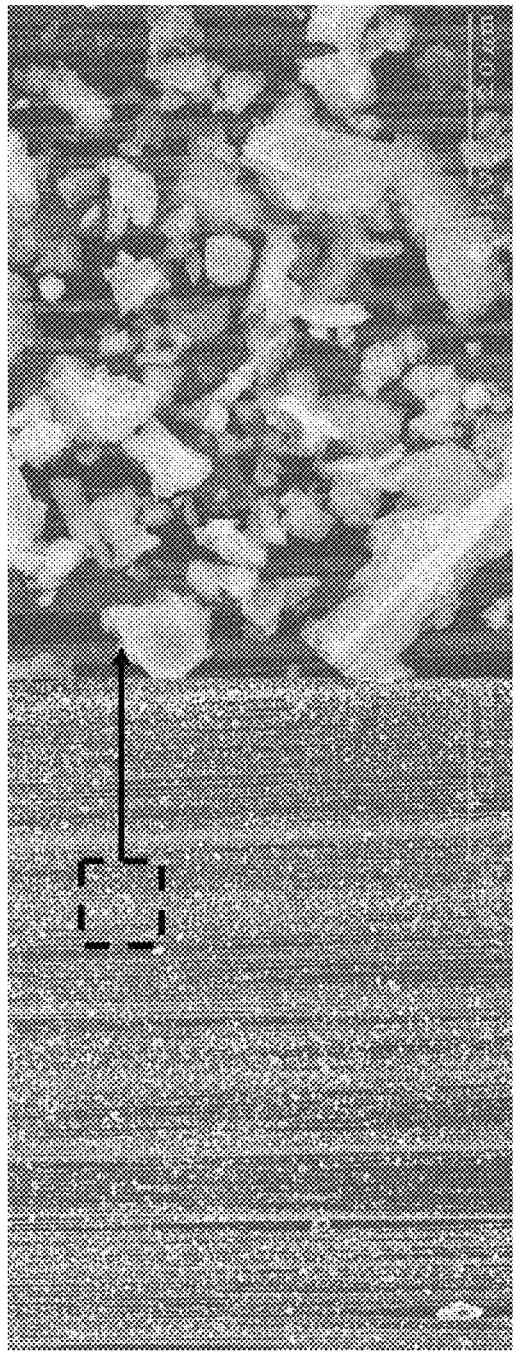
FIG. 19 shows scanning electron micrographs of fine particulate matter attached to aligned fibers.
Figure 20:
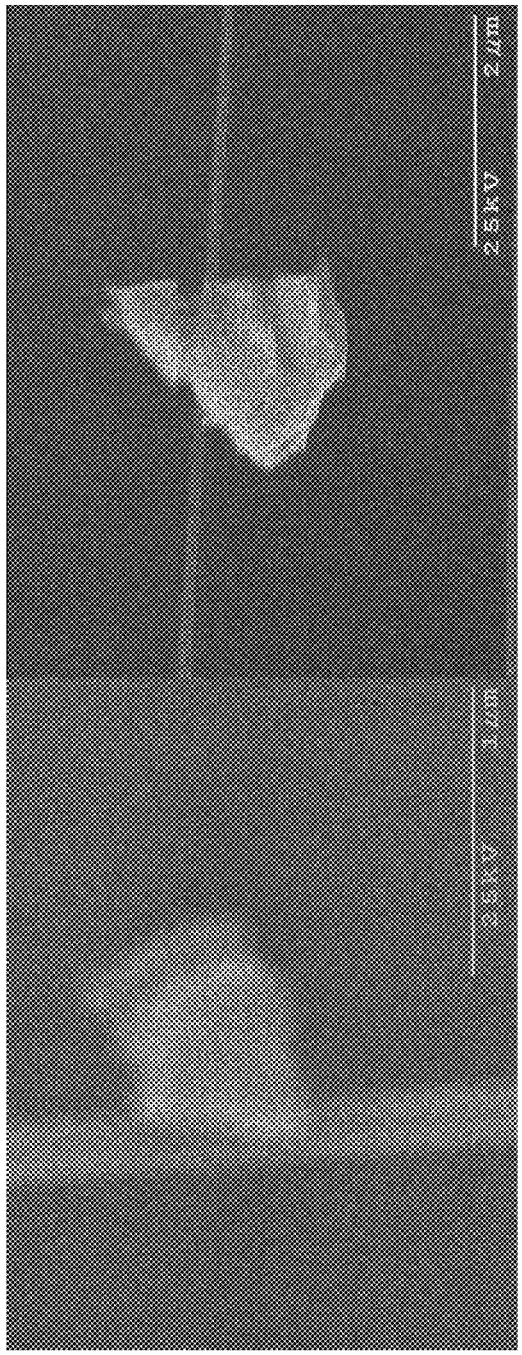
FIG. 20 shows scanning electron micrographs of fine particulate matter attached to a nanofiber.
Figure 21:
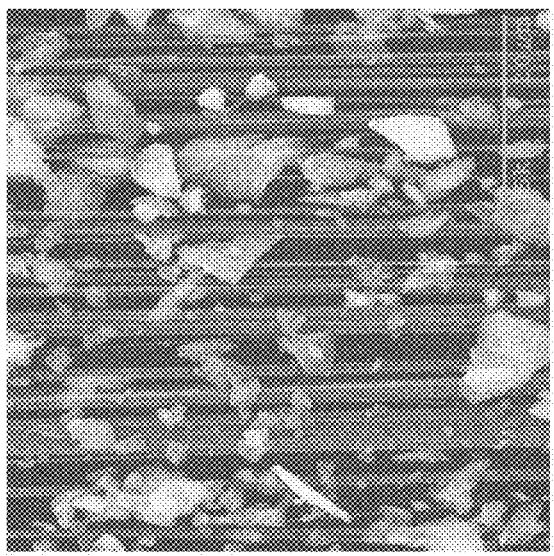
FIG. 21 shows scanning electron micrographs of different sized particles and in different densities attached to single layer aligned fibers.
Figure 21:
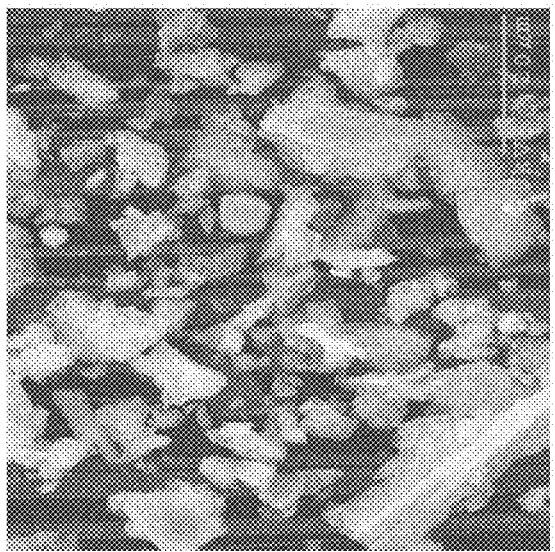
Figure 21:
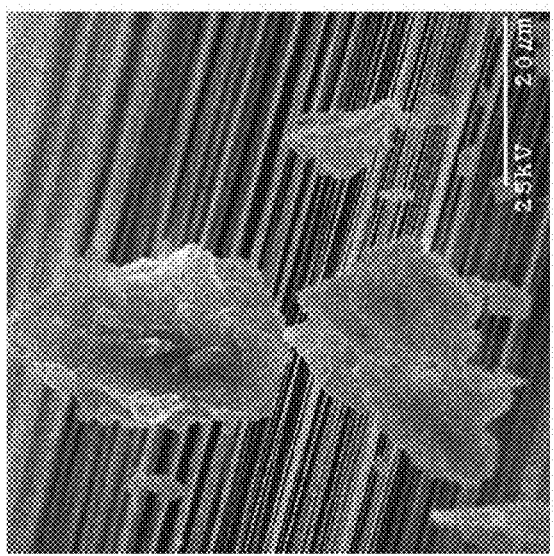
Figure 22:
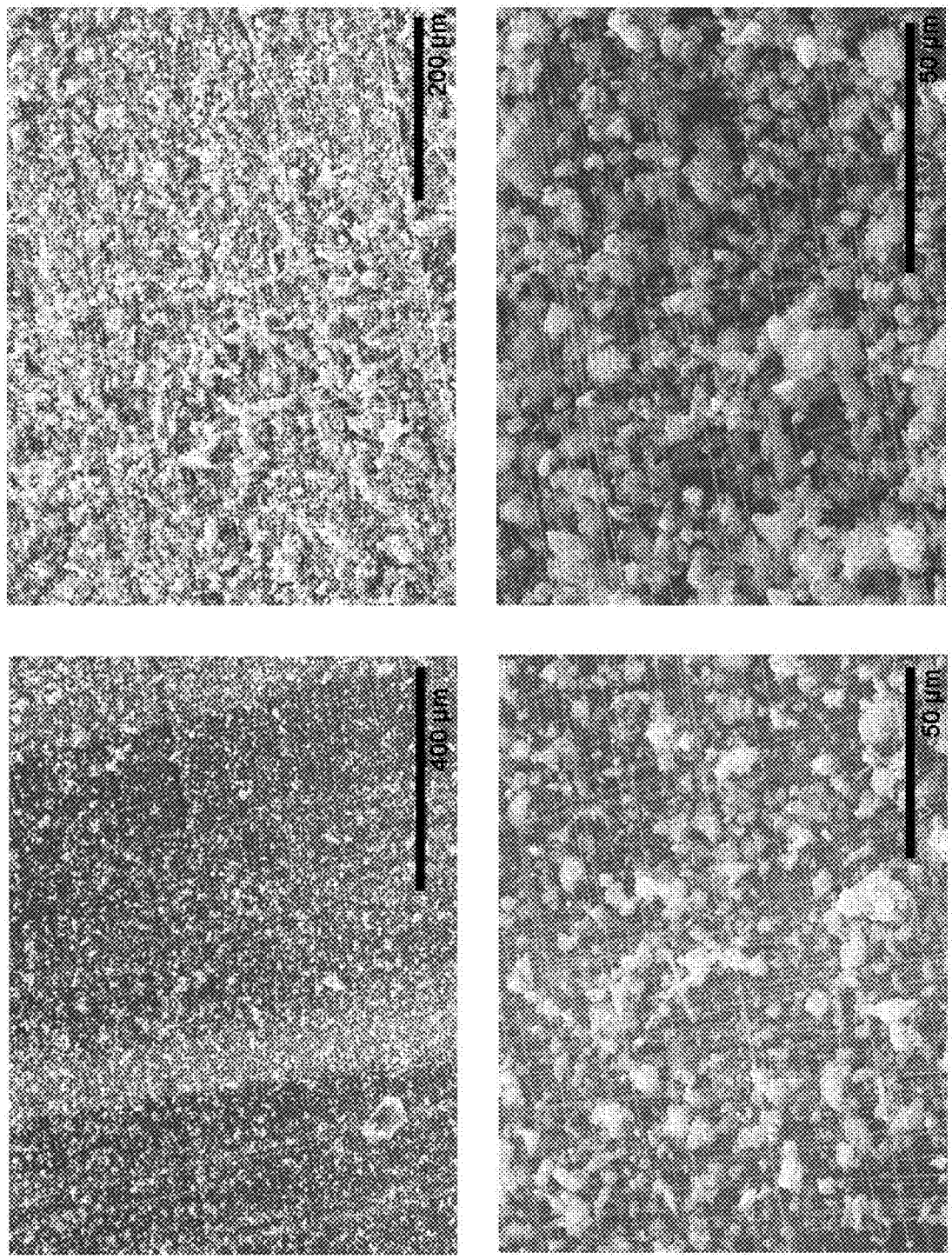
FIG. 22 shows scanning electron micrographs of different sized particles and in different densities attached to multi-layer aligned fibers.

Particles may be attached to the aligned fibers to achieve greater functionality. One example, without limiting the generality of the foregoing, is to attach activated carbon particles to the aligned fibers. The attachment of activated carbon particles, as shown in FIGS. 19-22, provides the aligned fiber constructs with the ability to serve as filters based on the pore size of the spacing between the fibers, and also to serve as filters based on adsorption of chemical species by the activated carbon particles. We strongly believe that by using our approach of distributing different sized particles with different densities (FIG. 21) can directly aid in the reduction of weight and size of the currently used functionalized filters. As shown in FIGS. 19-21, the particles can be attached to single layer aligned fibers, or as shown in FIG. 22, the particles can be attached to multi-layer aligned fibers.

Figure 23:
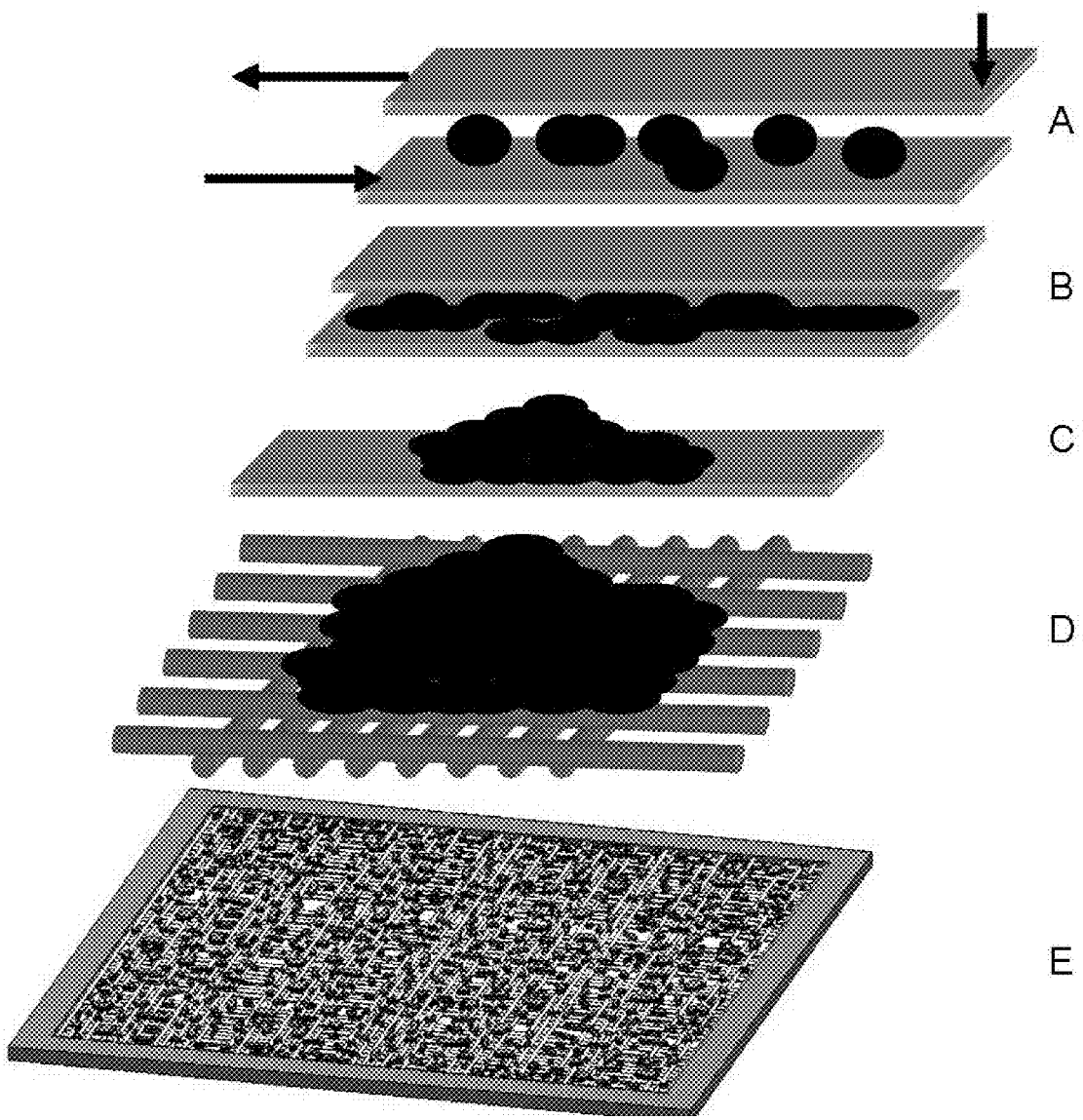
FIG. 23 is a schematic showing a non-limiting method of attaching particulate particles to the fibers: (A) coarse particulates are ground to a fine level using parallel plates, (B-C) fine particulates are collected in a heap, (D) heap is transferred to fibers and shaken to obtain fine particulate attachment to fibrous networks (E).
Figure 24:
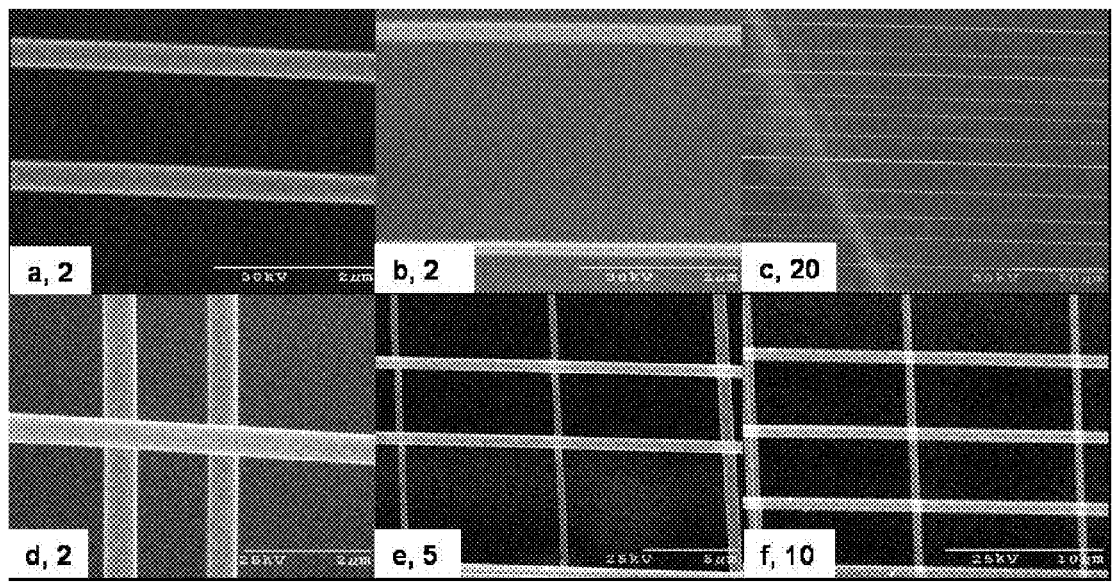
FIGS. 24A-24F show scanning electron micrographs of PS single (A-C) and double layered (D-F) fiber arrays at different fiber geometrical spacing. Individual scale bar markers in microns are indicated in each image for clarity.
Figure 25:
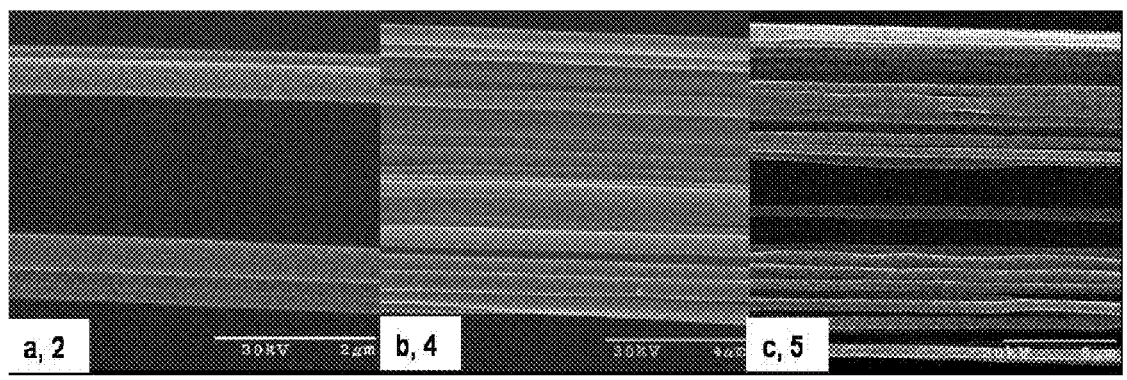
FIG. 25 shows scanning electron micrographs of PS tunable bundles of fibers deposited on a rotating substrate by varying angular and vertical linear speeds. Scale bar markers in microns are indicated in each image for clarity.
Figure 26:
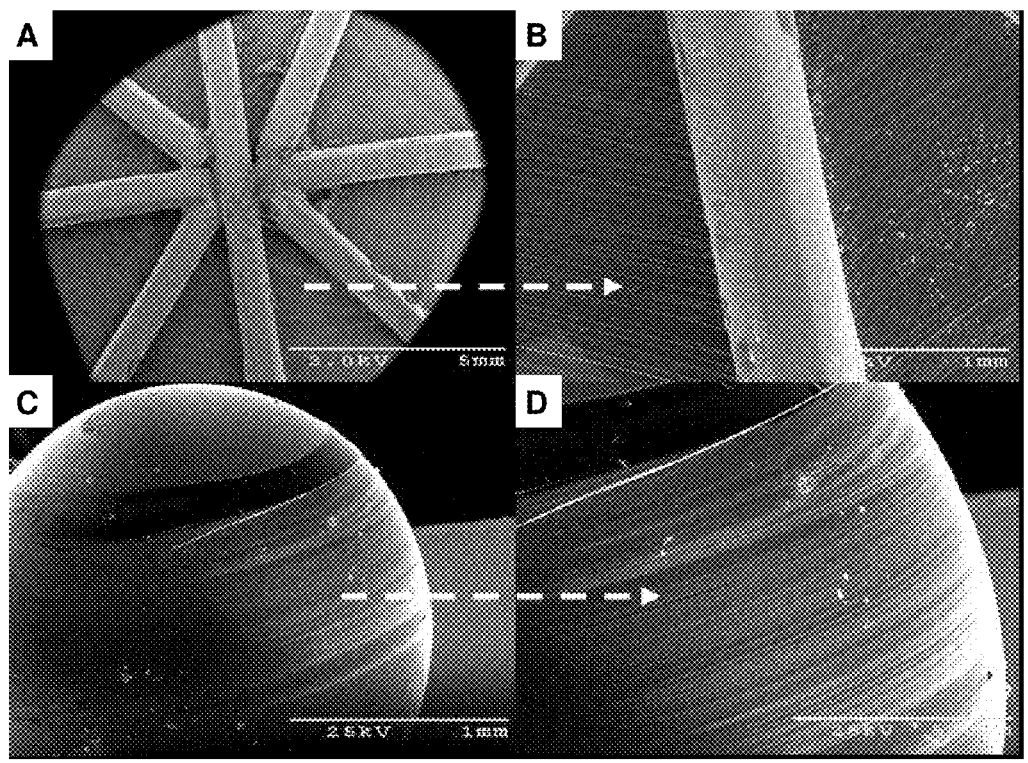
FIGS. 26A-26D show scanning electron micrographs of PS (A-B) dry spun spider web and PMMA (C-D) fibers dry spun on spherical geometries.
Figure 27:
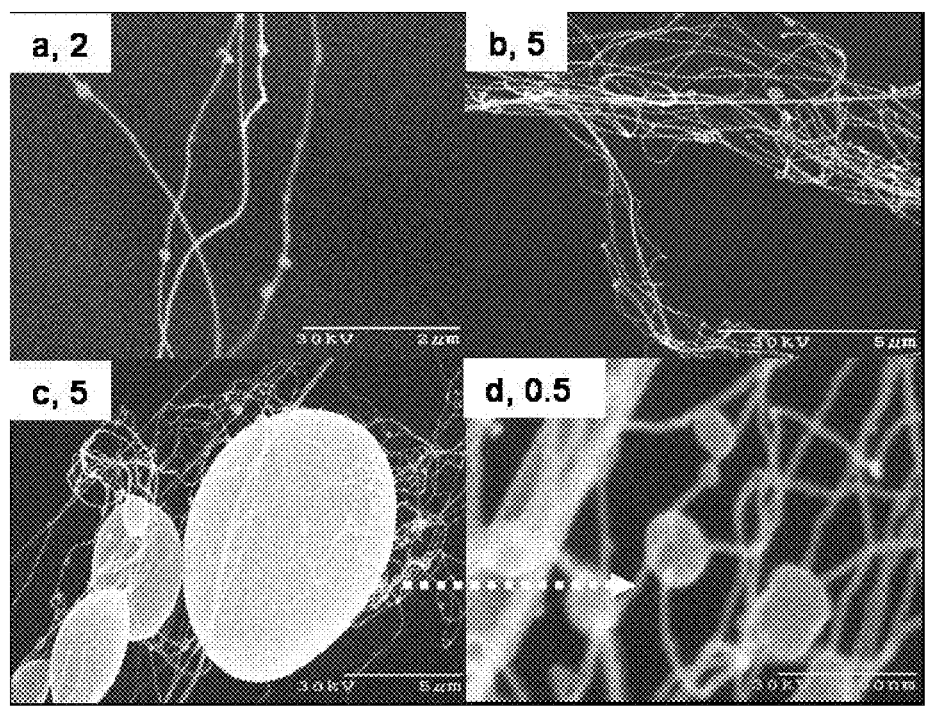
FIG. 27 shows scanning electron micrographs of beaded fibers, which collapsed during gold coating step prior to scanning electron microscopy imaging. Scale bar markers in microns are indicated in each image for clarity.
Figure 28:
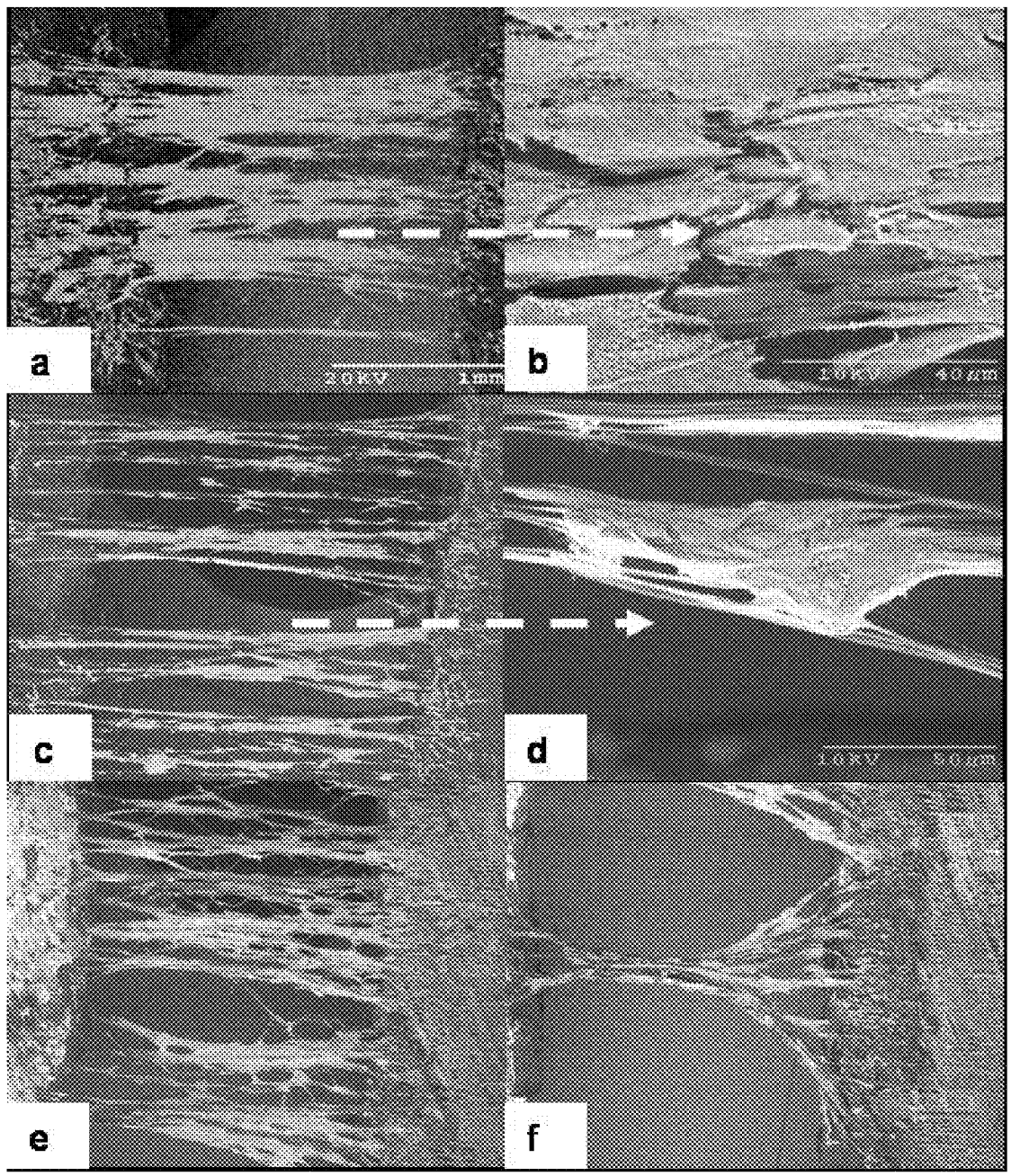
FIGS. 28A-28F show scanning electron micrographs of single layered tissue scaffolds seeded with mouse C2C12 cells demonstrating cell adhesion to fibers and cell alignment along the fiber axis for (A-B) PS and (C-D) PMMA, and (E-F) PLA.
Figure 29:
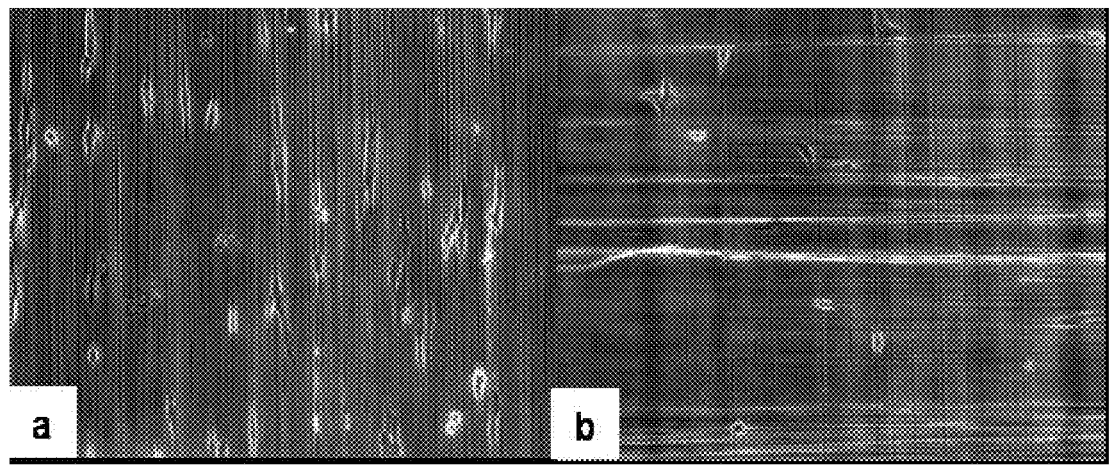
FIGS. 29A-29B show time lapse microscopy images demonstrating cell attachment, alignment and migration of mouse C2C12 cells on PS scaffolds of (A) a single layer and (B) double layers.
Figure 30:
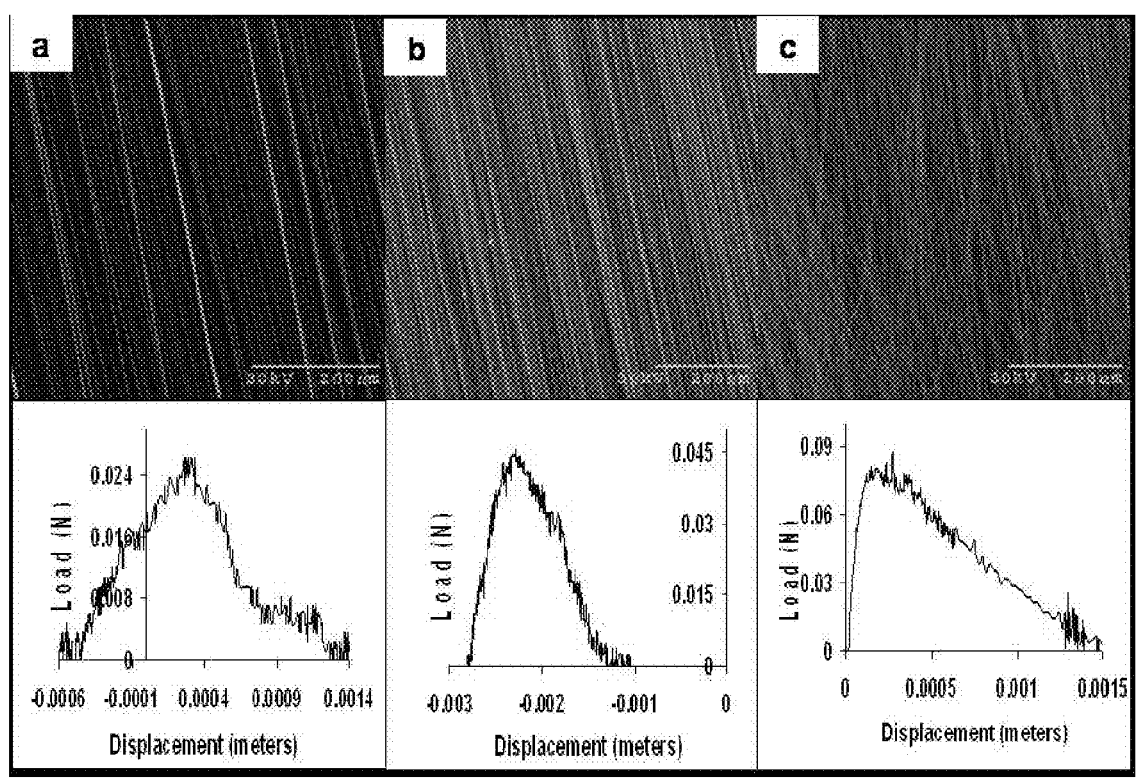
FIG. 30 shows scanning electron micrographs of PS fiber arrays as a function of increasing angular velocity from left to right showing decrease in array porosity (top row, scale bar 200 micrometers) and corresponding ultimate tensile strength of fibers (bottom row, left to right: 0.025N, 0.045 and 0.085 Newtons respectively.

A matrix of high aspect ratio fibers are prepared as described above. Powdered or comminuted activated carbon is then deposited onto the fiber matrix. In further detail, and in reference to FIG. 23, coarsely crushed activated carbon (Calgon) is further crushed to a fine particulate between two parallel glass plates (A and B). Arrows show the motion of parallel plates. Finely crushed calgon is then collected in a heap as shown in (C). The heap is then transferred to the fiber network (D), which is then mounted on a commercially available shaker (RPM~300) for 15 seconds to evenly distribute the activated carbon powder on the fiber surface as shown in (E).

The key advantages of this technique can be summarized as:

Control on fiber dimensions and alignment

Strong attractive forces generate strong adhesion between particulate and fiber networks Small feature size of particulate material increases its reactivity Deposition of particulate material in multiple layers in aligned configurations

Example 4

Dry Spinning Polymeric Nano/Microfiber Arrays Using Glass Micropipettes with Controlled Porosities and Fiber Diameters We present a method for dry spinning polymeric nano/microfiber arrays. In this technique polymer solution is continuously ejected from a stationary glass micropipette and the fibers are deposited as continuous arrays in parallel and complex geometrical configurations on a rotating substrate mounted on to a translation stage. As the polymer solution exits the glass micropipette, ambient air is used to evaporate the solvent, thus solidifying the fiber which is then deposited on the rotating substrate. For a given polymer, altering the processing and material parameters allows depositing fiber arrays with highly tunable porosities and uniform fiber diameters. The fiber array porosity is observed to decrease with increasing angular velocity of the rotating substrate at a constant translational stage velocity. Fiber array breaking strength experiments as a function of porosity show higher loads required to break low porosity arrays, which is critical in designing stronger materials. Additionally, single and double layered biological scaffolds fabricated using this technique are seeded with mouse C2C12 cells and cellular dynamics of adhesion, migration and proliferation is investigated.

In this example, we present a novel method of fabricating highly aligned single and multi dimensional fiber arrays with tunable porosities having uniform fiber diameters. Biomaterials based scaffolds for tissue engineering, nano/microfiber array textiles, novel sensors etc., are some of the applications that can be easily targeted using this technique. In this example, preliminary proof of concept experimental results on seeding biomaterial scaffolds with mouse C2C12 cells and a general approach for determining the force required to break an array of fibers are presented.

Dry spinning materials has been, and still is one of the most popular techniques for engineering fabrics. In this technique, a polymer dissolved in a solvent is extruded through a narrow orifice and the extruded filament forms a fiber by rapid evaporation of the solvent. In the proposed technique, polymer solution is pumped continuously through a glass micropipette, which is brought in contact with the rotating substrate. The rotating substrate stretches the extruded droplet, thus forming a cylindrical fiber by solvent evaporation in ambient atmosphere. The fabricated nano/microfibers are deposited in high densities as single or multi-layered fiber arrays.

Materials and Methods.

PS (Mw 1.8 million gms/mol, Pressure Chemicals, USA), PMMA (Mw 900 K gms/mol, Micro-Chem, USA) and Polylactic acid (PLA) (Mw 77,450 gms/mol, Sigma-Aldrich, USA) dissolved in xylene, chlorobenzene and chloroform respectively by 10% weight was ejected individually through the stationary glass micropipette mounted on to a manual XYZ stage as described above. Parallel configuration substrates attached to a DC motor are mounted on to a computer controlled XYZ nanopositioner (VP25-XA, Newport Inc.) and an optical microscope (Stemi SV 11, Carl Zeiss Inc.) is focused on the probe tip. A fiber optic light source is used to illuminate the setup.

Dry Spinning Fiber Configurations.

The proposed technique can be used to deposit aligned single or multi-layered nano/microfiber arrays at different geometrical spacing (porosity) as shown in FIG. 2. Different configurations of fibers serve different purposes in diverse applications ranging from filters to tissue engineering scaffolds. The two processing parameters for depositing fibers with tunable geometrical spacing are the angular velocity of the rotating substrate and linear vertical velocity of the translation stage. By keeping the vertical velocity constant and increasing the rotational speed, bundles of fibers can be deposited as shown in FIG. 3.

A distinct advantage of this technique is the ability to deposit aligned and uniform diameter fiber arrays in complex patterns, such as spider webs and spherical configurations, as shown in FIG. 4.

Material parameters such as molecular weight and viscosity of the polymer solution play key roles in depositing long uniform diameter fibers. The higher the molecular weight, the longer the fiber can be pulled due to presence of long individual polymer molecules in the polymer solution. Viscosity on the other hand, provides a network of entanglements, which can be regarded as 'short and long range' at higher and lower concentrations of the solvent in the polymer solution respectively. The polymer concentration in the extruded droplet from the glass micropipette increases due to solvent evaporation. This can be viewed as transformation from short to long range entanglements of a given polymer chain in the system. In the long range entanglement network, a given chain has sufficiently large number of points where it encounters entanglements with other chains in the system, thus greatly reducing the mobility of chains and forming a solidified fiber. An initial high concentration of polymer in the spin dope leads to fibers having larger diameters and conversely a lower polymer concentration in the initial spin dope does not allow fiber formation, due to absence of entanglements. The minimum entanglement network sufficient to fabricate a fiber is observed with high solvent concentration dopes [Gupta P., et al. Electrospinning of linear homopolymers of poly(methyl methacrylate): exploring relationships between fiber formation, viscosity, molecular weight and concentration in a good solvent, Polymer. 2005; 46:4799-810; Boland E, et al. Tailoring tissue engineering scaffolds using electrostatic processing techniques: A study of poly(glycolic acid) electrospinning, J Macromol Sci-Pure Appl Chem. 2001; A38(12):1231-43], which tend to form beaded structures connected together with sub-100 nm fibers as shown in FIG. 5.

Biomaterial Tissue Scaffolds.

For regenerative medicine applications, we need to expand our understanding of the mechanisms by which nature assembles and functionalizes specialized complex tissues to form a complete organism. This involves understanding the underlying complex mechanisms of highly organized behavior spanning not only diverse scientific fields, but also nano, micro and macro length-scales. For example, an engineered fibrous biological scaffold possessing the hierarchal spatial properties of a native extracellular matrix (ECM) can serve as a building block upon which living cells are seeded for repair or regeneration. A native ECM consists of networks of fibers having diameters ranging from 50 to 500 nm and can be further divided into four distinct spatial hierarchal domains as: macro scale (>1 mm), micrometer scale (1 µm-1 mm), sub-micrometer scale (100 nm-1 µm) and finally nanoscale (<100 nm). Numerous studies have indicated the importance of key engineered parameters: fiber diameter [Flemming R, et al. Effects of synthetic micro- and nano-structured surfaces on cell behavior, Biomaterials. 1999; 20:573-88], fiber alignment [Zhong S, et al. An aligned nanofibrous collagen scaffold by electrospinning and its effects on in vitro fibroblast culture, J Biomed Mater Res A. 2006; 79:456-63; Xu J, et al. Microfabricated quill-type surface patterning tools for the creation of biological micro/nano arrays, Biomed Microdevices. 2004; 6:117-23], scaffold porosity [Pham Q, et al. Electrospinning of polymeric nanofibers for tissue engineering applications: a review, Tissue Eng. 2006; 12:1197-211], fiber roughness [Thapa D, et al. Nano-structured polymers enhance bladder smooth muscle cell function, Biomaterials. 2003; 24:2915-26; Miller D, et al. Mechanism(s) of increased vascular cell adhesion on nanostructured pol(lactic-co-glycolic acid) films, J Biomed Mater Res A. 2005; 73:476-84] and topological constraints of scaffolds [Norman J & Desai T. Methods for fabrication of nanoscale topography for tissue engineering scaffolds, Ann Biomed Eng. 2006; 34:89-101]. The exact role of spatial dimensionality and if the hierarchal design criteria of a native ECM is fractal in nature are fundamental questions, which warrant a multi-disciplinary approach geared towards establishing an engineering framework for the design of one dimensional (1D) scaffolds for implantable devices or hierarchal assembly and shaping of these 1D blocks into three dimensional (3D) structures resembling a native organ for successful tissue engineering.

Electrospinning, phase separation and self-assembly are the three main methods employed currently to produce fibrous biological scaffolds for tissue engineering. However, these versatile techniques lack the ability to deposit oriented consistent diameter fibers in pre-determined configurations. In another similar approach using micro glass pipettes, we have demonstrated successful adhesion and proliferation of mouse C2C12 cells on aligned scaffolds fabricated by sequential deposition of individual fibers [Nain A S, et al. Microrobotically fabricated biological scaffolds for tissue engineering. Proc of IEEE Int Conf. on Robotics and Automation (ICRA). 2007 April; 1918-23]. In the previous study, scaffolds were made out of PLA and the observed fiber diameters were in the micrometer range. Additionally, scaffolds had to be glued to the substrate to increase survivability and a minimum porosity of 8 microns was achieved.

The proposed technique in this study is able to deposit uniform diameter nano/microfibers with tunable porosity from sub 500 nm to micrometers as demonstrated in FIG. 2. Using the proposed technique, single and double-layered fibrous scaffolds were fabricated and seeded with mouse C2C12 cells. Cells readily attached to our engineered nano/microfiber scaffolds by forming multiple focal point adhesion complexes with the fibers and then over a period of seven to ten days fused into desired bundles as shown in FIG. 6. A key focus on developing this technology is the ability to provide a robust and repeatable platform which can be used for carrying out studies on cellular dynamics. This will enable generating a currently missing framework for the hierarchal design of fibrous scaffolds. For example, cells seeded on aligned single layered scaffolds, aligned themselves along the fiber axis and on double layered scaffolds were observed to make right angle transitions as shown by time lapse microscopy images taken over a 24 hour period in FIG. 7. The original cuboidal geometry of seeded cells was observed to change to an elongated morphology in single layer scaffolds, whereas in the double layered scaffolds, cells first migrated along a fiber in the elongated morphology, then changed back to cuboidal in the vicinity of a fiber intersection. Cells then started migrating on the perpendicularly intersecting fiber and once again assumed the elongated morphology. The exact mechanisms for such behavior are not yet clear, but it offers significant potential in designing scaffolds with a mix of fibers of engineered parameters and materials to achieve directed motion. The proof-of-concept of this study along with the preliminary observations of the effects of geometrical constraints on cell adhesion and migration opens new frontiers in designing specialty scaffolds.

Fiber Array Tensile Testing.

Nano/microfibers are of great importance and are continually finding new applications. With the reduction in fiber diameter, the number of defects decrease, which in turn imparts superior mechanical properties to fabrics composed of such fibers. Nano/microfibers, like other nanostructured materials tend to be cumbersome and delicate to fabricate, handle, and characterization of these structures introduces more complexities, which inevitably decreases their survivability. Current techniques for repeated fabrication of nano/microfibers having appropriate boundary conditions for characterization involve multiple processing steps. Fabricating, depositing and characterizing polymeric nano/microfibers is challenging in part due to the delicate nature of such materials and also due to the limitations in the existing techniques for fabricating and depositing aligned nanofibers with accurate boundary conditions.

Recently new techniques have been devised for measuring the strength of individual nano/microfibers [Tan E & Lim C. Novel approach to tensile testing of micro- and nanoscale fibers, Rev Scientific Inst. 2004; 75(8):2581-85; Guhados G, et al. Measurement of the elastic modulus of single bacterial cellulose fibers using atomic force microscopy, Langmuir. 2005; 21:6642-6] as traditional uniaxial tensile testing machines are not suitable for testing individual nano/microfibers. However, an array of aligned nano/microfibers acting as springs in parallel can be tested under a conventional/customized uniaxial tensile testing machine as shown in FIG. 8B. Fiber arrays shown in FIG. 8B were clamped in an Instron uniaxial tensile testing machine and loaded at a constant speed until failure. It was found that the breaking strength increases with the decrease in array porosity, which suggests that this can be modeled as an array of springs in parallel and the individual fiber force can be determined by dividing the total force by the number of fibers.

In conclusion we present a novel technique for depositing highly aligned single and multi-layered nano/microfiber arrays using micro glass pipettes. This approach provides a unique and novel platform for benchmarking emerging nanotechnologies by the controlled deposition of uniform diameter fibers with tunable spacing between them, thus serving a broad range of applications. Preliminary proof-of-concept of demonstrating the control on geometry of deposited fibers, along with fabricating scaffolds for tissue engineering and fiber arrays for smart textiles has been demonstrated in this study. Tunable porosities ranging from nano to microscale, along with the capability of depositing fibers in bundles has been demonstrated. Flexibility in depositing fiber arrays in complex shapes and geometries of spider web and spherical objects respectively allow for extending this technique to novel applications. Scaffolds prepared for tissue engineering were successfully seeded with mouse C2C12 cells. Cell adhesion, migration and proliferation of seeded cells demonstrate the viability of this approach for fabricating tissue engineering scaffolds. Preliminary observations on topological constraints of fabricated scaffolds on cell migration provide a new gateway for establishing a general geometrical framework for building hierarchal biological scaffolds. By controlling the processing and material properties, the proposed technique enables fabrication of customized fiber arrays which can be used for fabricating smart textiles and composite materials. A strategy for testing fiber arrays using a commercially available tensile testing machine is presented in this invention.

Example 5

Dry Spinning Based Spinneret Based Tunable Engineered Parameters (STEP) Technique for Controlled and Aligned Deposition of Polymeric Nanofibers The experimental setup consists of a glass micropipette spinneret (diameter: 20-50 mm, Sutter Instruments) mounted perpendicularly to the substrate on a three degree of freedom manual stage (562 Series ULTRAlign™ Precision Multi-Axis Positioning Stages, Newport Inc., USA) as shown in FIG. 1A. The substrate in turn mounts on to a DC motor, which in turn gets mounted onto a motorized three degree of freedom micropositioning stage (VP-25XA, Newport, Inc., USA), Polystyrene (PS, molecular weight (Mw): 860 Kg mol$^{-1}$, Pressure Chemicals, USA) dissolved in Xylene with wt % concentrations ranging from 3-20%, PS (Mw: 1.8 million g mol$^{-1}$, Pressure Chemicals, USA) dissolved in Xylene at 15 wt %, and poly(methylacrylate) (PMMA: Mw 900 Kg mol$^{-1}$, Micro-Chem, USA) dissolved in Chlorobenzene at 9 wt % were used in this study. The viscous polymer solution was pumped continuously through the micropipette spinneret using a syringe pump (Harvard Apparatus Inc., USA) at a flow rate of ~50-100 ml min 1. The fibers were collected on a substrate (5 mm in width) in aligned configurations spinning, at 550 RPM and above.

Multiple layers at desired orientations were fabricated by depositing fibers on top of previously deposited layer(s). Imaging of the deposited fibers was conducted after coating them with gold using a Pelco SC-6 sputter coater and examined using a Hitachi 2460N Scanning Electron Microscope. Digital images from the SEM were obtained using Quartz PCI Image management system software.

Result and Discussions.

STEP deposits polymeric nanofiber arrays in highly aligned configurations in single or multiple layers with variable geometrical spacing between them. The spinneret is brought in contact with the rotating substrate and retracted, thus stretching the extruded polymer solution volume and forming a solidified fiber by the rapid evaporation of the solvent. The solidified fiber is then collected continuously on the substrate in aligned configurations (parallel to the direction of tip) with user defined geometrical spacing (see FIG. 1A).

Fabrication and deposition of polymeric fibers constitutes a wide design space encompassing automation (processing) and material parameters. Automation parameters of angular speed of rotation ($\omega$) and vertical linear speed of translation (V) of the substrate coupled with the material rheological parameters of polymer solution concentration can be optimized to obtain fibers of desired dimensions distributed at tunable geometrical spacing. Fiber formation occurs after a series of complex transformations involving different concentration domains as schematically illustrated in FIG. 5. The process of fiber formation can start with the extruded polymer solution from the glass micropipette spinneret making contact with a substrate in any of the initial polymer concentration domains. The initial starting concentration of the polymer solution in the dilute to semi-dilute concentrations allows solvation of polymer molecules in a good solvent. For lower molecular weight species at high concentrations in a solvent or higher molecular weight species dissolved at lower concentrations, the polymer molecule can be considered surrounded in a sea of solvent molecules with the solvent molecules penetrating inside the polymer molecule (often referred as partially draining molecules) [Graessley W W, Polymeric liquids and networks: structure and properties, Garland Science, New York 2003].

The entanglement density at this stage (semi-dilute unentangled concentration domain) is not sufficient to restrict individual polymeric chain mobility undergoing a deformation field. The continual evaporation of solvent from the extruded polymer solution causes an increase in the entanglement density of polymeric chains, thus, reducing their overall mobility. This leads to a locked-down state of polymeric chains, which cause the entangled chains to strain harden and resist further deformation in the presence of deformation fields (FIG. 5 c, d) [Rothstein J P & McKinley G H. J. NonNewtonian Fluid Mech. 2002; 108:27-15]. A characteristic feature of the fiber formation process is the formation of the neck at the initial point of contact due to spreading of polymer solution on the substrate. This characteristic neck is observed to rapidly transition to a uniform one-dimension a cylindrical structure as shown by the scanning electron microscope (SEM) image in FIG. 5(e), thus, causing a continuous pull-out of fiber. In comparison with the dry spinning technique at macro length scales in which the entire extruded polymeric volume is wound up on the take up spool ater solvent evaporation, in the proposed STEP technique a single fiber is continuously pulled out of the ejected reservoir of polymer solvent solution at a given concentration. This causes the fiber formation process to be extremely difficult to image and visualize at the interface of the extruded polymer solvent volume and the fabricated fiber. Thus, any localized chain orientation effects and the length downstream from the extruded volume at which a completely solidified fiber is obtained remains to be determined.

Processing Parameters.

Nanofiber formation occurs by a locked down glassy state of entangled polymer chains in the concentrated polymer solution regime. Upon application of an external field, such as a velocity field, the solvent molecules perhaps apply a combination of shear and extensional forces on the polymeric chains causing possible local segmental elongation, similar to complete unraveling of single molecules in dilute solutions undergoing high strain deformations during coil stretch experiments (Larson R G. The structure and rheology of complex fluids, Oxford University Press, New York 1999). The higher the rotational speed, the larger the forces exerted by the solvent molecules on the polymer chains, leading to larger deformation of the chains, thus, resulting in smaller diameter fibers. However, the increased convective air transport at high rotational speeds causes lockdown to occur early, thus limiting the effect of ever increasing speed as shown in FIG. 8A.

The geometrical spacing between fibers can be directly controlled by varying the vertical translation speed of the motorized stage at a given rotational speed. PMMA fiber arrays with average fiber diameter of 350 nm were deposited on a non-planar spherical surface as shown in FIG. 8B. The effect of doubling the linear speed is demonstrated by the increase of the geometrical spacing between consecutive fibers deposited on the spherical substrates.

Material Parameters.

The material parameter investigated in this study is solution concentration for a fixed molecular weight. PS 860 K (g*mol$^{-1}$) polymer was dissolved in xylene in concentrations ranging from semi-dilute unentangled to concentrated (3, 6, 9, 12, 15 and 20% by weight) and mapped on the Graessley diagram (FIG. 9A) (Graessley W W. Polymer. 1980; 21:258). The solution concentrations were chosen after determining the critical overlap concentration ($C \approx 5.7$ mg·ml$^{-1}$) from dilute solution viscometry experiments of PS-xylene system (see previous examples). Fibers were deposited on planar geometries at 550 rpm corresponding to the constant diameter profiles obtained at high angular speeds of rotation (FIG. 8A).

The radius of gyration ($R_G$) of individual polymeric molecules along with the molecular entanglement density ($M_e$) of polymeric molecules at different concentrations provide insights in achieving control on the fiber diameter. $R_G$ for PS polymer molecules in dilute solutions can be approximately estimated as [Heo Y & Larson R G, J. Rheology. 2005; 49(5): 1117]

$$R_G(0) = 0.012 M^{0.585} \text{ (nm)} \tag{12}$$

where M is the molecular weight of the polymer. The change in $R_G$ with concentration can be estimated as [Graessley W W, Polymeric liquids and networks: structure and properties, Garland Science, New York 2003].

$$R_G^2(C) = R_G^2(0)(C/C^*)^{-1/4} \text{ (nm)} \tag{13}$$

where C and C* are the concentration of the polymer solution and critical overlap concentration, respectively. $R_G$ decreases with the increase in the polymer solution concentration (FIG. 9B), thus, making the polymer molecules more compact, which limits mobility of individual polymeric chain segments during fiber formation process.

The polymeric chain entanglement density as a function of concentration can be calculated as [Graham R S, et al. J Rheology. 2003; 47:1171]

$$M_e(c) = M_e c^\alpha \tag{14}$$

where $M_e$, the entanglement density of the melt (PS$\approx$13309 g·mol$^{-1}$) [Larson R G, The structure and rheology of complex fluids, Oxford University Press, New York 1999] and the scaling exponent, a ranges in values from $1 < a < 4/3$. The entanglement density increases sharply with the increase in the polymer solution concentration (FIG. 9B), which limits the mobility of individual molecular chains causing an early lock down glassy state at higher concentrations. Thus, the coupling effects of reduced $R_G$ and increased $M_e$ contribute to an increase in fiber diameter with increasing polymer solution concentration (FIG. 9B). Further, the entanglement concentration $C_e$ can be calculated as [Heo Y & Larson R G, J Rheology. 2005; 49(5): 1117]

$$C_e = \frac{n_e^{(3v-1)}}{M_w A_2} \tag{15}$$

where $n_e$ is the number of monomers between entanglements and is defined as $$n_e = \frac{M_e}{m_o} \tag{16}$$

and v is the excluded volume exponent calculated as $$v = (a+1)/3$$

with a being the Mark-Houwink-Sakurada constant obtained from dilute solution viscometry (0.69205) and $\overline{M}w\ A_2$ are calculated as $$C^* = \frac{5.3}{M_w A_2}. \tag{18}$$

The calculated entanglement concentration value of 50.32 mg·ml$^{-1}$ of PS 860 K (g·mol$^{-1}$) is in agreement with the experimentally observed value of $\approx$57 mg·ml$^{-1}$ (6 wt.-% concentration) where defect-free fibers are first observed. In our experiments (Table 5), at the lower limit of dilute concentrations, fibers could not be formed and polymer was deposited in the form of droplets. In the semidilute unentangled concentration domain, beaded fibers were observed to form with a mix of diameters and the beaded structures were found to be attached by sub-40 nm fibers, which could not be drawn over several millimeters in length. The onset of defect-free nanofibers characterized as smooth, uniform diameter and one-dimensional high aspect ratio repeatable fibers was observed around 6% solution concentration, which lies at the boundary of semidilute unentangled and semi-dilute entangled domains. For 3 and 25%, we did not perform error analysis, as fibers were nonuniform or greater than 500 nm in diameter, respectively.

TABLE 5

Experimentally observed fiber diameters as a function of polymer solution concentration for PS 860 K (g · mol$^{-1}$) dissolved in xylene.

| Concentration wt.-% | Diameter nm | Quality |
|---|---|---|
| 1 | — | Droplets |
| 3 | 20 | Beaded-Fibers |
| 6 | 46 ± 9 | Uniform Diameter |
| 9 | 69 ± 15 | Uniform Diameter |
| 12 | 107 ± 21 | Uniform Diameter |
| 15 | 172 ± 33 | Uniform Diameter |
| 20 | 375 ± 53 | Uniform Diameter |

Figure 31:
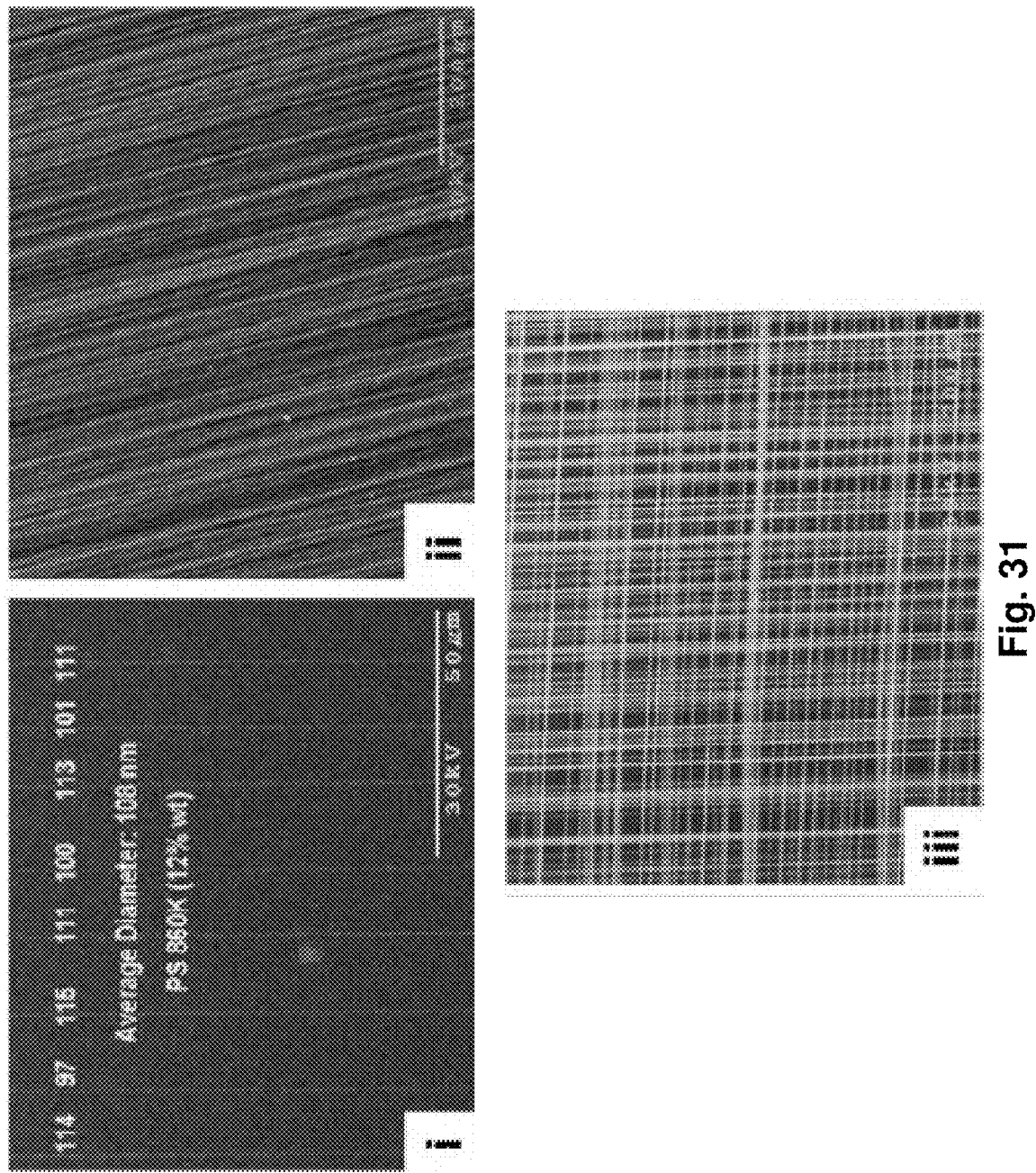
FIG. 31 shows scanning electron micrographs demonstrating the repeatability of the manufacturing platform for 860 K (g·mol-1) solution in single layer, (i) 12 wt. % concentration (average fiber diameter of 108 nm and numbers on each fiber show their measured diameters in nm), (ii) high alignment of fibers, and (iii) deposition of fibers in multiple layers.

This concentration commonly referred as entanglement concentration '$C_e$', corresponds to significant overlap of the polymer chains, thus constraining the chain motion undergoing elongational flows. In the concentrated polymer solution concentration domains beyond 20%, fibers with diameters in excess of 500 nm were obtained, which are not included in this study. The repeatability of the process in achieving control on fiber dimensions and alignment is demonstrated in FIG. 31 (i and ii). Further improvements in the experimental setup along with rigorous exploration of solution concentrations at the boundary of semi-dilute unentangled and entangled regions should facilitate fabrication of aligned defect-free sub-40 nm uniform diameter nanofiber arrays using the proposed process.

Thus, the developed framework in this study exploring the effects of processing parameters, different polymer solution concentrations. $R_G$, and $M_e$ on molecular chain local extensions and mobility can be extended to fabricate and precisely deposit other polymeric system nanofiber arrays. The potential applications targeted using the STEP technique are creating biomaterial scaffolds for tissue engineering, smart textiles, reinforcing materials, sensors, and actuators, which require fabricating precisely aligned and density controlled multi-layer structures. Multi-layer structures are fabricated in multiple steps with each additional layer of fibers deposited over the previous layer at user defined geometrical spacing and orientation as demonstrated in FIG. 31 (iii). This technique can then be easily extended to deposit different layers of different materials, thus fabricating customized nanofiber array scaffolds on planar and nonplanar Geometries.

In conclusion, STEP technique for fabricating highly aligned arrays of polymeric fibers having diameters ranging from 50 to 500 nm with lengths of several millimeters has been demonstrated. The proposed STEP technique uses a spinneret to deliver polymeric solution, which is continuously collected in the form of aligned nanofiber arrays on a rotating planar or nonplanar substrate. STEP technique is shown to deposit polymeric fibers on spherical surfaces precisely with tunable geometrical spacing, thus heralding new opportunities for the design of novel sensors conforming to three-dimensional surfaces. The design workspace for depositing fibers using this approach is shown to depend upon processing parameters of rotational speed and material properties of solution rheologies. The diameter of fibers decreases with increasing rotational speed of the substrate and rapidly converges to a constant diameter value at higher rotational values. At these high rotational speeds, varying the solution rheologies of the polymer solution for a given molecular weight provides control on the final dimensions of the fiber. Increasing the concentration increases the fiber diameter and repeatable fibers having uniform defect-free diameters ranging from 50 to 500 nm are demonstrated. Thus, using the approach outlined in this study, similar experiments can be conducted on other polymeric systems and a general roadmap for depositing nanofiber arrays can be generated. This will not only advance our current understanding of nanoscale polymeric fiber physics but also open up new potential nanotechnology applications.

Example 6

Control of Cell Behavior by Aligned Micro/Nanofibrous Biomaterial Scaffolds Fabricated by Spinneret-Based Tunable Engineered Parameters (STEP) Technique With the recent advancements in nano/microtechnology, it is now possible to fabricate fibrous scaffolds at length scales which mimic living tissues. Fabricating fibrous scaffolds is one promising component for tissue-engineering approaches and equally important is shaping them to spatially resemble living tissues. Numerous studies have indicated the importance of key engineered parameters: fiber diameter, fiber alignment, geometrical fiber spacing, scaffold mechanical strength, fiber roughness, and topological constraints of scaffolds. These parameters constituting a vast design space with limited available information on their engineering limits along with their interdependency rules lead to a currently loose framework for designing fibrous biomaterial scaffolds.

The design framework of scaffolds must address the design aspects at different hierarchical levels within the scaffolds. This could include mimicking native extracellular matrix (ECM) consisting of fiber networks having diameters ranging from 50 to 500 nm, which can be divided into four distinct spatial domains: macroscale (>1 mm), micrometer scale (1 μm-1 mm), submicrometer scale (100 nm-1 μm), and finally nanoscale (<100 nm). A unit block of the engineered scaffold at each level of abstraction having corresponding dimensions should mimic the ECM, thus potentially providing a pathway to successful tissue engineering. At the macroscale, the arrangement of scaffold unit blocks should enable fusion of cells into bundles, while at the microscale, scaffold unit block dimensions on the order of individual cellular dimensions along with the topological constraints dictate individual cellular response. The first two levels of abstractions have been studied extensively in the past [Norman J J & Desai T A. Ann Biomed Eng. 2006; 34:89] and the next two levels, namely the submicrometer and nanoscale are being actively investigated with the recent advancements in engineering.

These length scales hold promise for unlocking a deeper mystery to cellular dynamics as cellular features (myofibrils, filipodia, etc.) dictate submicrometer and nanotopographical scaffold unit block dimensions of fiber diameter and geometrical fiber spacing. The exact role of spatial dimensionality and whether the hierarchical design criteria are fractal in nature are among the fundamental unanswered questions. Thus, a multidisciplinary approach is warranted to establish an engineering framework for the design of scaffolds at each hierarchical level. Furthermore, hierarchical assembly and shaping of one-dimensional (1-D) blocks into three-dimensional (3-D) structures resembling native organs and tissues may be achieved to improve clinical outcome in tissue engineering applications.

Current scaffolding technologies of electrospinning, phase separation and template synthesis are limited in depositing multilayer aligned scaffolds representing different hierarchical levels [Norman J J & Desai T A. Ann Biomed Eng. 2006; 34:89]. The proposed spinneret-based tunable engineered parameters (STEP) technique offers flexibility in assembling biomaterial scaffolds in a bottom up assembly environment.

The essential 1-D components: micro/nanofibers are deposited either sequentially or continuously in high speeds in each layer. This technique uniquely provides control of the dimensions of the fibers deposited in aligned configurations with tunable geometrical spacing, thus, establishing a platform for the investigation of cellular dynamics and cellular adhesion on scaffolds, which can then be used to develop a roadmap for the design of customized hierarchical scaffolds for tissue engineering. STEP proposes two techniques for creating custom point-to-point sequential (FIG. 32) or continuous high-density (FIG. 1A) single and multilayered biomaterial scaffolds built of aligned nano/microfibers with or without roughness features and tunable geometrical fiber spacing.

Figure 32A:
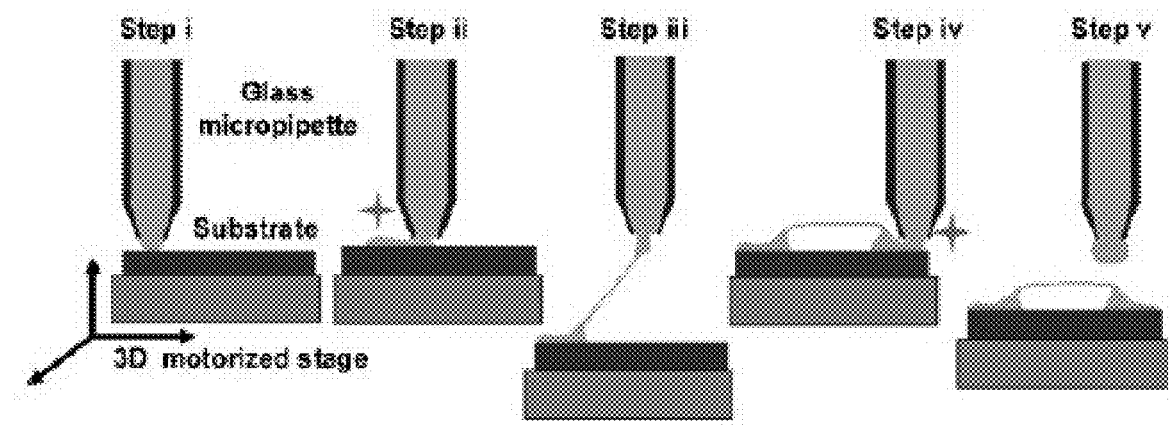
FIGS. 32A-32B show a point-to-point sequential technique to form fiber arrays.
Figure 32B:
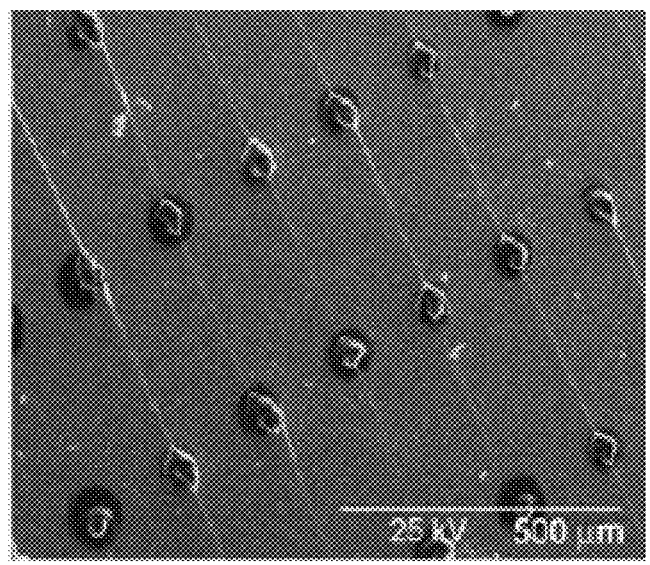

In the point-to-point custom technique, fiber attachment to different substrates is highly dependent upon the surface chemistry. To prevent scaffold detachment from the substrate, a "double attachment" strategy of the fibers to the substrate is implemented to enhance the adhesion between the fiber scaffolds and substrate. The attachment scheme and drawing strategy is schematically represented in FIG. 32. The pipette is fixed perpendicular to a given substrate, which is mounted on the motorized XYZ nanopositioner. At first, the substrate is raised until it comes into contact with the polymer droplet at the end of the glass micropipette tip. At this stage the substrate is moved horizontally forming a double attachment. Here, the wait time before drawing a fiber offers control of the viscosity of the polymer solution. After drawing the fiber, the substrate is once again brought into contact with the glass micropipette, thus forming a suspended fiber. The stage is then moved horizontally to establish the second double attachment for the fiber. Using this approach, biomaterial scaffolds are built sequentially with the desired geometrical fiber spacing between consecutive fibers. Multiple layers are deposited in a similar fashion by repeating the above steps in any desired angular orientation to the pre-deposited layer(s). It is possible to increase the throughput of this technique and deposit multiple layers in a single step by using an array of individually controlled probes.

In the continuous high-density technique, a glass micropipette spinneret is fixed adjacent to, e.g., perpendicular to, a given substrate attached to a motor, such as a DC motor mounted on a motorized XYZ nanopositioner as schematically represented in FIG. 1A. Fibers are drawn continuously on the rotating substrate and the desired geometrical fiber spacing is achieved by controlling the vertical speed of the nanopositioner and by choosing an appropriate rotational speed of the DC motor. Multiple layers at desired orientations are fabricated by depositing fibers on top of previously deposited layer(s).

Dry spinning has been used extensively in the fiber industry and involves dissolving a polymer in a good solvent forming a viscous "spin dope," which is subsequently extruded from a glass micropipette spinneret. As the dope exits the glass micropipette spinneret, ambient air is used to evaporate the solvent, thus solidifying the fiber, which is subsequently deposited on the substrate. The key parameters in forming fibers of desired diameter for a polymer of given molecular weight are polymer/solvent concentration in the spinning dope and automation parameters of drawing speed. Polymer molecules dissolved in solvents constitute a network of entanglements, which can be regarded as "short and long range" at higher and lower concentrations of the solvent, respectively. Solvent evaporation causes the local polymer concentration in the spin dope to increase as the spin dope extrudes from the glass micropipette spinneret. This can be viewed as transformation from short to long-range entanglements of a given polymer chain in the system. In the long range entanglement network, a given chain has a sufficiently large number of points where it encounters entanglements with other chains in the system, thus greatly reducing the mobility of chains and starting the process of forming a solidified fiber. An initial high concentration of polymer in the spin dope leads to fibers having larger diameters and conversely, a lower polymer concentration in the initial spin dope does not allow fiber formation, due to absence of entanglements.

Figure 33:
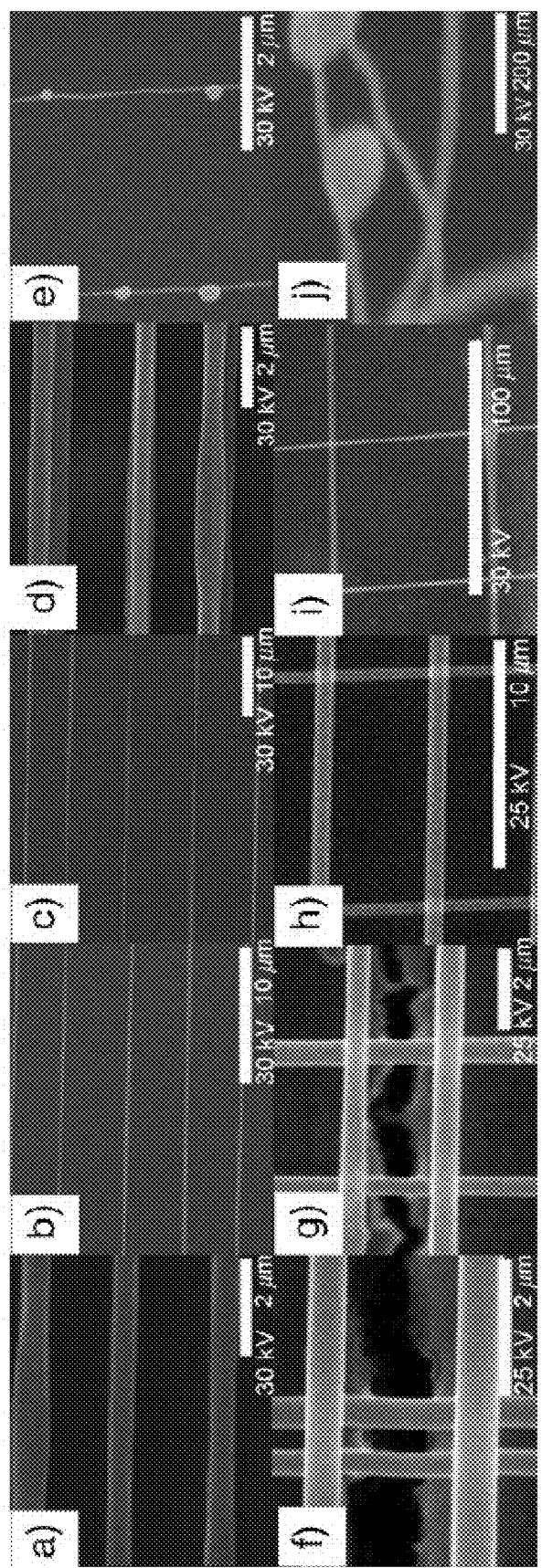
FIGS. 33A-33J are scanning electron micrographs of (A-E) single-layer scaffolds and (F-J) double-layered scaffolds, and roughness features in the form of beads on sub-50 nm fibers (E, J). Scale bars: 0.2 mm in (J), 2 mm in (A, D-G), 10 mm in (B, C, H), and 100 mm in (I).

Similar to the electrospinning technique for fiber fabrication, the STEP technique relies on material parameters of polymer molecular weight and solution polymer concentration in achieving control of the fiber diameter. Furthermore, processing parameters of angular and vertical speeds of the substrate are responsible for distributing the fibers at user-defined geometrical spacing. Thus, by selectively choosing the material parameters, we produce defect-free polymeric fibers having uniform diameters ranging from sub-50 nm to submicrometer and several millimeters in length. This, coupled with the processing parameters enabled fabricating single and multilayer fiber scaffolds with tunable geometrical spacing varying from submicrometer to micrometer scales as shown in FIGS. 33A-33J. Fibers having roughness features such as "beads" were fabricated by dry spinning low polymer concentration solutions and typically the beaded structures are connected by sub-30 nm diameter fibers as shown in FIGS. 33E and 33J.

In developing STEP technology to create putative biomaterial/biological scaffolds for tissue-engineering applications, we based our strategy on the premise that such tunable parameters play a significant role in the efficacy of biomaterial/biological scaffolds by controlling cell behavior. Therefore, the major theme of this work has been in demonstrating the capabilities of the STEP technology for fabricating customized biomaterial scaffolds. Here, we present proof-of-concept for cell-based tissue-engineering applications and cellular interactions in the vicinity of several fiber topological constraints. Cell adhesion, proliferation and topologically constrained migration are demonstrated on fibrous scaffolds composed of four different degradable and non-degradable materials: polystyrene [PS: molecular weight ($M_w$) 860 kg $mol^{-1}$, Pressure Chemicals, USA dissolved in Xylene, 10% by weight], poly-methylacrylate [PMMA: $M_w$ 900 kg $mol^{-1}$, Micro-Chem (USA), dissolved in chlorobenzene, 9 wt %], polylactic acid [PLA: $M_w$ 77450 g $mol^{-1}$, Sigma-Aldrich (USA), dissolved in Chloroform, 10% by weight] and poly-lactic co-glycolic acid (PLGA: PURASORB1, 85/15, dissolved in chloroform, 10 wt %).

The mouse (C2C12) cell line is a population of progenitor cells which have been isolated from mouse muscle [Yaffe D & Saxel O, Nature. 1977; 270:725]. They were chosen for the cell seeding experiments because they can differentiate to form many cell types including those of osteogenic and myogenic lineages [Milasincic D J, et al. In Vitro Cell. Dev. Biol. Anim. 1996; 32: 90; Katagiri T, et al. J. Cell Biol. 1994; 127:1755]. Furthermore, C2C12 have been previously shown to be useful for studies involving polymer scaffold development for tissue-engineering applications and for controlled cell alignment on micropatterned PLA composite materials [Riboldi S A et al. Biomaterials. 2005; 26:4606; Radisic M et al. Biotechnol. Bioeng. 2003; 82:403; Papenburg B J et al. Biomaterials. 2007; 28:1998]. C2C12 cells were obtained from ATCC (Rockville, Md.) and maintained in complete medium [Dulbecco's modified Eagle's medium (DMEM), 10% fetal bovine serum (FBS) and 1% penicillin/streptomycin (Invitrogen, Carlsbad, Calif.)] at 37° C. in a humidified atmosphere of 5% $CO_2$ in 25-cm2 culture flasks and fed with fresh medium every 2-3 days. For subculture, the cell monolayer was washed with PBS and incubated with trypsin/EDTA for 5 min at 37° C. to detach cells. To facilitate visualization of cells in the presence of fibers, C2C12 were stably transfected for expression of GFP-a-tubulin [Jarvik J W & Telmer C A, Ann. Rev. Genet. 1998; 32:601; Jarvik J W, et al. Biotechniques 1996; 20:896]. Trypsin effects were inhibited with the addition of complete medium at room temperature. Approximately 20000 cells in 20 mL volume of medium (resuspended cell mixture) were seeded on top of the scaffold (approximate volume: 5 mm×5 mm×fiber diameter) and incubated at 37° C. in a humidified atmosphere of 5% $CO_2$ for 3-4 h to allow cell attachment to fibers. Cells on scaffolds were imaged on a Zeiss Axiovert 200 microscope with a 10×, 0.45 NA. Plan-Apochromat phase 1 objective (Carl Zeiss, Inc., Thornwood, N.Y.) with a computer operated stage (Ludl Electronic Products Ltd., Hawthorne, N.Y.) and GFP-filter set (Chroma Technology Corporation, Rockingham, Vt.). To detect cell migration, proliferation, and to investigate the effects of topological constraints of biomaterial scaffolds, a 24 h time lapse experiment was performed with the cells/scaffold in complete medium and incubated on the stage at 37° C. in a humidified chamber with 5% $CO_2$. Images were captured every 10 min with auto exposure and fixed focus using Axiovision Rel 4.5 software (Zeiss, Inc.). Time-lapse movies were created using ImageJ software.

Figure 34:
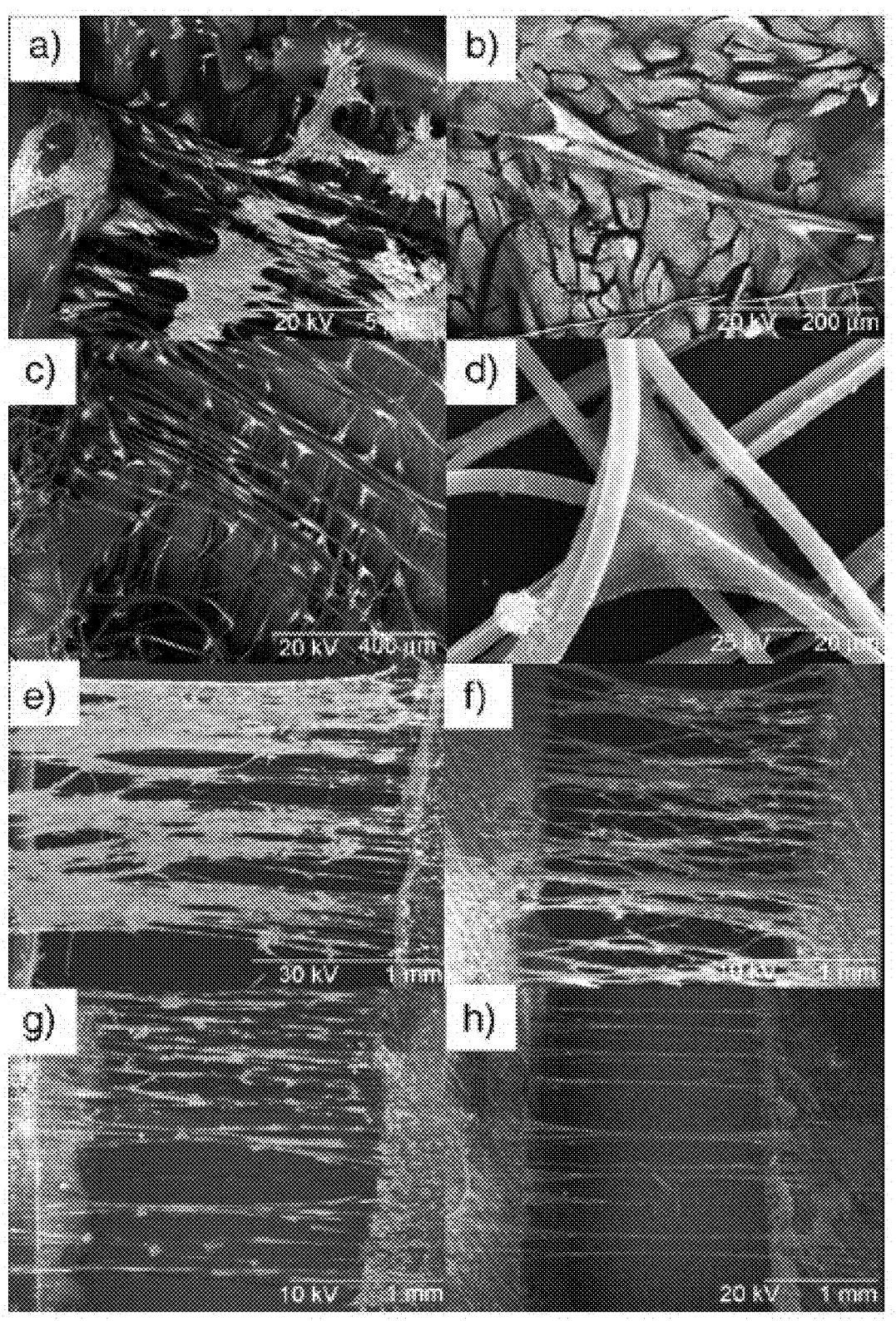
FIGS. 34A-34H are scanning electron micrographs of (A-D) C2C12 cells on single- and double layered scaffolds fabricated by point-to-point sequential technique; and (E-H) C2C12 seeded PS, PMMA, PLA, and PLGA scaffolds, respectively, fabricated using the continuous technique.

Cell adhesion to surfaces occurs by focal contacts between the cell and a substrate, which are vitally important for proper cell proliferation, migration, and differentiation and often are required for optimal growth factor activity. In this study, we demonstrate cell attachment, migration, proliferation, alignment, and elongation, which resembles the myotube morphology on our engineered nano/microfiber scaffolds. Single-layered scaffolds showed fusion of cells into bundles. Cells were observed to elongate along the fiber axis (FIGS. 34A and 34B) and spreading of a cell between multiple layers of multiple fibers was also noted (FIGS. 34C-D). Cell attachment and fusion of cells into bundles on biomaterial scaffolds of PS, PLA, PMMA, and PLGA is demonstrated in FIGS. 34E-34H for continuous technique.

Figure 35:
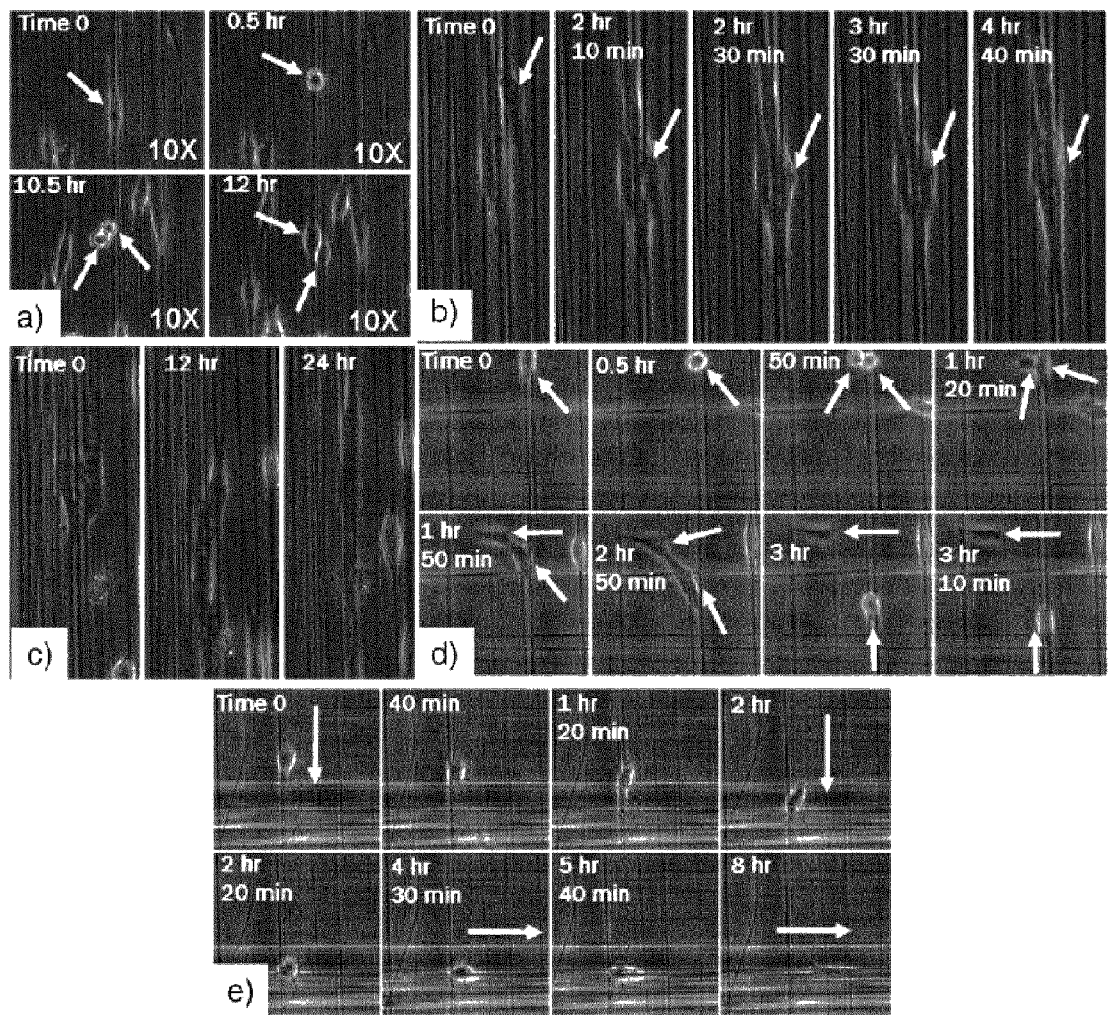
FIGS. 35A-35E show time-lapse microscopy of C2C12 cell proliferation and migration on single- and double-layered fiber scaffolds. (A) Cells proliferated over 12 h on single-layered PS scaffolds; (B) cells migrated laterally one fiber at a time; (C) cells elongated within 24 h to adopt a myoblastic cell morphology; (D) daughter cells attached to perpendicular fibers and migrated perpendicularly away from one another at fiber intersections of double-layered scaffolds; (E) cell migration on double-layered fiber scaffolds demonstrating right angle turns onto adjacent perpendicular fibers. All time-lapse images were captured at 10×.

To investigate the effects of topological constraints on cell migration, cells cultured on single- and double-layered fiber scaffolds were imaged using time-lapse microscopy over 24 h. FIG. 35A shows representative images of a mitotic cell which divided within 12 h of the cells coming into the field of view. Interestingly, the cell continued to migrate along a single fiber while undergoing prophase through anaphase of the cell cycle. The two daughter cells which formed during cytokinesis then spread out along two neighboring but distinct PS fibers. Cells were observed to migrate along fibers bi-directionally and moved primarily in a single direction along fibers, but occasionally changed directions. All the cells within the same population did not move exclusively in a single direction on the fibers. For example, two cells on a single fiber were observed to migrate toward one another and then change direction and move away from one another. Some cells were attached to single fibers, while others appeared to be attached to two or more fibers. Cells were able to detach from one fiber completely and join a group of cells on a neighboring fiber (FIG. 35B). Fibers with cells attached on them were observed to flexibly move due to cellular migration. Over time, cells elongated along fibers in typical morphology of myogenic differentiation for this cell line (FIG. 35B)[Yaffe D et al. In Vitro Cell. Dev. Biol. Anim. 1996; 32:90]. Mitotic events were observed on a double-layered scaffold in close proximity to a fiber intersection and daughter cells attached to perpendicular fibers at the junction and migrated away from one another at approximately 90° angles (FIG. 35D). Single cells on double-layered scaffolds were observed to make right angle transitions as shown in FIG. 35E. Cell proliferation was also observed by time-lapse microscopy of cells seeded on fibers with PS "beads" and cell migration on beaded structures was apparently inhibited compared to smooth fibers (data not shown). Thus, the observed behavior of cells on customized biomaterial scaffolds can provide a gateway to a deeper understanding of cellular dynamics.

Cells readily attached to our engineered nano/microfiber scaffolds and formed multiple focal contact points on the fibers, as evidenced by cell spreading and alignment along fibers. Cell morphology on single-layered scaffolds changed over time from a cuboidal shape to an elongated "myotube"-like morphology. This suggested that the parallel fiber configuration may promote cell differentiation of C2C12 toward the myogenic lineage. Interestingly, double-layered scaffolds did not show a similar degree of elongation. Cells appeared to maintain the cuboidal rather than elongated morphology, suggesting a different phenotype was achieved for cells cultured on double-layered scaffolds. Moutos et al. have previously shown that cells maintain a rounded morphology on woven agarose fibers which may be desirable for chondrocyte maturation [Moutos F T et al., Nat. Mater. 2007; 6:162], which is in agreement with the present study. Although our cells are not rounded but are spread between fibers, fiber composition, geometry, and alignment could influence cell-type specific morphology and a rounded morphology for C2C12 could indicate poor attachment. Hence, by modifying the orientation of fibers and the geometrical alignment of multiple layers it might be possible to influence tissue-specific phenotypes.

Figure 36:
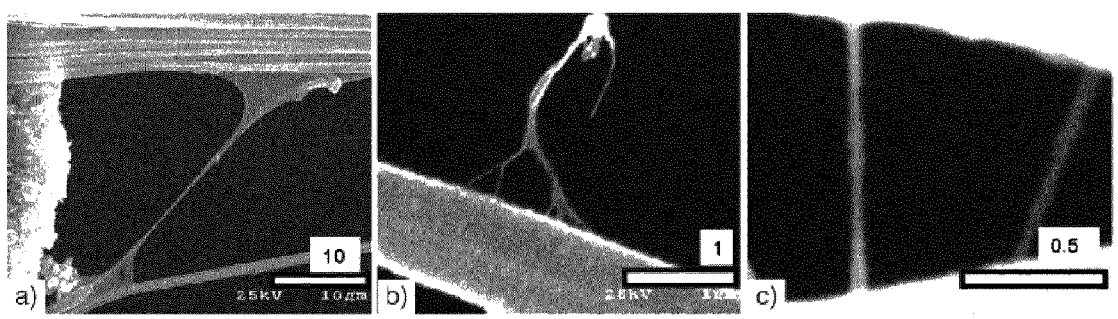
FIGS. 36A-36C are scanning electron micrographs of C2C12 cells seeded on PS fibers with scale bars noted per panel; (A) group of cells bridging bundle of fibers, (B-C) cell(s) bridging fibers with sub-100 nm possible anchoring mechanisms.

The STEP technology enables investigation of multiple surface parameters that influence cell behavior such as fiber size, geometrical spacing, and nano/microarchitecture. A general framework outlining the bounds of key engineered parameters is highly desirable and is currently loosely defined. For example, it is well-known that submicrometer fibers are conducive to tissue engineering, but the exact mechanisms by which cells attach to the repeat 66 nm banding of the collagen fibers in the ECM is not completely understood [Norman J & Desai T A. Ann. Biomed. Eng. 2006; 34:89). Similarly, are groups of fibers separated at equal distances (FIG. 33D) preferred over single fibers due to increased local mechanical strength and increased available surface area? Apart from the generally accepted notion of minimum fiber spacing for cell migration and transfusion of fluids through the fibers, the exact contributions of geometrical fiber spacing on cell behavior is not clear. Fiber spacing likely affects cell migration and proliferation as demonstrated in the biological world by sea urchin mesenchyme cells, which migrate by extending their pseudopods from the main body on the order of 500 nm [Gustafson T & Wolpert L. Exp. Cell. Res. 1999; 253:288]. It is well-known that cells fail to attach to fibers spaced far apart and conversely, cell migration to underlying layers is inhibited if the fibers are too closely packed. Thus, it may be possible to achieve directed cell migration by engineering layers of larger diameter fibers with large fiber spacing in contact with underlying layers of decreasing fiber spacing and diameters. Fiber-spacing experiments can then provide a platform to study behavior of individual cells as well as populations as shown in FIG. 36. The tantalizingly different mechanisms and appendages by which C2C12 cells anchor as a group (FIG. 36A) or individually (FIGS. 36B-D) are of significant interest, and with future studies, can be used for generating geometrical rules for spacing fibers in a hierarchical scaffold.

Figure 37:
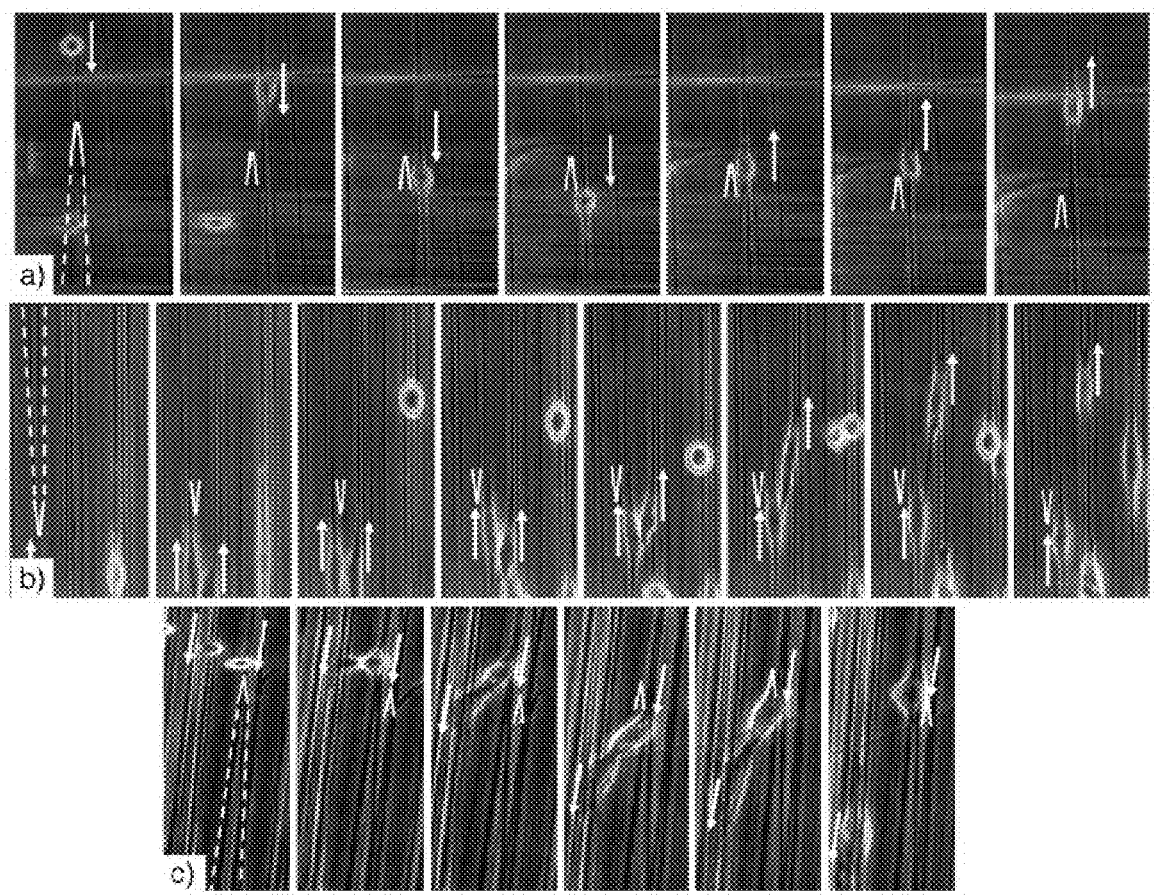
FIGS. 37A-C are time lapse microscopy of C2C12 cell migration on single- and double-layered fiber scaffolds as a function of diverging fibers shown by lines superimposed on diverging fibers and origin of divergence shown in subsequent frames by "V" in direction of divergence: (A) single cell retraces original path once it encounters a diverging fiber on PS scaffold; (B) competing migration behavior of cells on PS scaffolds: cell on left encounters a diverging fiber and stops migrating, while cells on right are on parallel fibers and continue migrating; (C) competing migration of cells on PLGA scaffolds, cell on right encounters diverging fibers and stops migrating.

Geometrical constraints in fibrous scaffolds play a vital role on cellular adhesion and mobility. Using the principles of contact guidance [Gustafson T & Wolpert L. Exp. Cell. Res. 1999; 253:288], it may be possible to engineer biomaterial scaffolds, which can accommodate specific site tissue rebuilding efforts along with different cell lines. By using geometrical intersections of fibers it may be possible for cells to migrate to different layers, as elongated cells have been observed to attain a rounded morphology at the intersection of fibers and on numerous instances, cells are observed to make right-angle transitions. Fiber alignment is known to be conducive to tissue engineering, but level of alignment is unclear. For example, as shown in FIG. 37, behavior of cells encountering diverging fibers is observed, which appears to limit cellular motion in the direction of diverging fibers. This level of abstraction once embedded in a scaffold at points of interest can control cell migration or limit cells to specific preselected sites, thus leading to scaffolds with a mix of cell lines and functionalities.

The exact mechanisms for such behavior are not yet clear, but it offers significant potential in designing and engineering scaffolds with a mix of fiber dimensions and materials to achieve directed motion. Finally, the motion of the flexible fibers due to cell migration could also be used to study the biomechanical forces exerted by a cell on its environment, which can generate a framework for designing stronger and more robust scaffolds.

In conclusion, the key advantages of the STEP technology are scalability, precision and 3-D fabrication of hierarchical scaffolds. Single- and multilayered micro/nanofibrous scaffolds of different biomaterials were fabricated with tunable fiber spacing in aligned configurations. Seeded mouse C2C12 progenitor cells on the scaffolds resulted in cellular elongation resembling myotube morphology along the fiber axis, spreading of cells along orthogonal layers and fusing of cells into bundles at the macroscale. Furthermore, cells were observed to make right angle transitions along orthogonal layers and stop or reverse direction of motion upon encountering diverging fibers. These insights coupled with the flexibility of fabricating scaffolds using STEP can be used to create a wide variety of scaffolds resembling the various hierarchical domains of ECM with a mix of biomaterials in the same scaffold for further investigations of cellular dynamics and tissue engineering. STEP offers scalability to fabricate biomaterial-based scaffolds from micro/nanoelectromechanical systems (M/NEMS)-based implantable devices to tissue engineering macroscales. This study along with the preliminary observations on the effects of geometrical constraints on cellular adhesion and migration opens new frontiers in designing specialty scaffolds. Future applications could include the creation of putative biomimetic scaffolds to control cell proliferation, migration and differentiation for tissue engineering applications.

Example 7

Polymeric Nanofibers: Design Space and Methodology for Depositing Aligned Nanofiber Arrays Here we present a design framework based upon molecular chain entanglements on fabricating smooth and bead free fibers having diameters ranging from sub-50 nm to excess of 500 nm and having lengths in excess of several millimeters. Polymeric fiber arrays of known dimensions are deposited in aligned configurations and in user defined spacing by the continuous ejection of polymer solution from a glass micropipette followed by evaporation of the solvent as shown schematically in FIG. 1A. The design space for fabricating uniform defect-free fibers depends upon achieving a minimum number of polymeric molecular entanglements to allow fiber formation to occur, which can be determined by identifying the effect of polymer solution rheology on the fiber formation process.

Polystyrene (PS) is chosen as the model polymeric system for it is readily available, a very well studied and cost effective polymer system that can be obtained in very narrow polydispersities. For PS and in accordance with the classic graph by Graessely (FIG. 2), the design workspace covers a wide range of polymer-solvent concentration regimes including dilute, semi-dilute and concentrated at different molecular weights. PS being brittle is traditionally melt-spun for industrial application and some recent attempts at electrospinning PS fibers have demonstrated regions of fiber formation for several molecular weights in different solvents [Lee K, et al. The change of bead morphology formed on electrospun polystyrene fibers, Polymer. 2003; 44(14):4029-34; Wang C., et al. Scaling laws in Electrospinning of Polystyrene Solutions, Macromolecules. 2006; 39(22):7662-72]. Smooth bead-free uniform diameter fibers are observed to form at concentrations with sufficient molecular entanglements (~1.75 entanglement concentration ($C_e$)). In this letter, the design framework based upon molecular entanglements is developed in relation to two concentrations lying at the boundaries of (i) dilute and semi-dilute (unentangled) and, (ii) semi-dilute (unentangled) and semi-dilute (entangled) domains. The former commonly referred to as critical overlap concentration (C*) can be determined for the entire range of molecular weights using the Mark-Houwink-Sakurada relation:

$$C^* \sim \frac{1}{[\eta]} = \frac{1}{KM^a} \quad (19)$$

The latter concentration referred to as entanglement concentration, $C_e$, can be calculated from Heo Y & Larson R G. The scaling of zero-shear viscosities of semidilute polymer solutions with concentration, J. Rheology. 2005; 49(5): 1117-28:

$$C_e = n_e^{(3\nu-1)}/M_w A_2 \quad (20)$$

where $n_e$ is the number of monomers between entanglements and is defined as $$n_e = M_e/m_o, M_e, \text{ the entanglement density of the melt} \quad (21)$$

(PS~13,309 g·mol$^{-1}$)
[Larson R G. The structure and rheology of complex fluids, Oxford University Press, 1999] and ν is the excluded volume exponent calculated as:

$$\nu = (a+1)/3 \quad (22)$$

with a being the Mark-Houwink-Sakurada constant obtained from dilute solution viscometry (0.69205) and $M_w A_2$ are calculated as:

$$C^* = \frac{5.3}{M_w A_2} \quad (23)$$

Figure 38:
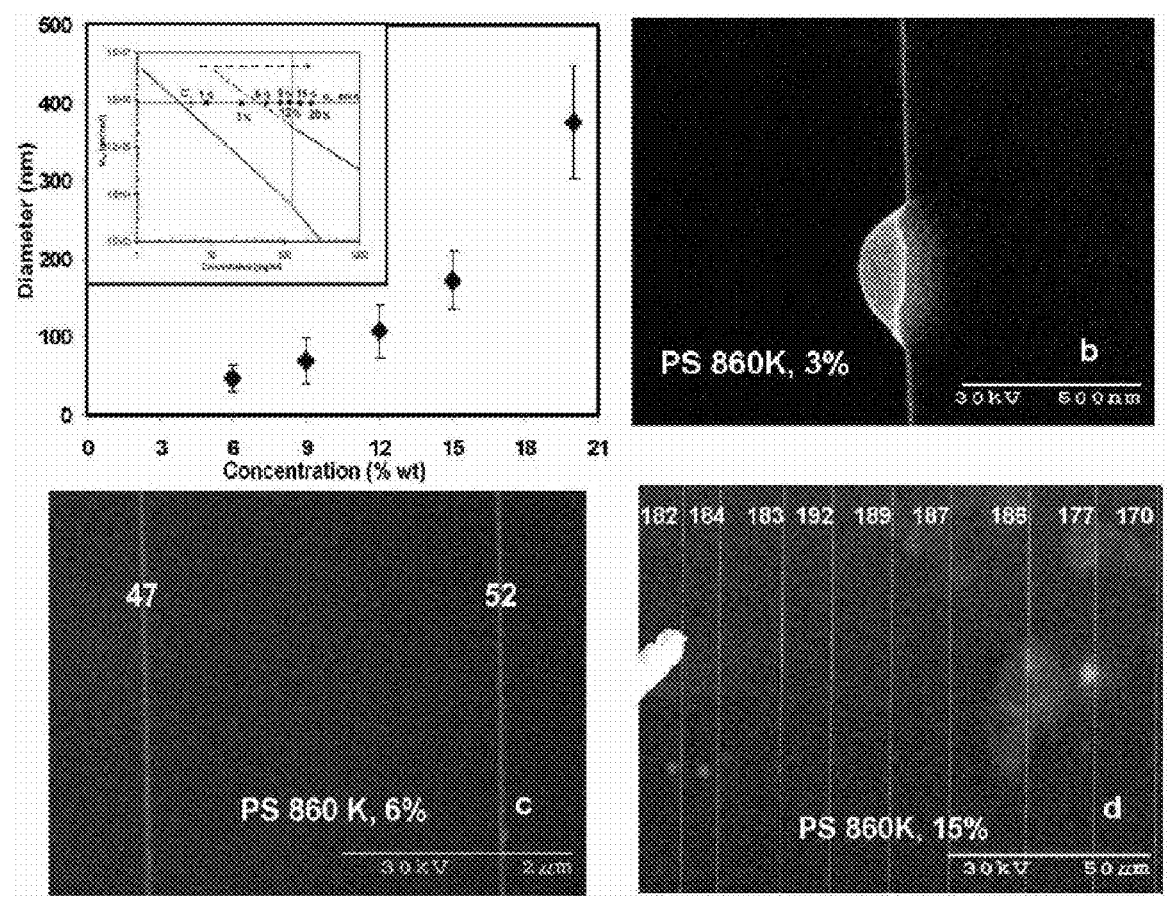
FIGS. 38A-D show the effect of concentration on diameter of fibers.

C* and $C_e$ decrease with increasing molecular weights. However, increasing the polymer solution concentration at a fixed molecular weight reduces the radius of gyration ($R_g$) and simultaneously increases the entanglement density ($M_E$) of the solvated polymer molecules in a good solvent, which leads to an increase in fiber diameter. PS 860K (g/mol) was dissolved in xylene in increasing concentrations by weight (1, 3, 6, 9, 12, 15 and 20%) as shown in FIG. 38A (inset). The concentrations were chosen to investigate the effects of polymeric chain entanglements on fiber formation process and diameter across different concentration regimes.

At low dilutions, we were not able to form fibers and polymer solution was deposited in the form of droplets. Increasing the concentration increased the polymer chain entanglements, thus resulting in continuous fibers. However, below 6% concentration, we obtained beaded fibers. The beaded structures (FIG. 38B) were connected by sub-40 nm fibers and could not be pulled over several millimeters in length and were discarded from further analysis. Defect-free fibers started forming at 6% concentration and at concentrations greater than 20%, fibers with diameters greater than 500 nm were obtained, which were also excluded from this study.

Figure 12A:
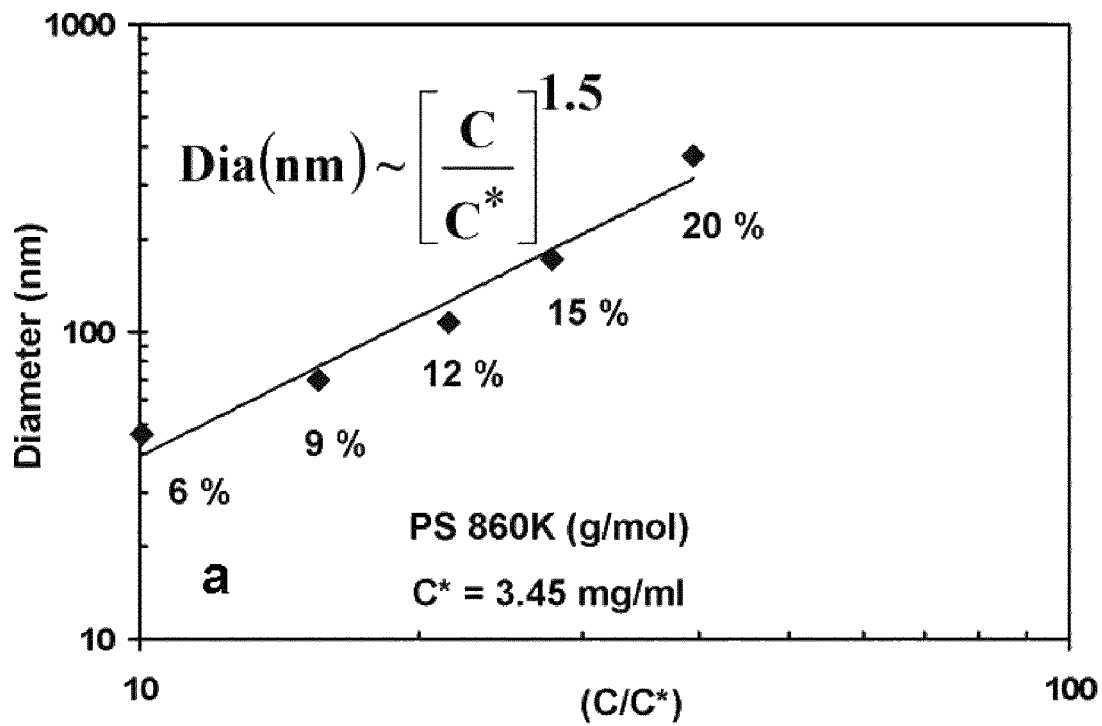
FIGS. 12A-12B are graphs showing scaling laws developed based on (A) critical overlap concentration and (B) critical entanglement concentration.
Figure 12B:
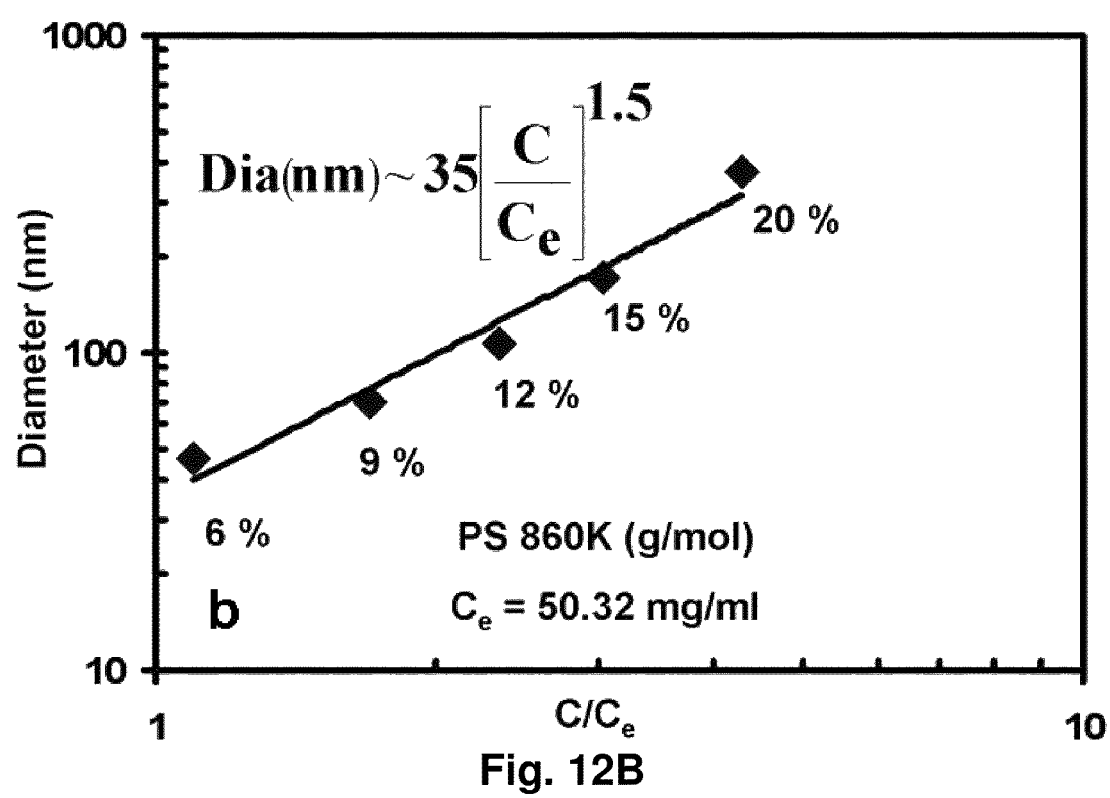

Following the approach outlined for electrospun fibers [McKee M et al. Correlations of Solution Rheology with Electrospun Fiber Formation of Linear and Branched Polyesters, Macromolecules. 2004; 37(5):1760-7; Gupta P., et al., Electrospinning of linear homopolymers of poly(methyl methacrylate): exploring relationships between fiber formation, viscosity, molecular weight and concentration in a good solvent, Polymer. 2005; 46(3):4799-810], linear regression analyses was conducted to determine the dependence of fiber diameter on different concentrations as shown in FIG. 12:

$$Dia(nm) \sim \left[\frac{C}{C^*}\right]^{1.5} \text{ and } Dia(nm) \sim 35\left[\frac{C}{C_g}\right]^{1.5} \quad (24)$$

The developed exponent (1.5) is observed to be lower in value compared to electrospinning studies (~2.6-3.1) and can be attributed to the difference in the process of fabricating fibers, different polymer and the high molecular weight used in this study. However, the calculated value of $C_e$ of 50.32 (mg/ml) is in agreement with the experimentally observed concentration of 55.21 (mg/ml, 6% wt.), where uniform defect-free fibers are formed, which is significantly lower than the reported values for electrospinning process (>1.75$C_e$) [McKee M., et al., Macromolecules. 2004; 37(5):1760-7; Shenoy S. et al., Role of chain entanglements on fiber formation during electrospinning of polymer solutions: good solvent, non-specific polymer-polymer interaction limit, Polymer. 2005; 46:3372-84; Gupta P., et al., Polymer. 2005; 46(3):4799-810; Wang C. et al. Macromolecules. 2006; 39(22):7662-72].

Molecular entanglements can also be increased by increasing the molecular weight at the same polymeric concentration due to increase in the size of polymer molecules. The increased entanglements reduce the ability of individual polymeric chain segments to undergo deformation during fiber formation process, thus resulting in bigger diameters. Conversely, for lower molecular weight species, polymer solution concentration needs to be high to provide enough entanglements for fiber formation process to occur. Four different molecular weight (100K, 411K, 860K and 1800K (g/mol)) polymer solutions were prepared (12% by weight), with 1800K and 100K having the highest and lowest number of entanglements respectively and schematically illustrated in FIG. 13A. PS 1800K with the highest number of entanglements produced biggest fibers and for PS 100K the entanglement concentration was lower than $C_e$ resulting in beaded fibers, which were discarded for further analysis due to non-uniformity of the diameter coupled with the inability to draw them over several millimeters in length. The exponent in the scaling law developed on zero shear viscosity (0.56, FIG. 13B) is slightly different than the electrospinning studies on branched and linear copolymers of PET-co-PEI (0.8, $M_w$ ranging from 11,700-106,000 (g/mol)) [McKee M., Macromolecules. 2004; 37(5):1760-7], PMMA (0.72, $M_w$ ranging from 12,470-95,850 (g/mol)) [Gupta P, et al. Polymer. 2005; 46(3):4799-810], and PS (0.41, $M_w$ 300K (g/mol) [Wang C, et al. Scaling laws in Electrospinning of Polystyrene Solutions, Macromolecules. 2006; 39(22):7662-72]. The differences in values of exponents are in part due to differences in the fabrication process, the polymers and the molecular weights used.

Nearly equal diameter fibers of several molecular weights can be achieved by equilibrating the entanglement density.

The equilibrated entanglement density value can be normalized either by C* or $C_e$. We chose to normalize using C* as it was accurately determined by dilute solution viscometry experiments for a wide range of molecular weights (See Methods). Corresponding to the C/C* value for PS860K (g/mol) at 15% (wt) concentration, PS 100K, 411K and 1800K (g/mol) polymer solutions were prepared as shown in FIG. 14A. The experimentally obtained equivalent diameters with the appropriate solution concentration (wt %) for the different molecular weights are shown in FIG. 14B.

Scaling laws from equation (24) were used to determine the fiber diameters for several molecular weights at different concentrations and were found to be in agreement with experiments as shown in FIG. 16A. This lead to generating isodiameters spanning the entire solution rheological design space by using equations (19-24) as shown in FIG. 16B. Lower molecular weights require higher concentrations to achieve the desired entanglement density to form fibers and conversely higher molecular weights require lower concentrations to form smooth, defect-free, uniform diameter fibers having lengths of several millimeters. Predictions from the isodiametric design space clearly indicate that lower molecular weight species (10K and less) lack the ability to be employed for successful integration in nano-enabled technologies utilizing high aspect ratio (length/diameter) fibers. Thus, by visual inspection of the mapped design space, it is straightforward to determine regions of solution rheologies where fabrication of smooth, defect-free and uniform diameter fibers having lengths of several millimeters is expected. Deposition of polymeric material in the form of droplets or beaded fibers occurs within the shaded region bound by bold line of $C_e$ as shown in FIG. 16B. Additionally, by tracing the isodiameter contours it is possible to distinguish if fiber formation will occur at a given molecular weight. For example, the 20 nm isodiameter line clearly shows that fiber formation will not occur at all molecular weights, as it falls below the threshold $C_e$. Hence the isodiametric design space significantly compliments the polymeric nanomanufacturing platform for depositing aligned fiber arrays of desired dimensions and mechanical properties (molecular weights) in known locations. These examples, illustrate non-limiting methods of determining an isodiametric design space for a given polymer and solvent combination. The isodiametric design space can be determined mathematically and/or experimentally, as is shown herein.

In conclusion, we demonstrate a nanomanufacturing platform to deposit polymeric fibers having diameters ranging from 50 nm to upwards of 500 nm with several millimeters in length. The polymeric fibers are observed to form at the onset of critical entanglement density, which is significantly lower than the reported values for electrospinning based fiber formation techniques. Furthermore, the scaling laws developed for estimating the diameter of the fiber from the critical concentration $(Dia(nm) \sim (C/C^*)^{1.5})$ and from the critical entanglement concentration $(Dia(nm) \sim 35(C/C_e)^{1.5})$ are in accordance with the experimentally observed values. An engineering design framework for depositing fibers of known dimensions and several millimeters in length is developed by plotting the isodiameters (20-900 nm) on the solution rheology based design map and is expandable to other polymeric systems.

Methods.

The experimental setup consists of a micropipette spinneret (diameter: 20-50 µm, Sutter Instruments) mounted perpendicularly to the substrate on a three degree of freedom manual stage (562 Series ULTRAlign™ Precision Multi-Axis Positioning Stages, Newport Inc., USA) as shown in Scheme 1(a). The substrate in turn mounts on to a DC motor, which in turn gets mounted onto a motorized three degree of freedom micropositioning stage (VP-25XA, Newport Inc., USA). Several molecular weights of PS (100K, 411K, 860K, and 1800K $g \cdot mol^{-1}$, Pressure Chemicals, USA) were dissolved in Xylene with varying wt % concentrations ranging for a period of two weeks prior to experiments. The viscous polymer solution was pumped continuously through the micropipette spinneret using a syringe pump (Harvard Apparatus Inc., USA) at a flow rate of 50-100 $\mu l \cdot min^{-1}$. The fibers were collected on a substrate (5 mm in width) in aligned configurations spinning at 550 RPM. Imaging of the deposited fibers was conducted after coating them with gold using a Pelco SC-6 sputter coater and examined using a Hitachi 2460N Scanning Electron Microscope. Digital images from the SEM were obtained using Quartz PCI Image management system software. PS was dissolved in Xylene at low concentrations ~1% by weight and dilute solution viscometry experiments on different molecular weights of PS (50, 100, 160, 411, 860 and 1800K $(g \cdot mol^{-1})$) were conducted @ 30° C. to obtain the intrinsic viscosity and also the Mark-Houwink-Sakurada constants (K=0.0136 ml/gm and a=0.69205 @ 30° C.; see above).

Example 8

Polymeric Micro/Nanofiber Manufacturing and Mechanical Characterization

Polymeric nanofibers are finding increasing number of applications and hold the potential to revolutionize diverse fields such as tissue engineering, smart textiles, sensors, and actuators. Aligning and producing long smooth, uniform and defect-free fibers with control on fiber dimensions at the sub-micron and nanoscale has been challenging due to fragility of polymeric materials. Besides fabrication, the other challenge lies in the ability to characterize these fibers for mechanical properties, as they are widely believed to have improved properties than bulk due to minimization of defects. In this study we present an overall strategy for fabrication and mechanical characterization of polymeric fibers with diameters ranging from sub-50 nm to sub-microns. In the proposed fabrication strategy, polymeric solution is continuously pumped through a glass micropipette which is collected in the form of aligned fiber arrays on a rotating substrate. Polymer molecular weight and polymer solution concentration play dominant roles in controlling the fiber dimensions, which can be used to deposit fibers of different diameters in the same layer or successively built up multi-layer structures. Using this approach, we demonstrate single and multi-layer architectures of several polymeric systems such as Polystyrene (PS), Poly(methyl methacrylate) (PMMA), Poly lactic acid (PLA), and poly(lactic-co-glycolic acid) (PLGA). Further, we demonstrate the ability to manufacture PMMA fixed-free boundary condition cantilevers by breaking the fixed-fixed boundary condition PMMA fibers using Atomic Force Microscope (AFM) in the lateral mode.

An atomic force microscope is a scanning microscope comprising a microscale cantilever having a sharp tip at its end that is used to scan a specimen surface. The cantilever is typically silicon or silicon nitride and the radius of curvature of the tip is on the order of nanometers. When the tip is brought in proximity to a sample surface, forces between the tip and the sample lead to measurable deflection of the cantilever. The deflection can be measured by deflection of a laser spot on the surface of the cantilever, by optical interferometry, etc. The movement of the tip is typically controlled by piezoelectric methods, which allow control at the nanometer level. While the AFM system typically is used to characterize a substrate, it also can be used, as shown herein, to manipulate structures on the nanoscale (that is, nanofabrication). In the methods described herein, the tip of the probe is used to deflect or break one or more polymer fibers. Deflection of the one or more polymer fibers may be used to mechanically characterize the polymer fibers, for example and without limitation, in determining a flexural modulus for the fibers. The probe also can be used to break the fibers if sufficient probe speed and force is applied. The required probe speed and force can be determined empirically for any polymer fiber.

An integrated approach for mechanical characterization of polymeric fibers is developed. In this approach, the fibers are first deposited on commercially available Transmission Electron Microscopy (TEM) grids in aligned configurations and are mapped for accurate locations under the TEM. Subsequently, the fibers are carefully placed under the AFM and mechanically characterized for flexural modulus using lateral force microscopy (LFM). Finally, accurate fiber dimensions are determined under the Scanning Electron Microscope (SEM). The unique advantage of this approach lies in the ability to deposit a large number of fibers with tunable diameters in aligned configurations with fixed-fixed boundary conditions and requires no external manipulation. We present a strategy to fabricate polymeric cantilevers. The methods developed in this study will greatly aid in increasing our fundamental knowledge of polymeric materials at reduced lengthscales and allow integration of these one-dimensional building blocks in bottom-up assembly environments.

The main hindrances to material and mechanical characterization of polymeric micro/nanofibers can be attributed to precisely locating the deposited fibers, depositing fibers in aligned configurations and with appropriate boundary conditions. These problems are further accentuated with nanofibers, as it becomes extremely difficult and virtually impossible to visualize and manipulate them as entire structures to the desired locations. Furthermore, establishing boundary conditions is cumbersome due to the fragility of polymeric material.

Mechanical and material characterization of fibers can be conducted on a bundle of fibers or on single individual fibers. For applications requiring determination of overall strength of a bundle, such as a scaffold for tissue engineering, fibers can be easily assembled into required bundles using current fiber fabrication techniques and manipulated with post processing for appropriate boundary conditions. However, extracting the contribution of each fibril in the bundle from these experiments is not accurate and reliable due to the inability to get an accurate count of fibers of similar dimensions and deposited orientations constituting the bundle. In such experiments, typically a portion of the mat produced using electrospinning is mounted in a Universal tensile testing machine for determining the ultimate tensile strength of the mat (lowest fiber diameter: 200 nm) [above, and Pedicini A & Farris R J. Mechanical behavior of electrospun polyurethane, Polymer. 2003; 44(22):6857-62; Lee K H, et al. Characterization of nano-structured poly(ε-caprolactone) nonwoven mats via electrospinning, Polymer. 2003; 44(4): 1287-94].

On the other hand for applications requiring accurate and deterministic material functions of a single fiber of desired attributes, it becomes imperative to develop strategies for depositing individual fiber in known location with near-exact boundary conditions. The three most commonly employed boundary conditions are: both ends free-free and both ends fixed-fixed and a combination of fixed-free. Free-free boundary conditions are the easiest to impose, as they do not require any external manipulation to impose the boundary conditions. They rely on the force of adhesion between the fiber and the substrate and can be employed for measuring the elastic modulus at very low strains (lowest fiber diameter: 250 nm) [Lee K H et al. Polymer. 2003; 44(4):1287-94]. These measurements are highly susceptible to generate erroneous results when the fibers are analyzed for material functions at higher strains. Fixed-fixed boundary conditions on single fibers are obtained using a host of techniques ranging from using double sided tapes at the ends or using adhesive glues (lowest diameter: 200 nm) [Tan E P S & Lim C T. Physical properties of a single polymeric nanofiber. App Phys Lett. 2004; 84(9):1603-5; Liu L, et al. Tensile mechanics of electrospun multiwalled nanotube/poly(methyl methacrylate). Adv Mater. 2007; 19(9):1228-33; Tan E P S & Lim C T. Novel approach to tensile testing of micro- and nanoscale fibers. Rev Sci Inst. 2004; 75(8):2581-5; Tan E P C et al. Tensile testing of a single ultrafine polymeric fiber. Biomaterials. 2005; 26(13):1453-6; Tan E P S et al. Tensile test of a single nanofiber using atomic force microscope. App Phys Lett. 2005; 86:073115-3; Tan E P S & Lim C T. Effects of annealing on the structural and mechanical properties of electrospun polymeric nanofibers. Nanotechnology. 2006; 17:2649-54]. The fiber diameters are provided in the aforementioned techniques to highlight the fact that these fibers are still visible under bright field microscopy and with some care can be manipulated to the desired locations and post processed for boundary conditions. Additionally the methods outlined before are cumbersome and are not engineered to test a large number of samples, as they do not provide a robust platform for repeatable experimental conditions from one sample to the next.

Dynamic flexural vibrational behavior of cantilevers can be employed for sensing applications where the sensitivity of the cantilevers can be increased by fabricating cantilevers down to sub-micron diameter ranges with polymeric materials. In addition to their lower fabrication costs, polymeric cantilevers offer several advantages over commercially available microfabricated silicon based cantilevers. In particular, a wide range of polymers can be used to attain different sensor properties. Furthermore, the polymeric cantilevers can undergo higher deformations thereby increasing the overall sensitivity of the sensor systems [Tan E P S & Lim C T. Nanotechnology. 2006; 17:2649-54]. However, polymeric cantilevers are soft and fragile and can be exceedingly difficult to incorporate as real devices. The survivability of such a device is greatly improved by increasing the number of functional polymeric cantilevers within the device. Using polymeric cantilevers in real life applications requires fabricating polymeric cantilevers with known geometries with appropriate boundary conditions (fixed-fixed or fixed-free). Response of polymeric fibers can then be measured by exciting the fibers and measuring their deflection using lasers [Tan E P S & Lim C T. Nanotechnology. 2006; 17:2649-54] or by measuring the change in the electrical properties [McFarland A & Colton J. Chemical sensing with micromolded plastic microcantilevers. J Micromech Sys. 2005; 14(6):1375-85].

Thus, in this Example we present our preliminary results on mechanical characterization of polymeric micro/nanofibers, which overcomes the limitations imposed by aforementioned techniques for characterization.

Experimental Setup and Results

Polymeric Fiber Manufacturing Setup:

The polymeric nanofiber arrays are deposited in highly aligned configurations in single or multiple layers with variable geometrical spacing between them as shown schematically in FIG. 1A micropipette spinneret is mounted perpendicularly to the substrate on a three degree of freedom manual stage (562 Series ULTRAlign™ Precision Multi-Axis Positioning Stages, Newport Inc., USA). The substrate is mounted on to a DC motor, which in turn is mounted onto a motorized three degree of freedom micropositioning stage (VP-25XA, Newport Inc., USA), essentially as described above.

Figure 39:
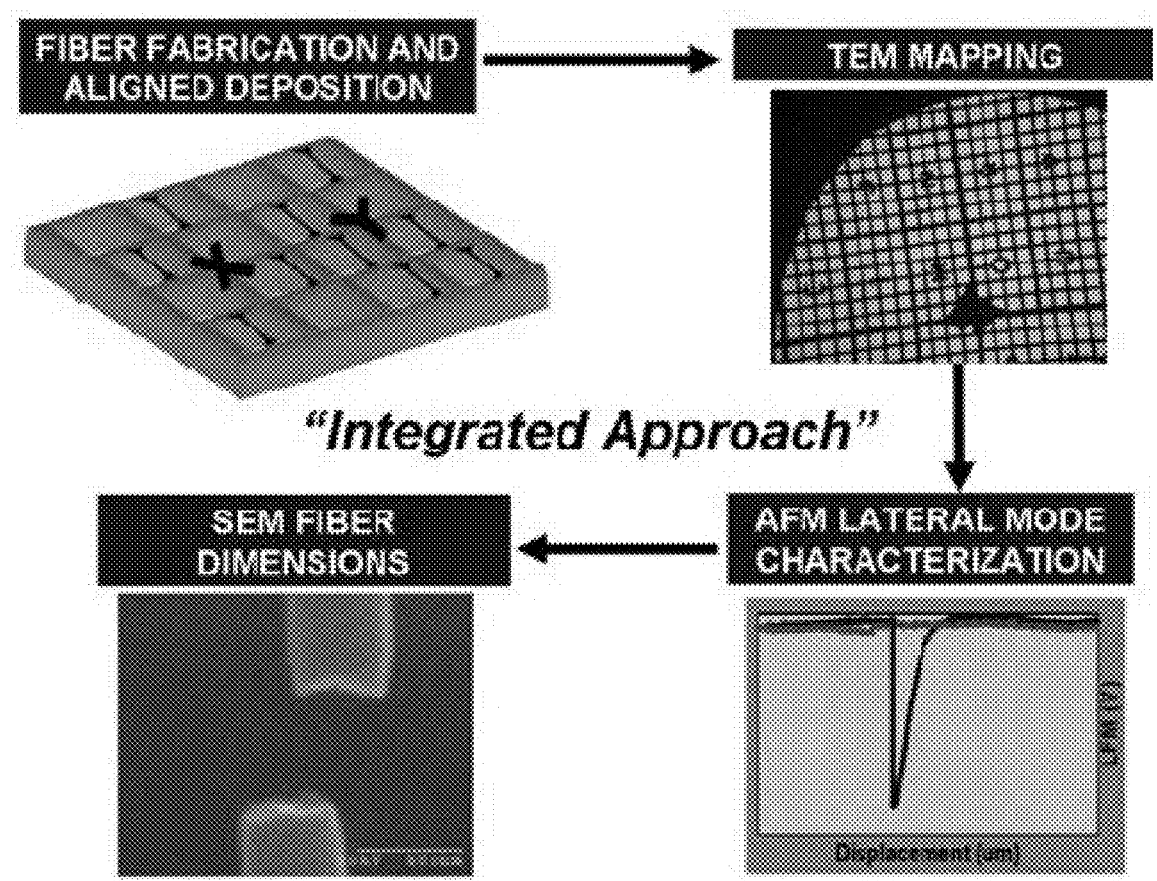
FIG. 39 is a schematic showing an integrated approach for aligned deposition and mechanical characterization of polymeric fibers.

Mechanical Characterization Strategy:

A robust and repeatable approach for aligned deposition of polymeric fibers with fixed-fixed boundary conditions in large number of samples with varying diameters is developed. In the developed integrated approach (FIG. 39), polymeric fibers are first deposited on TEM grids. These fibers are then mapped for location on the TEM grids and approximate diameter calculations using TEM. Subsequently, the TEM grids are positioned for lateral force microscopy using AFM. Once the fibers have been mechanically characterized, SEM measurements are performed to obtain accurate fiber dimensions. The main theme of this section is to demonstrate the establishment of a robust and repeatable platform for aligned deposition of a large sample of polymeric fibers having diameters ranging from sub-50 nm to microns with fixed-fixed boundary conditions without external manipulation for future detailed mechanical characterization studies.

Figure 40A:
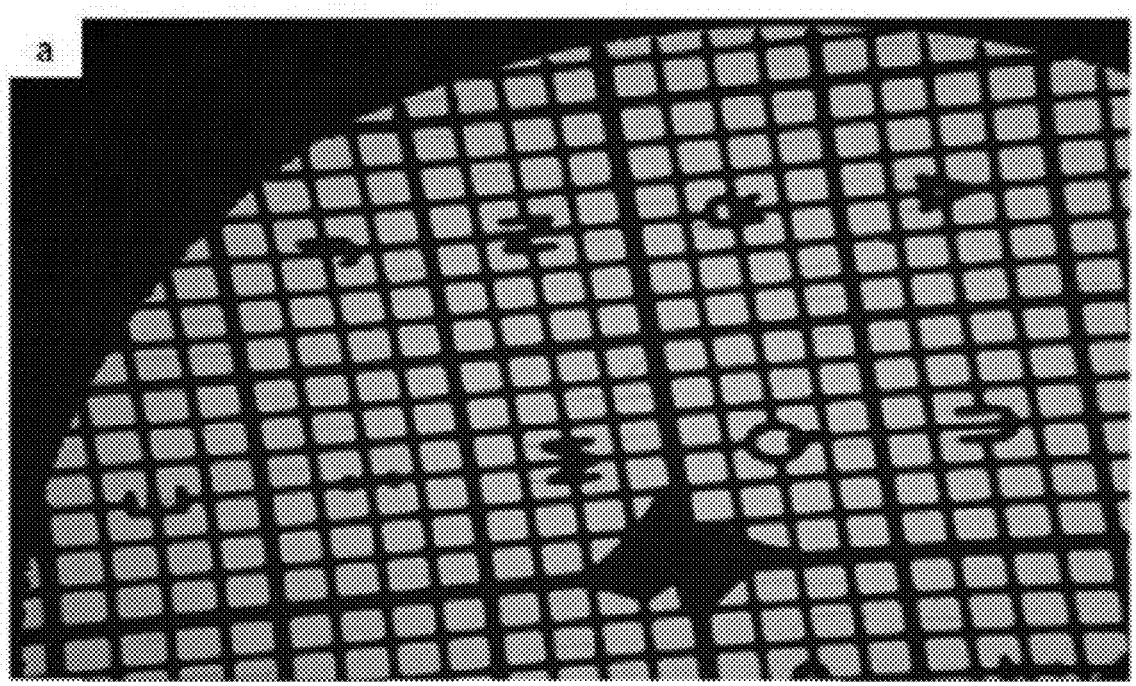
FIGS. 40A-40B show (A) mapped fibers on transmission electron microscopy grids and (B) a schematic illustrating the approach for performing lateral mode microscopy using atomic force microscopy (AFM).
Figure 40B:
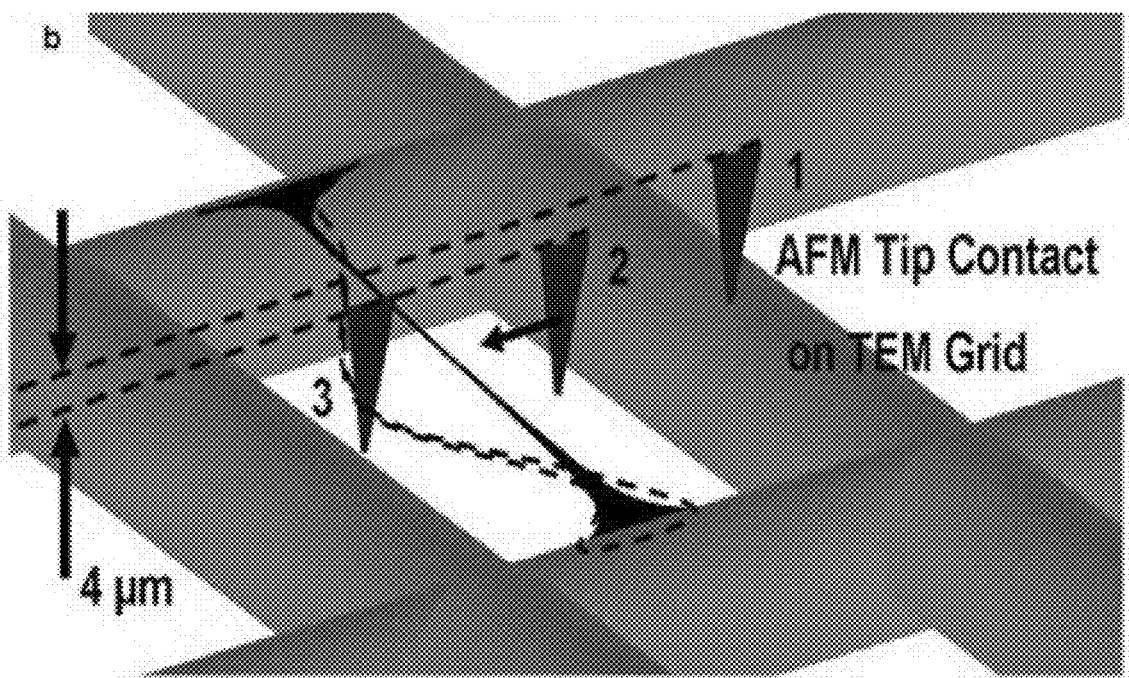
Figure 41:
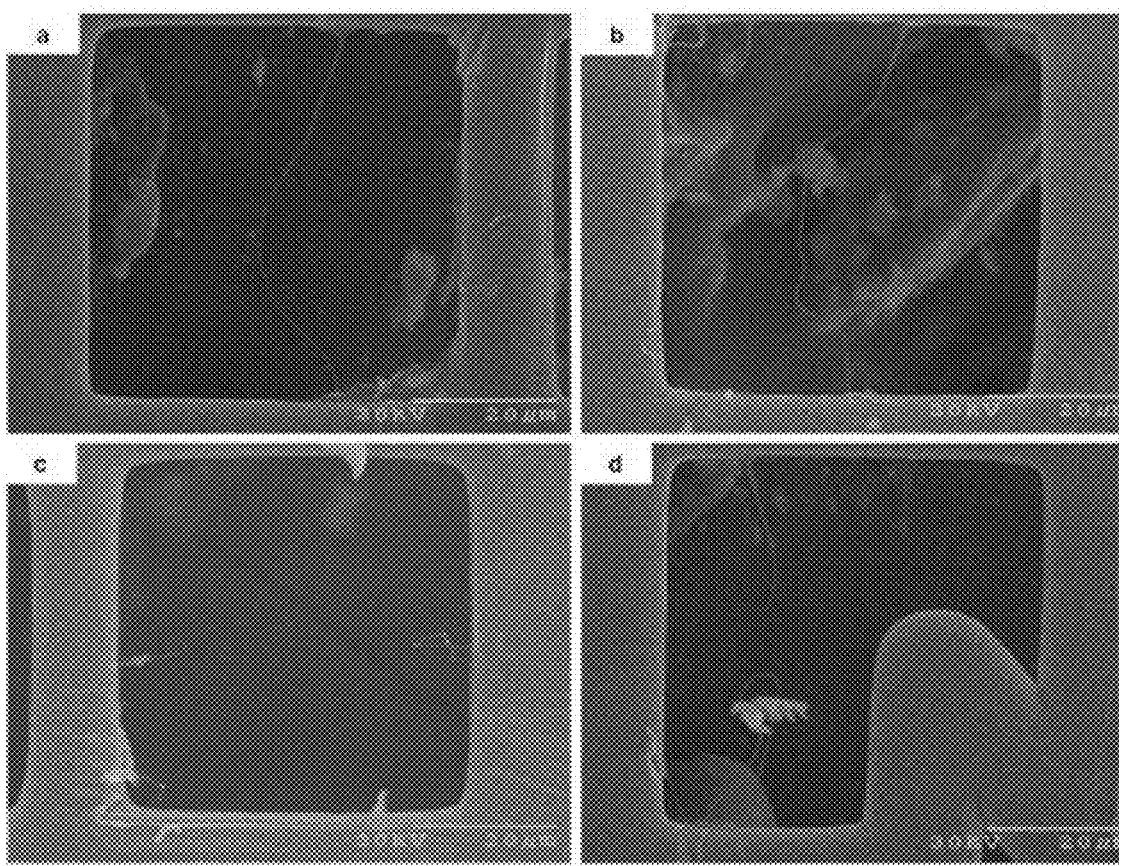
FIGS. 41A-41D show the existence of fixed-fixed boundary conditions for (A-B) plastically deformed fibers, and (C-D) fractured fibers.
Figure 42:
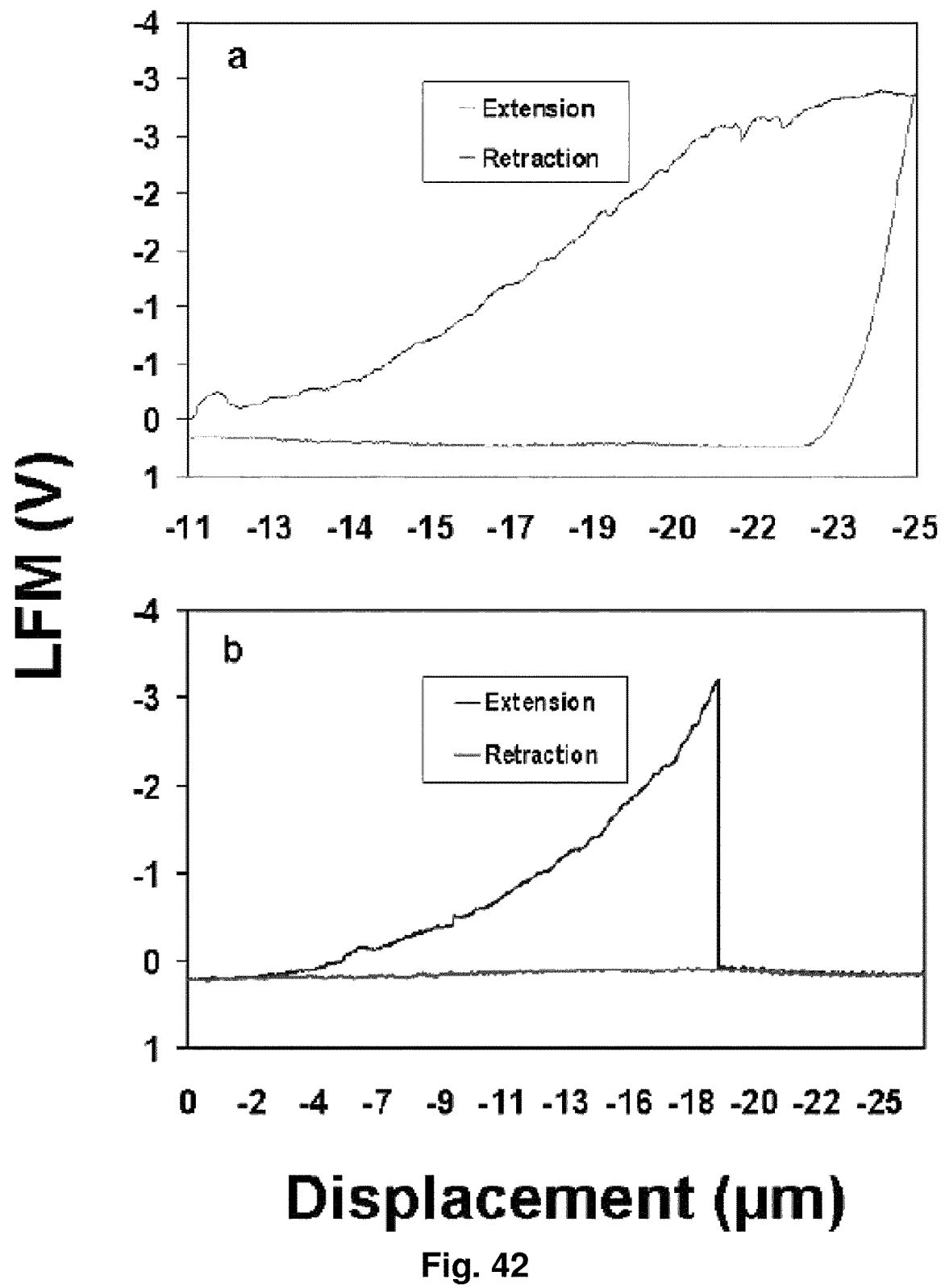
FIGS. 42A-42B are typical lateral force microscopy curves from AFM for (A) plastically deformed fiber, and (B) fractured fiber

After the fibers have been deposited on the grids, they are mapped for approximate locations and diameters as shown in FIG. 40A. The grids are then placed under the AFM and the probe tip is brought in contact with the copper grid and positioned approximately 4 μm below the grid and next to the fiber as shown in FIG. 40B. The probe is then moved in lateral mode to plastically deform or fracture the fibers as shown in FIG. 41. At low deformation rates, PS fibers can undergo large plastic deformations before breakage and exhibit increased toughness compared to PMMA fibers. Hence, an experimentally determined deformation rate of 5 μm/sec was used for all experiments. Existence of fixed-fixed boundary conditions is demonstrated by the post deformation history of the fibers as observed in the SEM images for both the plastically deformed and fractured fiber. The grids are then removed and accurate fiber dimensions are obtained under the SEM. Typical AFM curves for plastically deformed and fractured fibers are shown in FIG. 42.

Figure 43A:
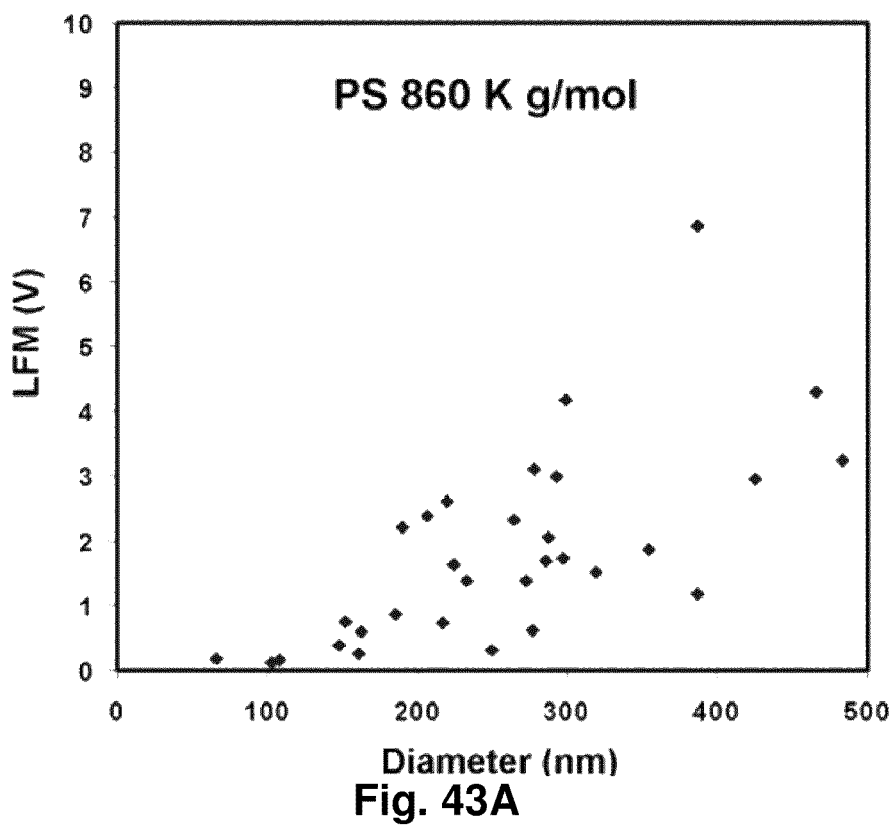
FIGS. 43A-43B show lateral force microscopy of individual suspended fibers using the integrated approach for (A) PS and (B) PMMA.
Figure 43B:
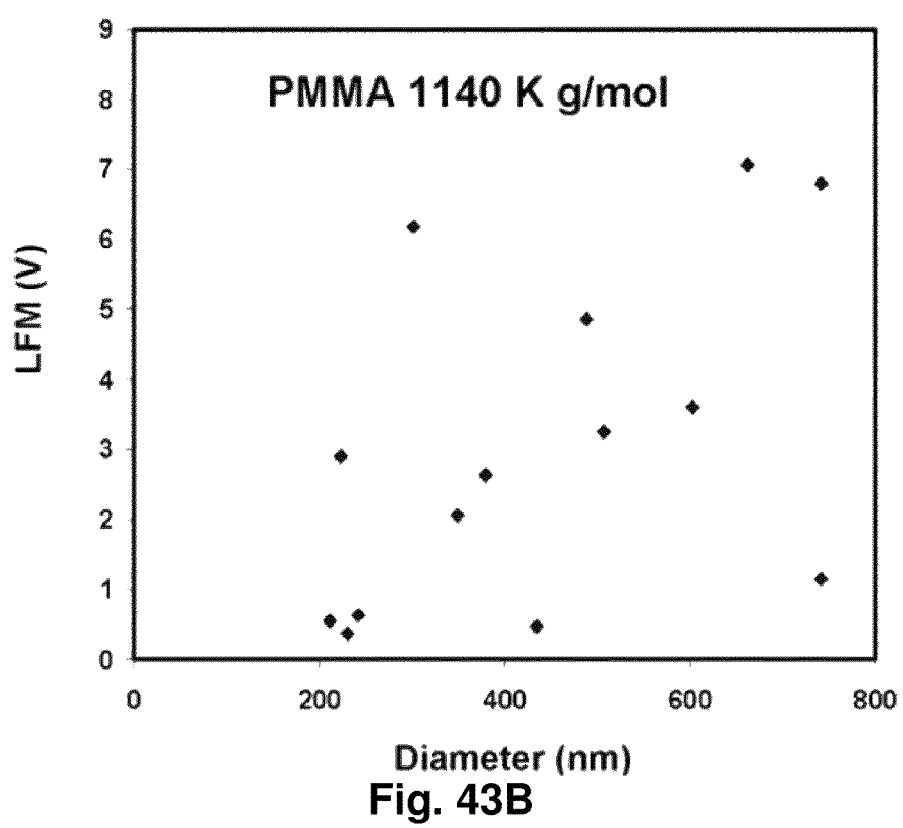

The integrated approach has been used to qualitatively determine the fracture behavior of PS 860K g/mol and PMMA 1150 Kg/mol polymeric fibers as shown in FIGS. 43A-43B. It is observed that the fracture AFM voltage decreases with the decrease in the fiber diameter. The values presented in this paper are reported exclusively in AFM voltages, as the LFM signal is found to be noisy with large drift, which can introduce errors in the deterministic measure of material properties.

Figure 44:
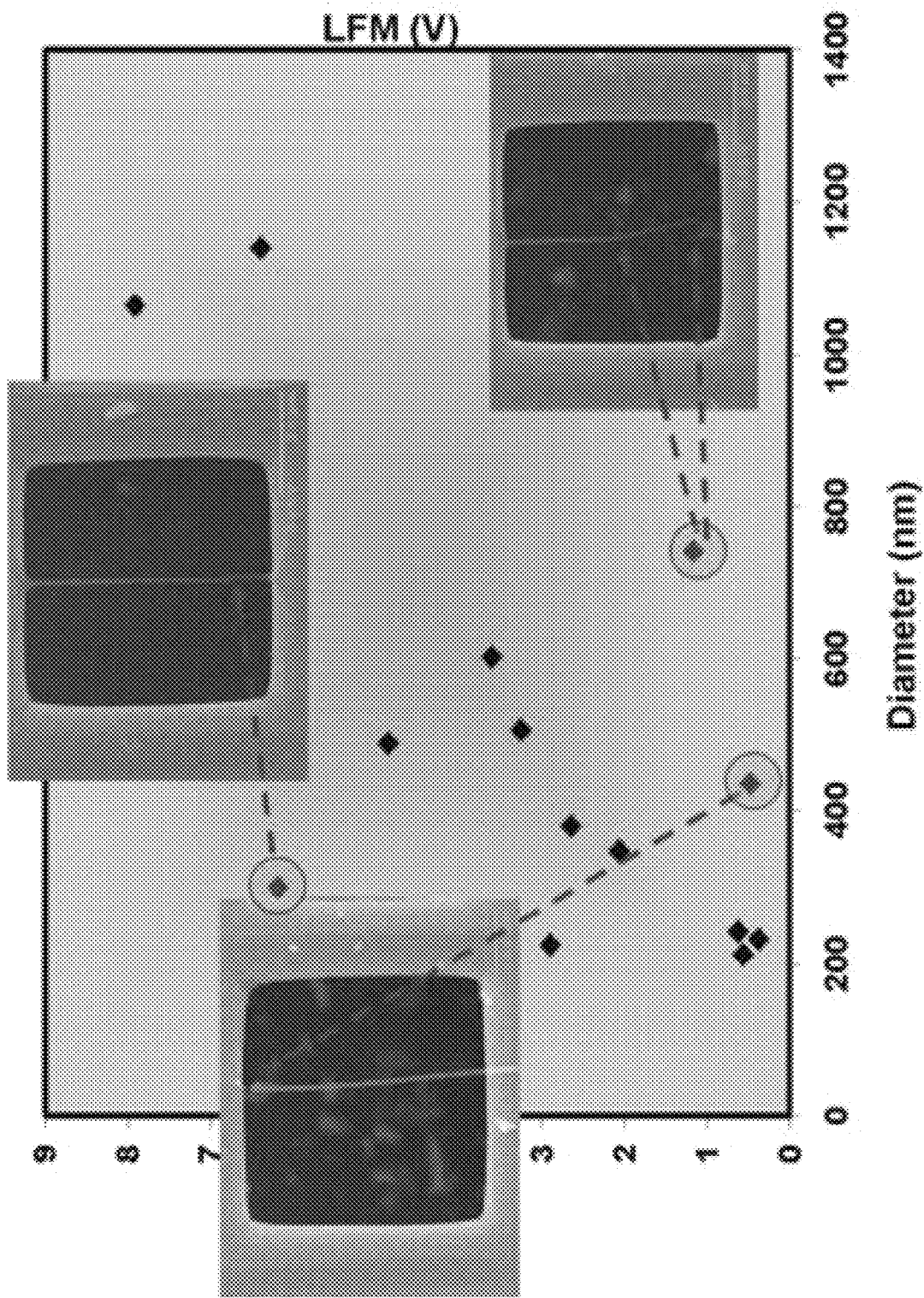
FIG. 44 shows post lateral force microscopy data analysis using sem demonstrating points of erroneous data.

The deformation behavior of polymeric materials is drastically different than the behavior exhibited by silicon, gold or other metallic wires. This makes mechanical characterization very challenging and extremely difficult at reduced length-scales and warrants a large number of samples. For example, the data shown for PMMA in FIG. 43B has points which are erroneous due to either improper boundary conditions or the polymeric fiber fracturing at the wrong place or developing multiple fracture points as shown in FIG. 44. As a cautionary note, these points should not be included. Thus, post processing using SEM not only provides accurate dimensions on the fiber, but also enables determining the quality of the data obtained. Finally it is interesting to compare the fracture behavior of two polymeric systems PS and PMMA. PS undergoes large strain deformation, whereas PMMA undergoes brittle fracture.

Polymeric Cantilevers:

In this section, we demonstrate the deposition of aligned micron and sub-micron PMMA fiber arrays with fixed-free boundary conditions for establishing a pathway for fabricating novel sensors composed of aligned polymeric fibers with high density.

Figure 45A:
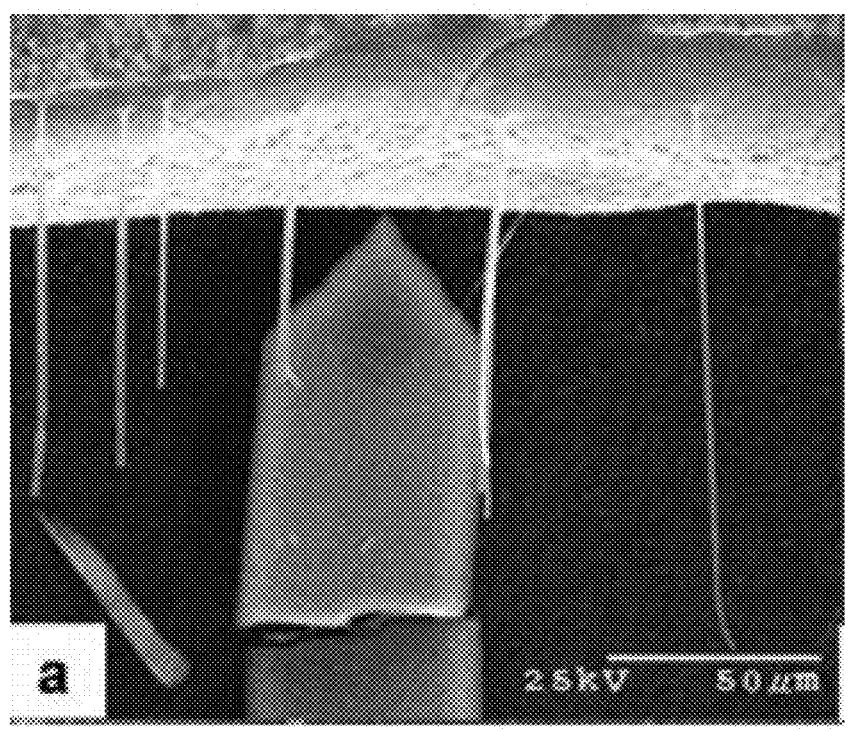
FIGS. 45A-45B are scanning electron micrographs of PMMA fibers brittle fractures using an AFM probe tip.
Figure 45B:
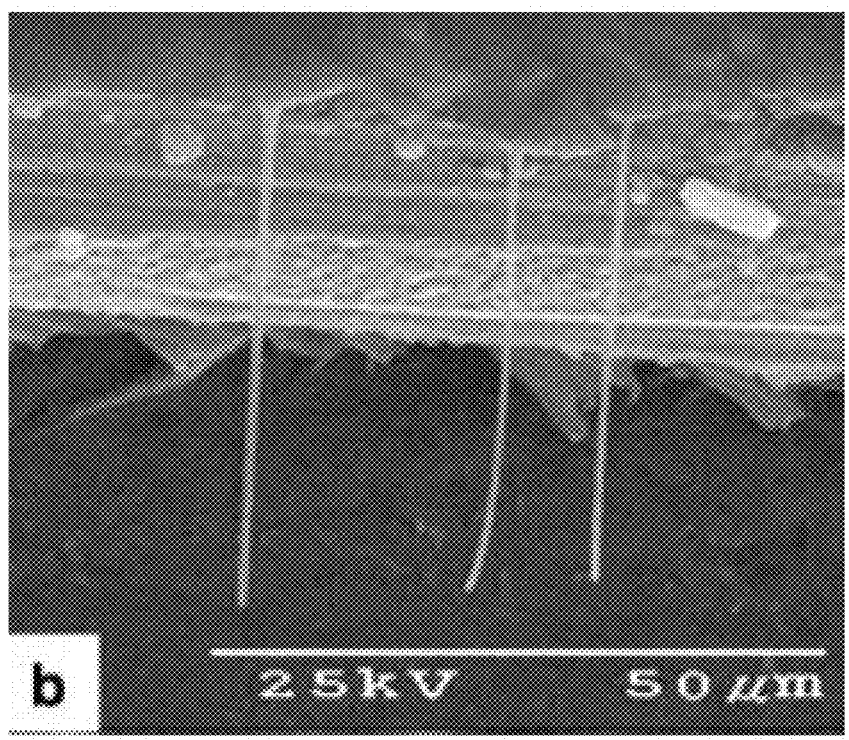

The aligned PMMA fiber arrays were deposited on a piezo-electric shaker and super glue was applied on one end of the fibers to achieve a fixed boundary condition. Suspended one-dimensional fiber cantilevers are obtained by breaking the fibers using an atomic force microscope (DI 3100, Veeco) in the lateral microscopy mode with a high stiffness non-contact AFM probe (NanoWorld AG, NCH, stiffness 42 N/m) in open loop as shown in FIGS. 45A-45B. The probe tip is moved laterally at high speeds exceeding 10 μm/sec to achieve brittle fracture of fibers.

In conclusion, this example presents and establishes a new manufacturing platform for precise deposition of aligned micro/nanofiber arrays with either fixed-fixed or fixed-free boundary conditions for mechanical characterization. Polymeric fibers having diameters ranging from sub-50 nm to sub-micron and several millimeters in length are deposited in accordance with theoretical predictions from polymer physics. A new mechanical characterization technique called 'integrated approach' has been demonstrated, which precisely deposits fibers with fixed-fixed boundary conditions in known locations on commercially available TEM grids. The fibers are mapped for approximate locations and AFM lateral force microscopy is performed to determine the fracture strength. Accurate fiber dimensions and erroneous data points are then determined using SEM. Additionally, a strategy for fabricating polymeric cantilevers is outlined. The micro/nanofiber manufacturing and characterization suite presented in this example can be easily extended to other polymeric systems and promises to aid in the development of next generation micro/nano enabled applications employing polymeric fibers.

Example 9

Fabrication of Single and Multi-Layer Fibrous Biomaterial Scaffolds for Tissue Engineering For regenerative medicine applications, we need to expand our understanding of the mechanisms by which nature assembles and functionalizes specialized complex tissues to form a complete organism. The first step towards this goal involves understanding the underlying complex mechanisms of highly organized behavior spanning not only diverse scientific fields, but also nano, micro and macro length-scales. For example, an engineered fibrous biomaterial scaffold possessing the hierarchal spatial properties of a native extracellular matrix (ECM) can serve as a building block upon which living cells are seeded for repair or regeneration. The hierarchical nature of ECM along with the inherent topological constraints of fiber diameter, fiber spacing, multi-layer configurations provide different pathways for living cells to adapt and conform to the surrounding environment. Our Spinneret based Tunable Engineered Parameters (STEP) technique to deposit biomaterial scaffolds in aligned configurations has been used for the first time to deposit single and multi-layer biological scaffolds of fibrinogen.

Fibrinogen is a very well established tissue engineering scaffold material, as it improves cellular interactions and allows scaffold remodeling compared to synthetic polymers. Current state-of-the-art fiber deposition techniques lack the ability to fabricate scaffolds of desired fiber dimensions and orientations and in this study we present fabrication and aligned deposition of fibrinogen fiber arrays with diameters ranging from sub-200 nm to sub-microns and several millimeters in length. The fabricated scaffolds are then cultured with pluripotent mouse C2C12 cells for seven days and cells on the scaffolds are observed to elongate resembling myotube morphology along the fiber axis, spread along intersecting layers and fuse into bundles at the macro scale.

Additionally, we demonstrate the ability to deposit poly (lactic-co-glycolic acid) (PLGA), Polystyrene (PS) biomaterial scaffolds of different diameters to investigate the effects of topological variations on cellular adhesion, proliferation and migration. Previous studies have indicated cells making right angle transitions upon encountering perpendicular double layer fibers and cellular motion is thwarted in the vicinity of diverging fibers. Current ongoing studies are aimed at determining the effects of fiber diameter and fiber spacing on mouse C2C12 cellular adhesion and migration, which are envisioned to aid in the design of future scaffolds for tissue engineering possessing appropriate material and geometrical properties.

For regenerative medicine applications, we need to expand our understanding of the mechanisms by which nature assembles and functionalizes specialized complex tissues to form a complete organism. The first step in engineering biological tissues involves understanding the underlying complex mechanisms of highly organized behavior spanning not only diverse scientific fields, but also nano, micro and macro length-scales. Artificially generated hierarchical three-dimensional (3D) scaffolds built out of synthetic or native polymeric systems are finding increasing interest in biomedical and biotechnological applications as they are used to promote cell adhesion, differentiation, and proliferation and as a mechanism to organize and direct the growth of cells and natural extracellular matrices (ECM). A recent review reports in detail potential applications for scaffolds: tissue engineering, controlled drug release, dressings for wound healing, medical implants, nanocomposites for dental applications, molecular separation, biosensors, and preservation of active biological compounds [Zhang Y et al. Recent development of polymer nanofibers for biomedical and biotechnological applications. J Mater Sci. 2005, 16:933-46].

ECM provides the necessary anchorage and support structure for cells, which in turn dictates the dynamic behavior of attached cells. A scaffold possessing the native properties of ECM should address the design constraints at various levels of hierarchy, as native ECM consisting of networks of fibers having diameters ranging from 50 to 500 nm [Silver F H &

Christiansen D L, Biomaterials Science and Biocompatibility, Springer-Verlag, New York, 1999] can be divided into four distinct spatial domains: macro scale (>1 mm), micrometer scale (1 µm-1 mm), sub-micrometer scale (100 nm-1 µm) and finally nanoscale (<100 nm). A unit block of the engineered scaffold at each level of abstraction having corresponding dimensions should mimic the ECM, thus perhaps providing a pathway to successful tissue engineering. At the macroscale, the arrangement of scaffold unit blocks should enable multitude of cells fusing into bundles, while at the microscale, scaffold unit block dimensions equaling that of individual cellular dimensions along with the topological constraints dictate individual cellular response.

Fabricating fibrous scaffolds is one promising component for a tissue engineering approach and equally important is shaping them to spatially resemble living tissues. Numerous studies have indicated the importance of key engineered parameters: fiber diameter, fiber alignment, geometrical fiber spacing, scaffold mechanical strength, fiber roughness and topological constraints of scaffolds. Small diameter fibers having high specific area best mimic ECM and are conducive to tissue growth, due to increased aqueous solubility, bio-recognition, and polymer chain exposure [Flemming R G, et al. Effects of synthetic micro- and nano-structured surfaces on cell behavior, Biomaterials. 1999; 20:573-88] while fiber orientation controls cell shape, physiological function, and organ architecture [Zhong S, et al. An aligned nanofibrous collagen scaffold by electrospinning and its effects on in vitro fibroblast culture, J Biomed Mater Res A. 2006; 79:456-63; Xu, J. et al. Microfabricated quill-type surface patterning tools for the creation of biological micro/nano arrays. Biomed Microdevices, 2004; 6:117-23]. Scaffold pore size is an important determinant of cell mobility within a scaffold as cell proliferation is inhibited in scaffolds with pores that are too small [Pham Q P et al. Electrospinning of polymeric nanofibers for tissue engineering applications: a review. Tissue Eng. 2006; 12:1197-211]. Biomaterial scaffolds with rough surfaces influence cell attachment and behavior [Miller D C et al. Mechanism(s) of increased vascular cell adhesion on nanostructured poly(lactic-co-glycolic acid) films, J Biomed Mater Res A. 2005; 73:476-84 and Thapa A et al. Nano-structured polymers enhance bladder smooth muscle cell function", Biomaterials. 2003; 24:2915-26], and contact guidance using topological cues for the control of cell mobility has been used to limit cell migration to specific sites in the scaffold [Norman J J & Desa T A. Methods for fabrication of nanoscale topography for tissue engineering scaffolds. Ann Biomed Eng. 2006; 34:89-101]. These parameters constituting a vast design space with limited available information on their engineering limits along with their interdependency rules lead to a currently loose framework for designing fibrous biomaterial scaffolds.

Numerous techniques have been employed to fabricate artificial biological scaffolds for the aforementioned applications. Such processes include electrospinning, phase separation, self assembly, melt-blown and template synthesis. Electrospinning, a top-down approach, is a popular technique for the fabrication of biological scaffolds using a variety of materials. In electrospinning, an external electrostatic field is established between a pendant polymer solution droplet and a collector. When the electric field overcomes surface tension effects, fibers are formed and ejected towards the collector. This process is capable of producing fibers with small diameters ranging from microns to tens of nanometers and is relatively simple and reliable. However, the fibers produced are aligned chaotically, non-woven, and non-uniform in diameter. Special techniques have been used to create aligned electrospun fiber membranes in air or vacuum.

The Spinneret based Tunable Engineered Parameters (STEP) technique, described herein, deposits aligned single and multi-layer fibers having diameters ranging from sub-50 nm to microns and several millimeters in length. This allows unique investigation of topological constraints on cellular adhesion and dynamics. In the proposed technique continuous drawing of suspended polymer fibers involves extruding a solution of polymer dissolved in solvent from a micropipette and fiber formation occurs due to solvent evaporation from the extruded solution.

In this example, we demonstrate for the first time, continuous drawing of native fibrinogen fibers to fabricate single layer scaffolds. The scaffolds are then seeded with pluripotent mouse C2C12 cells, which are subsequently found to align along the fiber axis. Additionally, we present our preliminary investigations of the effect of topological constraints of single, intersecting fibers and beaded fibers on cellular migration and adhesion. On double layered constructs, cells are found to migrate and often make right angle transitions in the vicinity of intersecting fibers and are generally found to assume a cuboidal morphology.

Experimental Results

Figure 46:
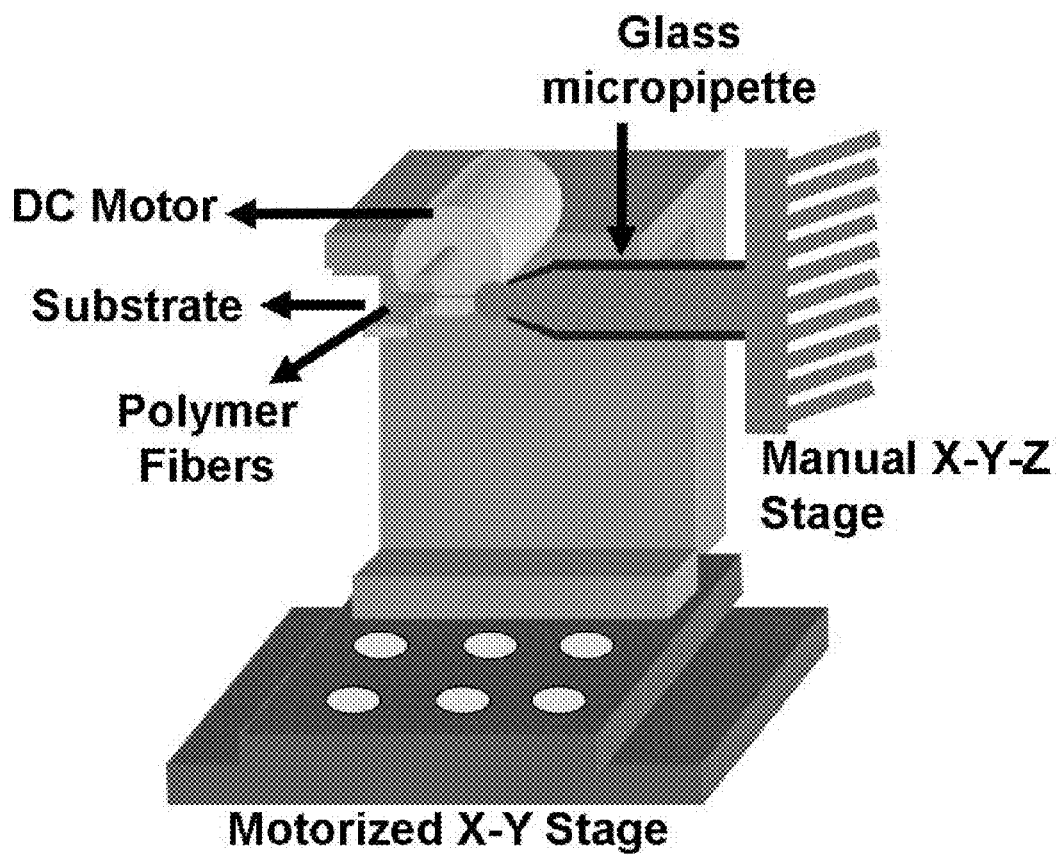
FIG. 46 is a schematic depicting an experimental setup for aligned deposition of polymeric fiber arrays.

Manufacturing Technique: Experimental Setup and Parameters for Drawing Suspended Nanofibers A micropipette is mounted on a 3 DOF manual positioner and is fixed perpendicular to the fiber uptake substrate. The fiber uptake substrate is mounted on a DC motor, which in turn is mounted on a 3 DOF motorized nanopositioner (Newport VP series) as shown in FIG. 46. Fibers are drawn continuously on the rotating substrate and the desired geometrical fiber spacing is achieved by controlling the vertical speed of the nanopositioner and by choosing an appropriate rotational speed of the DC motor. Multiple layers at desired orientations are fabricated by depositing fibers on top of previously deposited layer(s).

Scaffold Preparation:

Polymeric micro/nanofiber single and multi-layer scaffolds were prepared using different polymeric systems. PS ($M_w$ 1800K g/mol, dissolved in Xylene by 10%), PLGA (PURASORB:85-15 dissolved in chloroform by 10%) and human Fibrinogen (Aventis Behring, King of Prussia, Pa., USA) was dissolved in a solution of 1 part of Dulbecco's Modified Essential Medium (Base DMEM) and 9 parts of 1,1,1,3,3,3-hexafluoro-2-propanol (HFP; Sigma-Aldrich Chemical Solution) to a concentration of approximately 0.12 g/ml. [Wnek G E, et al. Electrospinning of Nanofiber Fibrinogen Structures, Nanoletters. 2003; 3(2):213-6] PLGA-Fibrinogen solutions were made by mixing the two individual solutions in a ratio of 4:6 parts respectively.

Prior to cell seeding, the scaffolds were sterilized by submersion in 100% ethanol for ten minutes. Excess ethanol was gently aspirated and the scaffolds were allowed to air dry for five minutes. To remove air and ensure that no ethanol remained beneath the sample, scaffolds were slid over a 2 µl bead of basal cell culture medium with 10% fetal calf serum and 1% penicillin/streptomycin (all cell cultures components from Invitrogen). To minimize the effects of capillary forces and increase the survivability of scaffolds, the samples were immobilized to tissue culture wells by contacting with a drop of silicone grease at the side. All scaffolds were seeded with C2C12 mouse myoblast precursor cells. Cells were seeded on scaffolds in basal growth medium and were incubated at 37° C., 5% $CO_2$ with humidity. Cells were allowed to attach for 4-5 hours and then 3 ml of basal media was added. Cells were then incubated for several days or imaged using time lapse microscopy using a Zeiss AxioPlan 2 microscope employing Axiovision Software.

Figure 47A:
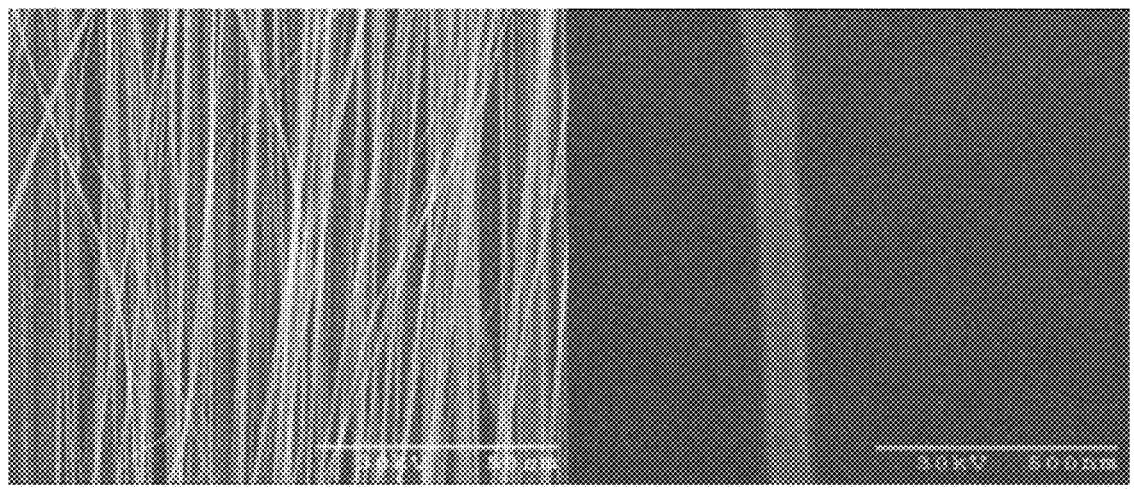
FIGS. 47A-47C are scanning electron micrographs of single layer oriented scaffolds of (A) fibrinogen, (B) fibrinogen-PLGA, and (C) mouse c2c12 cells seeded on fibrinogen-PLGA single layer scaffolds.
Figure 47B:
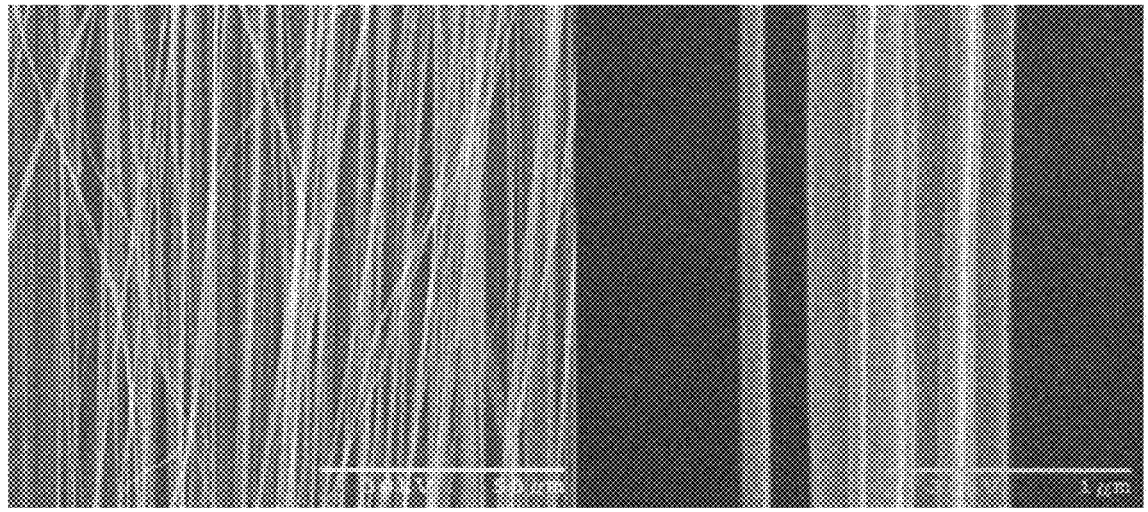
Figure 47C:
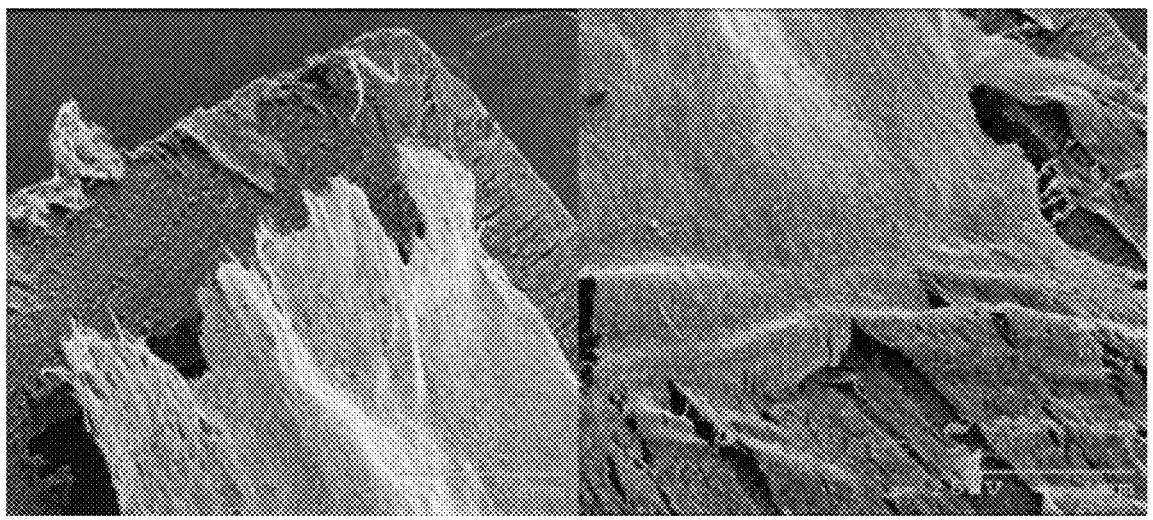

Different single and multi-layer fibrous scaffolds were prepared to investigate cellular behavior. We defined 'acceptable' fibers as smooth and uniform diameter fibers several millimeters in length. Limited success was achieved in fabricating pure fibrinogen fibers, as uniformity of diameter was not obtained as shown in FIG. 47A. Additionally, the diameter of fiber obtained was in the range of 500 nm to submicron. Upon mixing PLGA solution with fibrinogen, we were able to deposit smooth and uniform diameter (diameter: 100 nm-500 nm) single and multi-layer fibers as shown in FIG. 47B. Scaffolds of fibrinogen-PLGA mix were then seeded with C2C12 cells for 7 days and cells were observed to attach and integrate with the fibrous structures as shown in FIG. 47C (scaffold-cell structures delaminated from substrate during fixation process for SEM imaging).

Figure 48:
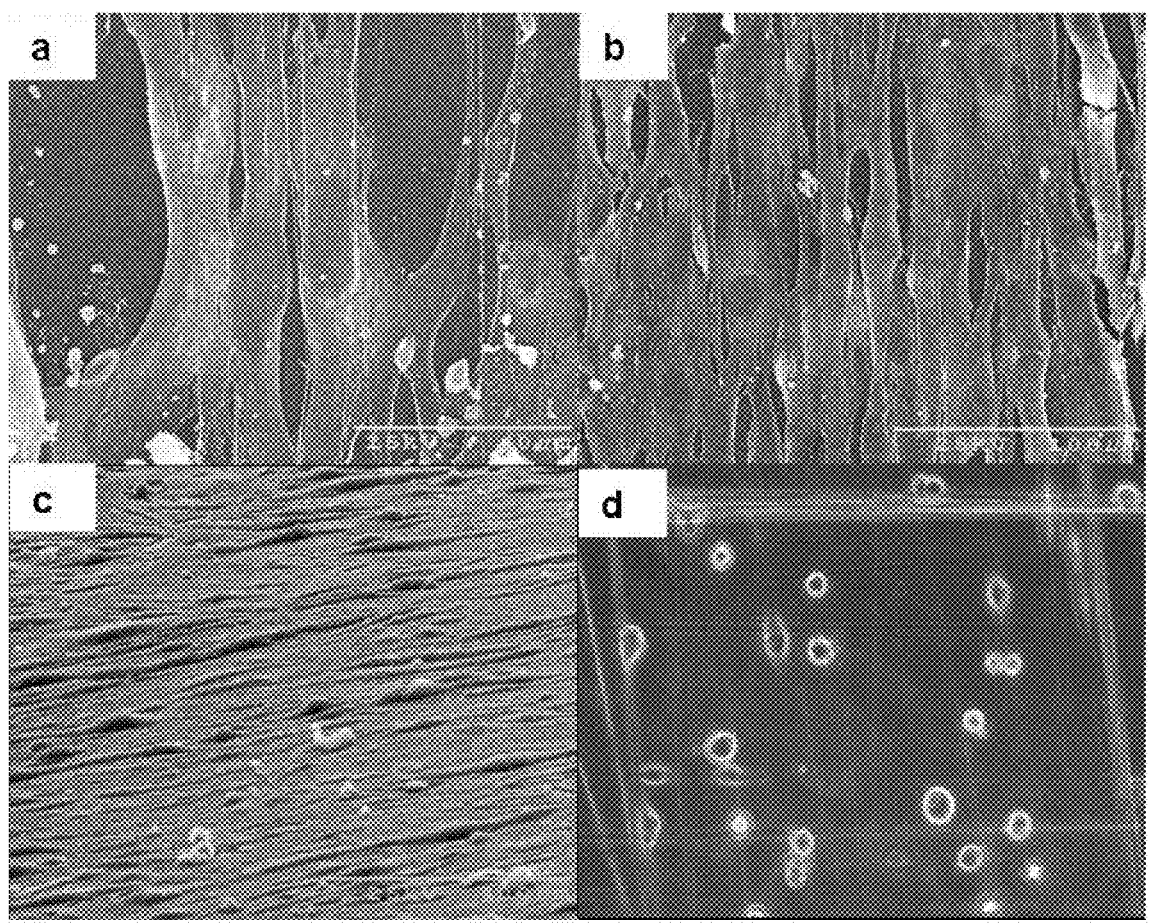
FIGS. 48A-48D are scanning electron micrographs of c2c12 cells attaining possible myotube morphology on single layer constructs (A-B) cellular alignment along fiber axis, (C) angled view showing cellular alignment, and (D) optical image of rounded morphology on multilayer scaffolds.

Single layer PS fibrous scaffolds with average fiber diameter of approximately 200 nm were spun on glass coverslips and C2C12 cells were seeded on the scaffolds for a period of 7 days. The cells were observed to align and elongate along the fiber axis attaining a morphology resembling myotubes as shown in FIG. 48A-48C. On intersecting fibers comprised of multi-layers, the cells were observed to obtain a rounded morphology as shown in FIG. 48D.

Investigation of Cellular Dynamics

The extra cellular matrix (ECM) provides structural support to cells in tissues and organs. Cellular adhesion to the scaffold is essential for diverse activities of cell migration, tissue organization and differentiation. Cell-matrix adhesion is predominantly mediated through integrin receptors. The communication between the cell and the matrix occurs through integrins in both inside-outside and outside-inside modes. In the outside-inside mode, integrin receptors regulate the intracellular signaling which is important for functions such as cellular spreading on underlying substrates. In the latter format of signaling, intracellular signaling can induce changes in integrin conformations which alter the ligand-binding with the ECM and lead to restructuring of the ECM. [Berrier A L & Yamada K M. Cell-Matrix Adhesion, J Cell Physiol. 2007; 213(3):565-73]. These signals are important for diverse activities which establish methods of cellular adhesion, agglomeration, spreading and directional migration. Thus, it becomes important to understand the effects of various substrates on cellular functions. For example, it is well known that directed cell migration is achieved by the establishment of cell polarity, which creates a leading and trailing edge. [Moissoglu K & Schwartz M A. Integrin signaling in directed cell migration. Biol Cell. 2006; 98:547-55] The leading edge undergoes membrane protrusions driven by actin polymerization which establishes new matrix contacts, whereas the trailing edge cell adhesion are disassembled to enable cellular motion in the leading direction. The effect of underlying substrate stiffness also affects cellular adhesion contacts. Thus, in principle it should be possible to establish this polarity by artificial incorporation of topological constraints in a substrate to achieve directed cellular motion. As a first step, this work is focused on providing aligned configurations of fibrous networks in single and multi-layers with a mix of diameters and geometrical spacing to investigate the behavior of cellular adhesion and migration.

Figure 49:
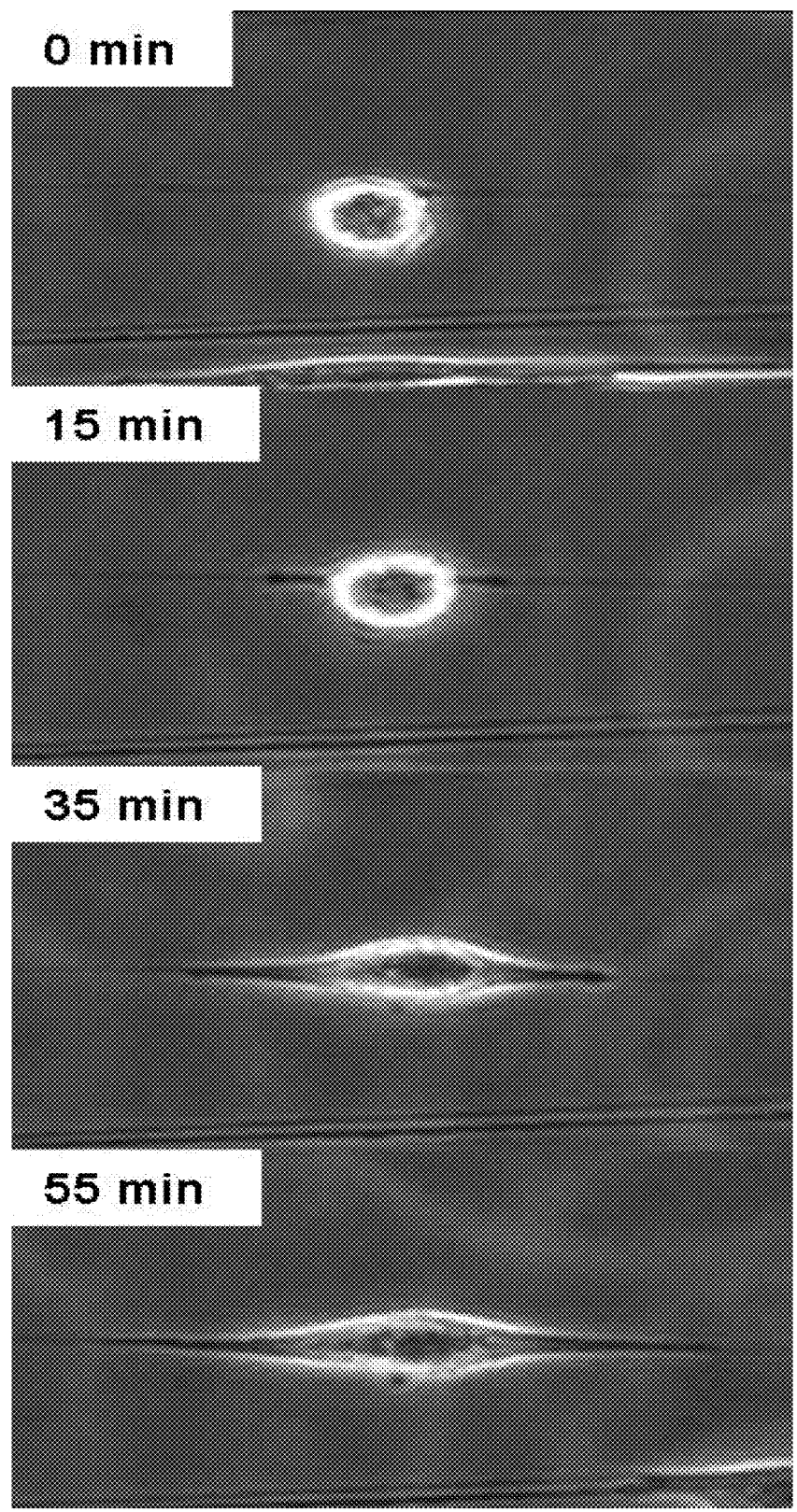
FIG. 49 shows optical time lapse photomicrographs of a single cell interaction with a single suspended fiber (magnification 10×)

Cellular interactions with a single suspended fiber are shown in time lapse microscopy images in FIG. 49. Initially the attached cell has rounded morphology, and the cell exhibits lamellipodial extrusions along the fiber. The cell achieves elongation along the fiber axis within an hour and shows no polarity for directed cellular motion along any direction.

Figure 50:
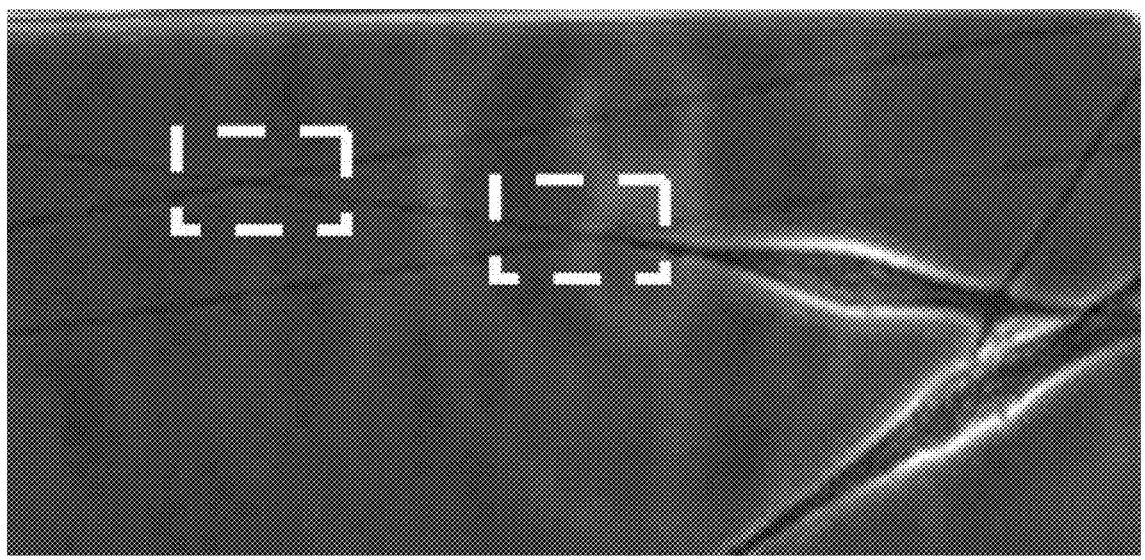
FIG. 50 is a photomicrograph showing single cell interactions with multiple interfaces (as shown by the dashed rectangle).
Figure 51:
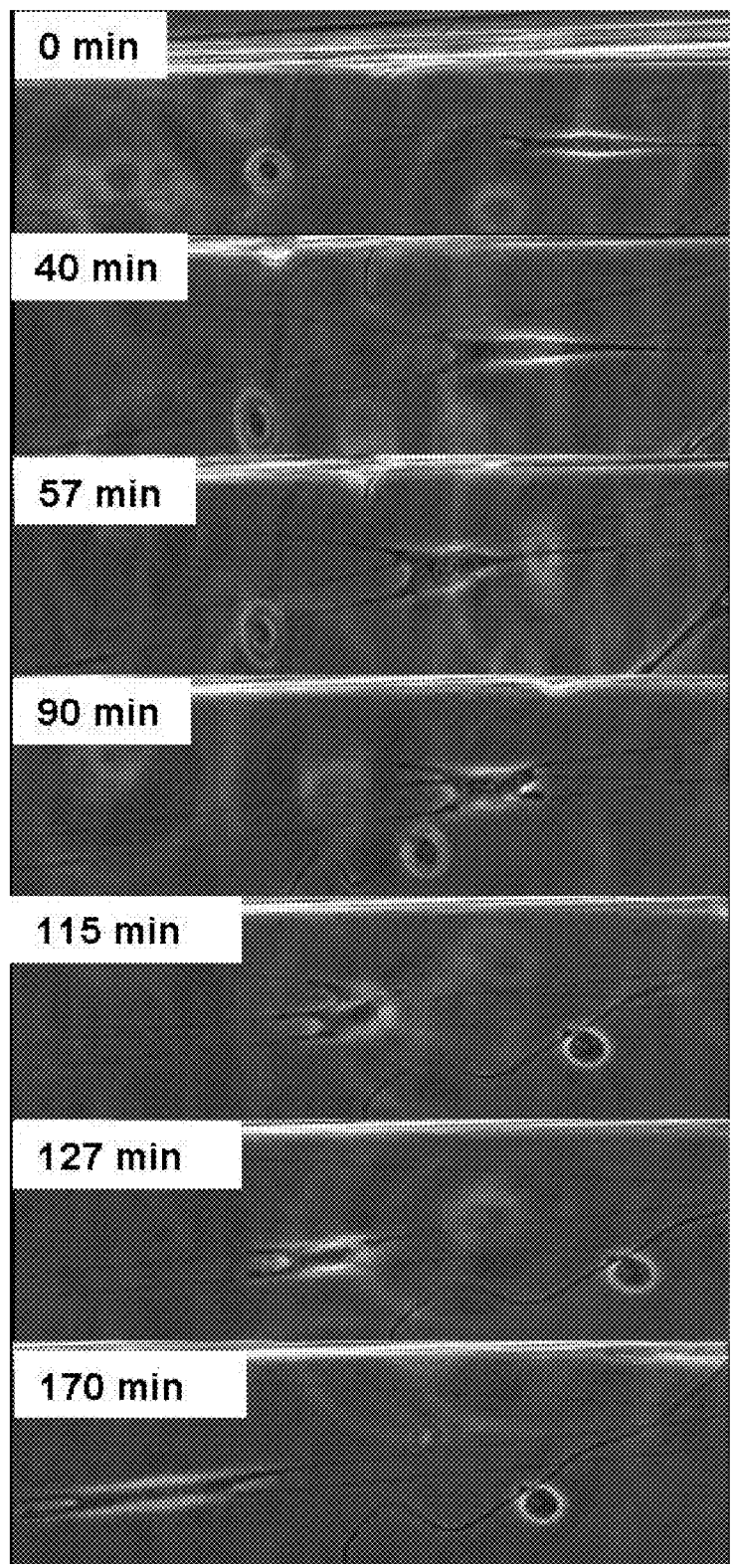
FIG. 51 shows optical time lapse photomicrographs of cellular interactions with multiple interfaces (magnification 10×).
Figure 52A:
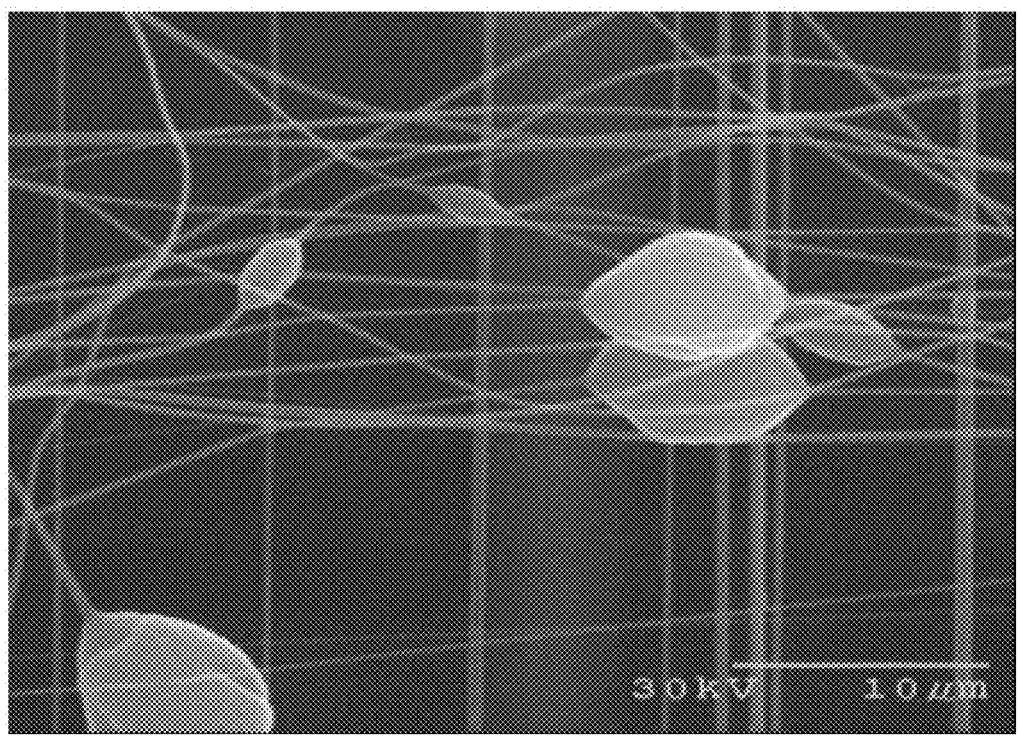
FIGS. 52A-B show cells seeded on beaded scaffolds: (A) scanning electron micrograph of beaded fibers and (B) area shown in dashed rectangle is shown in FIG. 53 at different time steps.
Figure 52B:
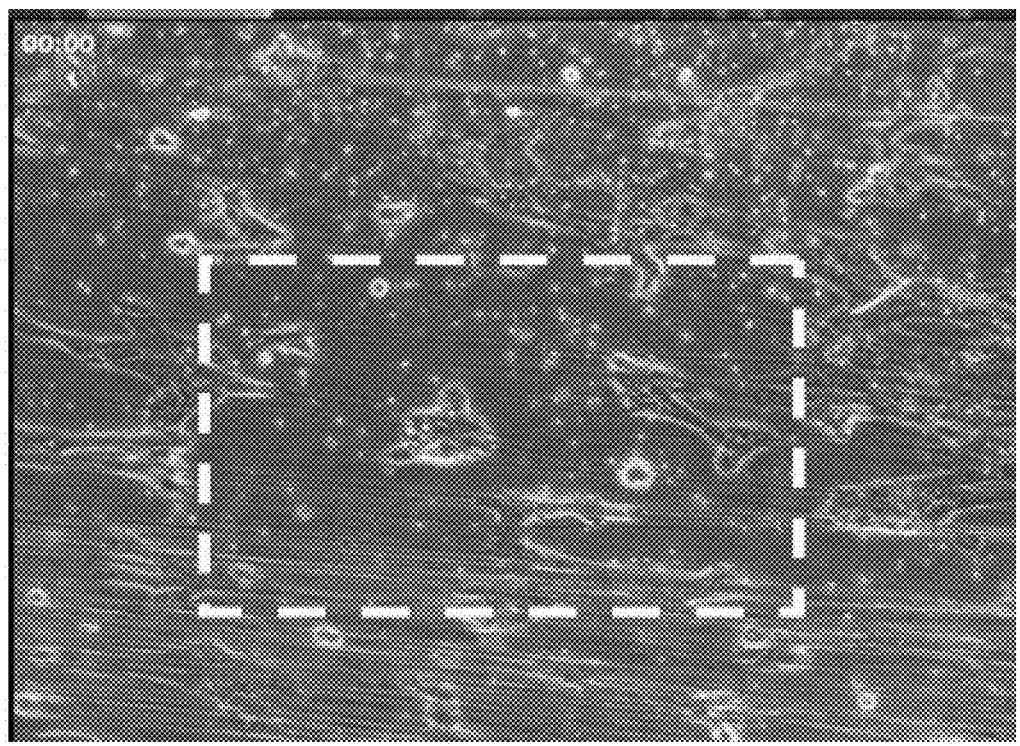
Figure 53:
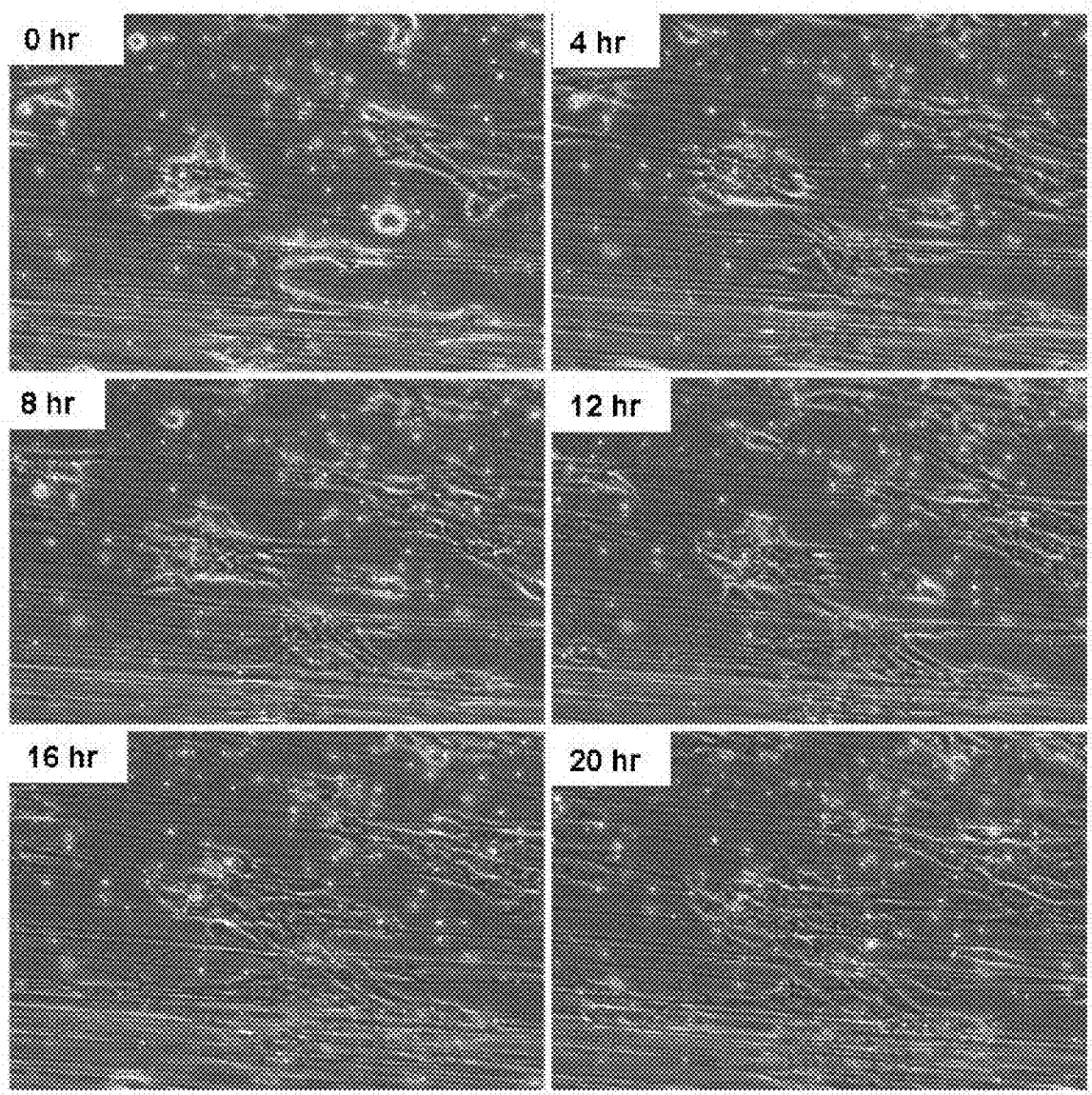
FIG. 53 shows optical time lapse photomicrographs of increased cellular adhesion and reduced cellular migration on scaffolds built of beaded fibers (magnification 5×).

In the presence of intersecting fibers providing multiple interfaces, cells exhibit multiple lamellipodial protrusions. Starting from the initial position of a cell interacting with a single fiber and having a leading edge (FIG. 50), time lapse microscopy was performed on the cell interacting with multiple surfaces as shown in FIG. 51. The spreading of a cell across multiple surfaces can be energetically prohibitive and the cell detaches from multiple surfaces and adheres to two surfaces and extends along them. Finally, cells were seeded on scaffolds built of fibers with topological constraints of beads, which were obtained at low polymeric concentrations as shown in FIG. 52A. Interestingly, cellular adhesion was found to be increased and the cellular migration was severely thwarted due to obstacles as demonstrated by time lapse microscopy over a period of 20 hours as shown in magnified images (FIG. 53) of central portion of FIG. 52.

The aforementioned studies shed important insights on cellular dynamics and can be used to generate a framework for the design of biomaterial scaffolds solely on geometrical constraints. Our future studies and aims are centered on carrying on detailed investigation of topological constraints of fiber diameter, fiber spacing, scaffold stiffness (single and multi-layer), and multiple interfaces, with the aim of increasing cellular adhesion, migration and eventually provide artificial pathways for directed cellular motion.

In conclusion, this example demonstrates fabrication of aligned fibers in single and multi-layers to serve as scaffolds for tissue engineering based applications. A method to control the diameter of the fibers based on selective choice of material and processing parameters is presented. Aligned deposition of fibers of native polymer fibrinogen is demonstrated for the first time and blends of PLGA and fibrinogen produce 100 nm diameter fibers. The PLGA-fibrinogen fibers show excellent compatibility to cellular adhesion. Cellular dynamics are investigated for single, intersecting and beaded fibers. Cells are observed to migrate preferentially on parallel fibers and exhibit higher adhesion but limited migration on beaded fibers.

Example 10

Hepatocytes on Aligned Fibrous Scaffolds

Figure 54:
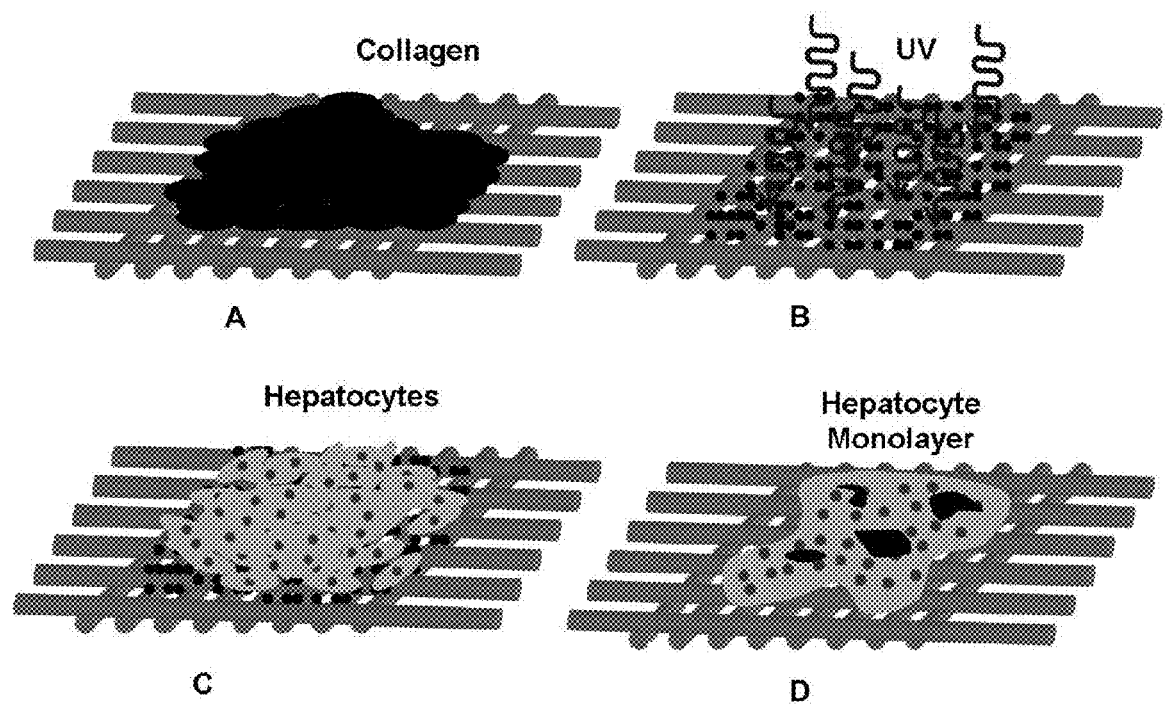
FIG. 54 is a schematic showing a non-limiting method of obtaining hepatocytes on aligned fibrous scaffolds.

As shown in FIG. 54, the constructs were coated with rat tail collagen (A) and allowed to dry overnight in tissue culture hood with a UV light on (B). The cells were plated by applying a 250 ul drop of cell suspension (500,00 cells/ml in EMEM media containing 50 ug/ml gentamicin and 50 ug/ml insulin) to the top of the construct and allowed to attach overnight (C). The media was changed to HGM containing 40 ug/ml HGF and 20 ug/ml EGF. Sufficient media was added to cover the constructs. Media was replenished every 2-3 days for the duration of the experiment. Cells were observed to form 'acrobatic' monolayers on the scaffolds (D).

Figure 55A:
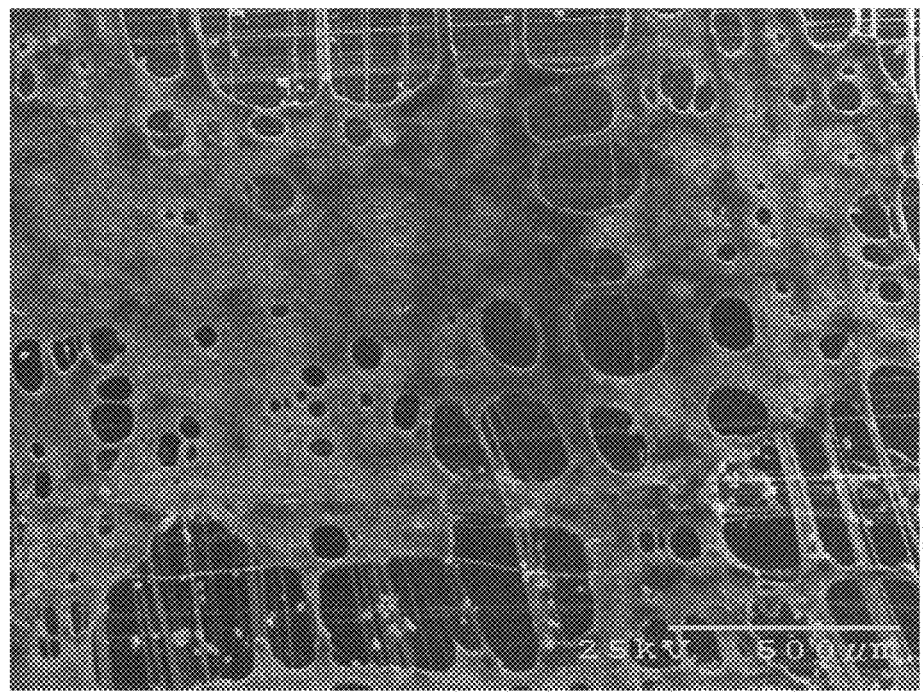
FIGS. 55A-55B are scanning electron micrographs of hepatocytes on criss-crossed fibrous scaffolds.
Figure 55B:
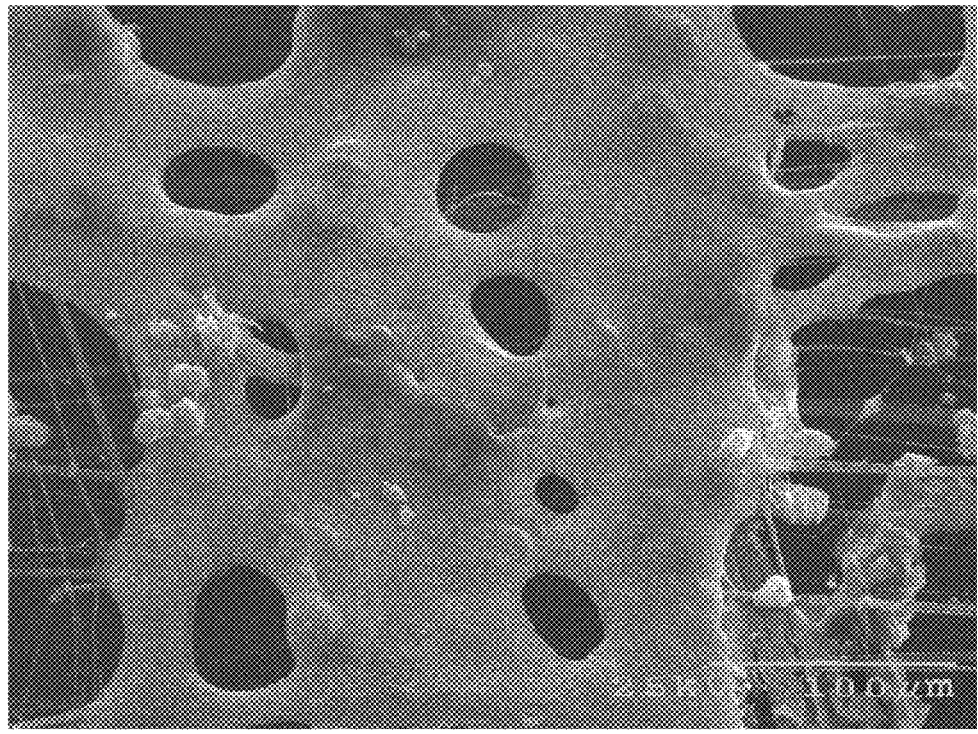
Figure 56A:
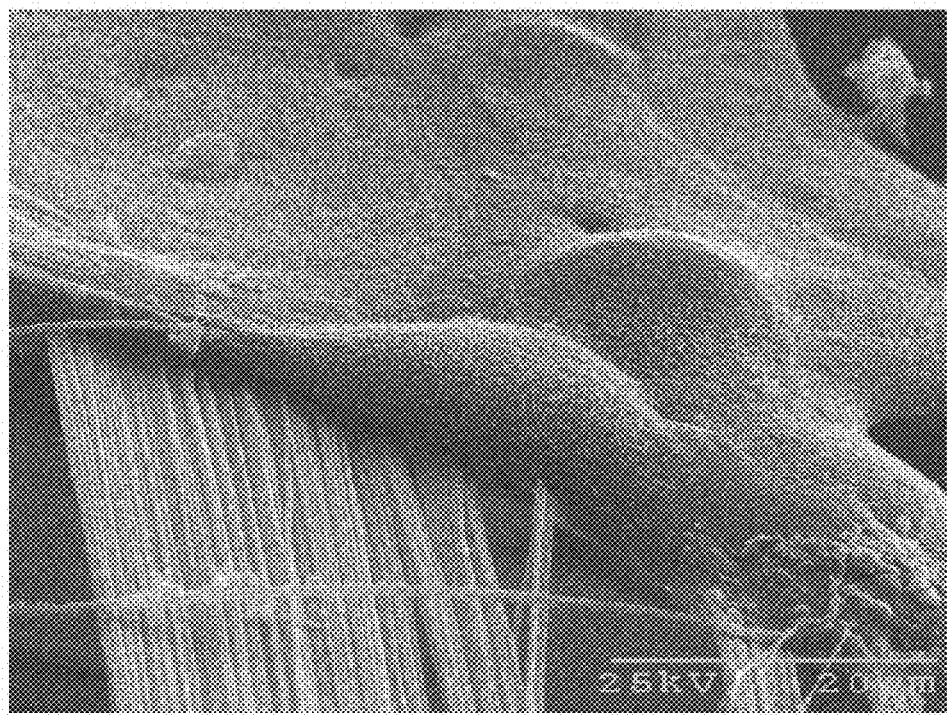
FIGS. 56A-56B are higher magnification scanning electron micrographs of hepatocytes on fibers.
Figure 56B:
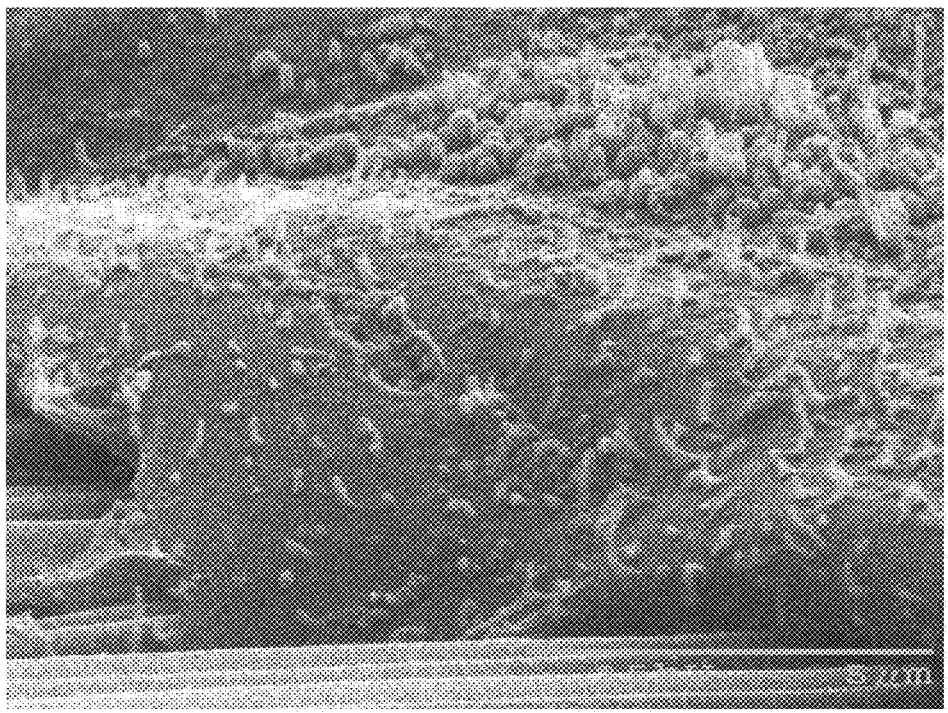
Figure 57:
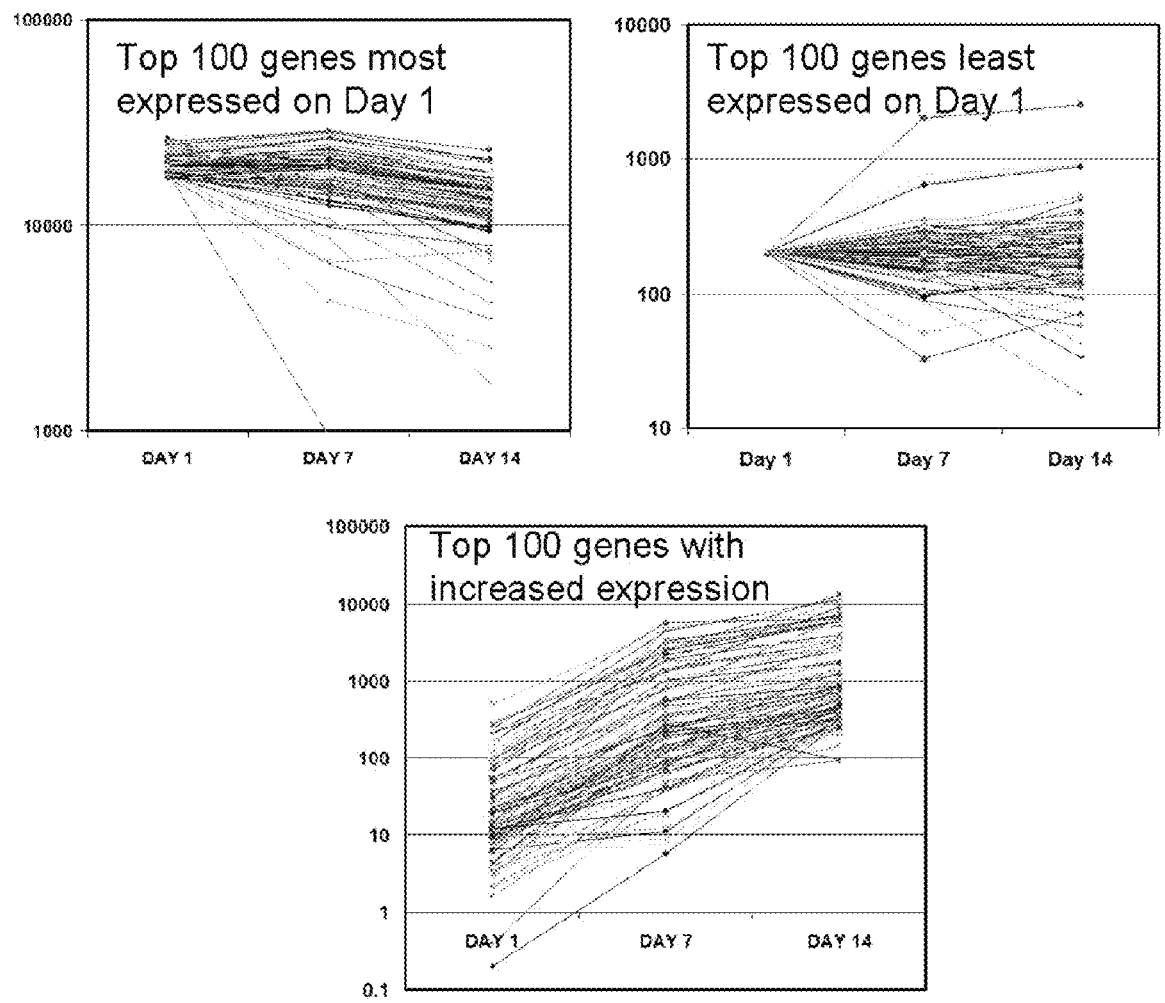
FIG. 57 shows graphs of gene expression profiles from cultured hepatocytes on crisscrossed fibrous scaffolds for time points of Day 1, Day 7, and Day 14.

Current efforts are devoted towards understanding the mechanisms of attachment, proliferation and differentiation of different cell lineages for regenerative medicinal applications. Specifically, the capacity of the fiber constructs to support hepatocyte cultures is being currently studied. Hepatocyte cultures in monolayers of three-dimensional structures have been well characterized and can be maintained as monolayers on flat surfaces, plastic or coated with biological polymers (collagen proteins etc.). Typically hepatocytes in these cultures lose their differentiation as judged by morphology and gene expression analyses. On the other hand, using STEP technique, it was recently demonstrated that hepatocytes attached on criss-crossed fibrous scaffolds arrange themselves into a monolayer in the absence of a complete flat substrate (FIGS. 55A-55B). These monolayers maintain morphologic stability for more than four weeks (FIGS. 56A-56B, data shown for two weeks), a time by which hepatocytes in typical monolayers lose morphologic and gene expression markers. Current efforts are devoted to evaluating gene expression patterns of these cultures compared to the standard ones by oligo-cDNA microarrays (Affymetrix platform, Block G D, et al. J. Cell Biol. 1996 March; 132(6): 1133-49). FIG. 57 shows graphs of gene expression profiles of the cell cultures, where expression is shown for 100 genes most expressed on Day 1, 100 genes least expressed on Day 1, and 100 genes with increased expression after two weeks. Tables 6-8 below provides a list of the genes shown in FIG. 57.

TABLE 6

List of 100 Genes most expressed on Day 1

NAME 1 alpha-2-macroglobulin
2 Transferrin
3 cytoplasmic beta-actin
4 hemopexin
5 beta-carotene 15,15-dioxygenase
6 haptoglobin
7 golgi SNAP receptor complex member 1
8 acidic ribosomal protein P0
9 glyceraldehyde-3-phosphate dehydrogenase
10 fibrinogen, gamma polypeptide
11 group-specific component (vitamin D-bindingprotein)
12 Cathepsin L
13 orosomucoid 1
14 tropomyosin 3, gamma
15 ribosomal protein S2
16 beta-2-microglobulin
17 Chemokine (C-C motif) ligand 9 (Ccl9)
18 ferritin subunit H
19 ribosomal protein S2
20 ferritin light chain
21 Ribosomal protein S29
22 Keratin 8 (Krt8)
23 serine protease inhibitor alpha 1
24 alpha 2 HS-glycoprotein alpha 2 (fetuin)
25 Putative ISG12(b) protein (isg12(b))
26 clusterin
27 ribosomal protein S6
28 albumin
29 eukaryotic translation elongation factor 1 alpha2
30 ribosomal protein S2
31 Ribosomal protein, large, P1 (Rplp1)
32 thymosin beta-4
33 Actin, gamma 1 (Actg1)
34 cytoplasmic beta-actin
35 Peptidylprolyl isomerase A (cyclophilin A)
36 ribosomal protein S17
37 Rattus norvegicus CDK110 mRNA
38 Ribosomal protein L3 (Rpl3)
39 Rat UDP-glucuronosyltransferase mRNA
40 NADH ubiquinone oxidoreductase subunit B13
41 Ribosomal protein L32 (Rpl32)
42 ribosomal protein L31
43 ribosomal protein S27a
44 Ribosomal protein L7a (Rpl7a)
45 Rat MHC class I RT1 (RT21) mRNA (u haplotype), 3 end.
46 Ribosomal protein S5
47 heat shock 70 kD protein 8
48 tumor protein, translationally-controlled 1
49 ribosomal protein S12
50 Rat apolipoprotein E gene
51 ribosomal protein L21
52 ral simian leukemia viral oncogene homolog A (ras related)
53 ribosomal protein S15a
54 ribosomal protein L10
55 ribosomal protein L10

TABLE 6-continued

List of 100 Genes most expressed on Day 1

NAME 56 ribosomal protein L5
57 Rat glutathione S-transferase mRNA
58 Rat glutathione S-transferase mRNA
59 Ribosomal protein S19 (Rps19)
60 ribosomal protein L19
61 UDP-glucuronosyltransferase 1A7
62 albumin
63 Fibronectin 1
64 ribosomal protein S24
65 ribosomal protein S14
66 ribosomal protein S8
67 ribosomal protein S27
68 apolipoprotein A-I
69 ribosomal protein S3a
70 metallothionein 1
71 phosphoglycerate mutase 1
72 transthyretin (prealbumin, amyloidosis type I)
73 ribosomal protein S21
74 complement component 3
75 Arginosuccinate synthetase 1
76 alpha-tubulin
77 double-stranded RNA-binding protein p74
78 ribosomal protein L27
79 Ribosomal protein L11 (Rpl11)
80 lactate dehydrogenase A
81 alpha-2u globulin
82 ribosomal protein L6
83 Rattus norvegicus cytokeratin-18 mRNA
84 ribosomal protein S26
85 Ribosomal protein L18A (Rpl18a)
86 Ribosomal protein L18A (Rpl18a)
87 Ribosomal protein S20 (Rps20)
88 Ribosomal protein S16 (Rps16)
89 serine protease inhibitor 2c
90 apolipoprotein C-III
91 ribosomal protein L24
92 elongation factor 1 alpha
93 R. norvegicus mRNA for ribosomal protein L41
94 enolase 1, alpha
95 polyubiquitin
96 Heat shock protein 90 kDa alpha (cytosolic), class B member 1 (Hsp90ab1)
97 polyubiquitin
98 alpha(1)-inhibitor 3, variant I
99 calcium binding protein
100 profilin

TABLE 7

List of 100 Genes least expressed on Day 1

NAME

1 Ras-related C3 botulinum toxin substrate 2
2 stearoyl-CoA desaturase 2
3 Family with sequence similarity 84, member B (Fam84b)
4 RGD1560010
5 Tnf receptor-associated factor 6 (Traf6)
6 Kelch-like 30 (Drosophila) (Klhl30)
7 Telomeric repeat binding factor (NIMA-interacting) 1 (Terf1)
8 Oxysterol binding protein (Osbp)
9 SH3 and cysteine rich domain 2 (Stac2)
10 Mitogen-activated protein kinase 8 interacting protein 3 (Mapk8ip3)
11 Smarcd1
12 Nicotinamide nucleotide adenylyltransferase 2 (Nmnat2)
13 Metal response element binding transcription factor 2 (Mtf2)
14 Zinc finger protein 668 (Znf668)
15 Insulin-like growth factor 2 mRNA binding protein 2 (Igf2bp2)
16 Utrophin (Utrn)
17 Prostaglandin E receptor 2, subtype EP2 (Ptger2)
18 Spock2
19 TCF3 (E2A) fusion partner (Tfpt)

TABLE 7-continued

List of 100 Genes least expressed on Day 1

NAME

20 Esterase 22 (Es22)
21 Kalirin, RhoGEF kinase (Kalrn)
22 Khdrbs3
23 Zinc finger protein 438 (Zfp438)
24 Glycosyltransferase 8 domain containing 3 (Glt8d3)
25 Retinoblastoma binding protein 6 (Rbbp6)
26 Opioid receptor, kappa 1 (Oprk1)
27 Aminoadipate-semialdehyde dehydrogenase (Aasdh)
28 Thioredoxin domain containing 16 (Txndc16)
29 Neuron navigator 2 (Nav2)
30 Kcnn2
31 E-STOP protein
32 Dishevelled associated activator of morphogenesis 1 (Daam1)
33 Protein tyrosine phosphatase, non-receptor type 14 (Ptpn14)
34 Phospholipase C, delta 1 (Plcd1)
35 Gnal
36 Glyceronephosphate O-acyltransferase (Gnpat)
37 vacuolar protein sorting protein 33a
38 Eukaryotic translation initiation factor 4E (Eif4e)
39 Plakophilin 2 (Pkp2)
40 Zinc finger protein 777 (Znf777)
41 Zinc finger protein 426 (Zfp426)
42 Polymerase (DNA directed), alpha 1 (Pola1)
43 CUG triplet repeat, RNA binding protein 2 (Cugbp2)
44 FH2 domain containing 1 (Fhdc1)
45 CD300A molecule (Cd300a)
46 Glycosyltransferase-like 1B (Gyltl1b)
47 Pleckstrin homology domain containing, family H (with MyTH4 domain) member 3 (Plekhh3)
48 Ankyrin repeat and IBR domain containing 1 (Ankib1)
49 RAS p21 protein activator 3 (Rasa3)
50 Proline rich 5 (renal) (Prr5)
51 Taste receptor, type 2, member 119 (Tas2r119)
52 Transmembrane protein 17 (Tmem17)
53 Coiled-coil domain containing 127 (Ccdc127)
54 Zinc finger protein 76 (expressed in testis) (Znf76)
55 RAB23, member RAS oncogene family (Rab23)
56 Organic solute carrier protein 1 (Oscp1)
57 Zinc finger protein 652 (Znf652)
58 Leucine rich repeat containing 26 (Lrrc26)
59 Matrix metallopeptidase 23 (Mmp23)
60 Zinc finger protein 426-like 2 (Zfp426l2)
61 fanconi anemia group C
62 nuclear pore complex protein
63 3-oxoacyl-ACP synthase, mitochondrial (Oxsm)
64 Ubiquitin-conjugating enzyme E2K (UBC1 homolog, yeast) (Ube2k)
65 UDP-GalNAc:polypeptideN-acet
66 Sortilin-related receptor, LDLR class A repeats-containing (Sorl1)
67 5'-nucleotidase domain containing 2 (Nt5dc2)
68 neurexophilin 1
69 WD repeat domain 51A (Wdr51a)
70 Solute carrier family 16, member 13 (monocarboxylic acid transporter 13) (Slc16a13)
71 Ankyrin repeat domain 54 (Ankrd54)
72 Chromobox homolog 8 (Pc class homolog, *Drosophila*) (Cbx8)
73 LOC361192
74 Nucleoporin like 1 (Nupl1)
75 Ankyrin repeat domain 11 (Ankrd11)
76 Prickle homolog 1 (*Drosophila*) (Prickle1)
77 Suppressor of fused homolog (*Drosophila*) (Sufu)
78 Neuropilin (NRP) and tolloid (TLL)-like 2 (Neto2)
79 MAD1 mitotic arrest deficient-like 1 (yeast) (Mad1l1)
80 Mitochondrial ribosomal protein L14 (Mrpl14)
81 Nucleolar protein 8 (Nol8)
82 Frizzled homolog 6 (*Drosophila*) (Fzd6)
83 MAP-kinase activating death domain (Madd)
84 5-hydroxytryptamine (serotonin) receptor 1B (Htr1b)
85 Ubiquitin-like modifier activating enzyme 7 (Uba7)
86 ArfGAP with RhoGAP domain, ankyrin repeat and PH domain 2 (Arap2)
87 Syncollin (Sycn)
88 Hemoglobin alpha, adult chain 2 (Hba-a2)
89 BMP-2 inducible kinase (Bmp2k)
90 Centromere protein I (Cenpi)

TABLE 7-continued

List of 100 Genes least expressed on Day 1

NAME

91 Defensin beta 22 (Defb22)
92 COMM domain containing 2 (Commd2)
93 Tropomyosin 1, alpha (Tpm1)
94 Matrix metallopeptidase 17 (Mmp17)
95 Frizzled homolog 5 (*Drosophila*) (Fzd5)
96 Insulin-like growth factor 2 mRNA binding protein 3 (Igf2bp3)
97 Yip1 domain family, member 7 (Yipf7)
98 EPM2A (laforin) interacting protein 1 (Epm2aip1)
99 Sarcoma antigen NY-SAR-48 (Ny-sar-48)
100 2-oxoglutarate and iron-dependent oxygenase domain containing 1 (Ogfod1)

TABLE 8

List of 100 Genes with highest expression after two weeks

NAME

1 Collagen, type XI, alpha 1 (Col11a1)
2 procollagen, type I, alpha 1
3 Keratin 7 (Krt7)
4 Keratin 19 (Krt19)
5 Cysteine-rich intestinal protein (Crip)
6 kidney-specific membrane protein
7 laminin chain beta 2
8 Cytochrome P450, subfamily XIB, polypeptide 2
9 Claudin 6 (Cldn6)
10 CXC chemokine LIX
11 Doublecortin domain containing 2 (Dcdc2)
12 Laminin, beta 1 (Lamb1)
13 secretin receptor
14 transforming growth factor,
15 Leprecan-like 2 (Leprel2)
16 Scavenger receptor class F, member 2 (Scarf2)
17 semaphorin 3 F (Sema3f)
18 procollagen, type I, alpha 2
19 secreted acidic cystein-rich glycoprotein(osteonectin)
20 AE binding protein 1 (Aebp1)
21 Forkhead box Q1 (Foxq1)
22 collagen, type V, alpha 1
23 Wingless-type MMTV integration site family, member 7A (Wnt7a)
24 chondroitin sulfate proteoglycan 2
25 Gap junction protein, alpha 1 (Gja1)
26 Trichorhinophalangeal syndrome I homolog (human) (Trps1)
27 Premature ovarian failure 1B (Pof1b)
28 Lysyl oxidase-like 1 (Loxl1)
29 FK506 binding protein 10 (Fkbp10)
30 Collagen, type XV, alpha 1 (Col15a1)
31 Septin 4 (Sept4)
32 procollagen, type I, alpha 2
33 Thymus cell surface antigen
34 aldehyde reductase 1
35 Cytokine receptor-like factor 1 (Crlf1)
36 small proteoglycan 1
37 Cadherin, EGF LAG seven-pass G-type receptor 1 (flamingo homolog, *Drosophila*) (Celsr1)
38 beta-galactoside-binding lectin
39 Plakophilin 1 (Pkp1)
40 Periostin, osteoblast specific factor (Postn)
41 Microtubule-associated protein 2
42 Protease, serine, 23 (Prss23)
43 angiopoietin-like 2
44 Collagen, type VI, alpha 2 (Col6a2)
45 Inhibin beta-B (Inhbb)
46 Prickle homolog 2 (*Drosophila*) (Prickle2)
47 Nucleosome assembly protein 1-like 5 (Nap1l5)
48 brain derived neurothrophic factor
49 fyn proto-oncogene
50 procollagen, type III, alpha 1
51 cyclin D2
52 Collagen triple helix repeat containing 1 (Cthrc1)

TABLE 8-continued

List of 100 Genes with highest expression after two weeks

NAME

53 Collagen, type XII, alpha 1 (Col12a1)
54 Adipocyte-specific adhesion molecule (Asam)
55 *Rattus norvegicus* Lfng mRNA for lunatic fringe, complete cds
56 dermo-1 protein
57 matrix metalloproteinase 11 (stromelysin 3)
58 EGF-containing fibulin-like extracellular matrix protein 2 (Efemp2)
59 Platelet derived growth factor receptor, beta polypeptide (Pdgfrb)
60 Similar to TPR repeat-containing protein KIAA1043 (LOC304558)
61 Grainyhead-like 3 (*Drosophila*) (Grhl3)
62 neuroblast
63 Cysteine-rich secretory protein LCCL domain containing 2 (Crispld2)
64 s-gicerinMUC18
65 Lysyl oxidase-like 3 (Loxl3)
66 non-processed neurexin I-beta
67 Family with sequence similarity 101, member B (Fam101b)
68 G protein-coupled receptor 126 (Gpr126)
69 wingless-type MMTV integration site family, member 4
70 Cytohesin 3 (Cyth3)
71 Peroxidasin homolog (*Drosophila*) (Pxdn)
72 late gestation lung protein 1
73 Lipoma HMGIC fusion partner (Lhfp)
74 Tissue factor pathway inhibitor 2 (Tfpi2)
75 protein tyrosine phosphatase epsilon C
76 drebrin 1
77 Rat beta-type calcitonin gene-related peptide mRNA, complete cds
78 Transforming growth factor, beta 2 (Tgfb2)
79 endothelial and smooth muscle cell
80 Kv1.6 voltage-gated potassium chann
81 CD24 antigen
82 Chloride intracellular channel 3 (Clic3)
83 Collagen, type IV, alpha 1 (Col4a1)
84 Bone morphogenetic protein 6
85 Transmembrane 4 L six family member 20 (Tm4sf20)
86 crp-ductin
87 Rhombex-29
88 membrane-associated protein 17
89 Collagen alpha 1
90 follistatin-related protein precursor
91 glypican 3
92 fibroblast growth factor receptor 1 beta-isoform
93 MAP2d
94 acyl-CoA thioesterase 1, cytosolic
95 Peroxidasin homolog (*Drosophila*) (Pxdn)
96 Similar to RIKEN cDNA 4931406C07 (RGD1309534)
97 Cortactin binding protein 2 (Cttnbp2)
98 Collagen, type IV, alpha 1 (Col4a1)
99 Collagen, type VIII, alpha 1 (Col8a1)
100 Fibroblast growth factor receptor 3 (Fgfr3)

Example 11

Growth of Neural Stem Cells on a Biological Matrix

Materials and Methods:

PS fibers were coated overnight at room temperature with a 10 μg/ml aqueous poly-L-ornithine (Sigma) solution. The solution was then aspirated away, the fibrous substrate washed 2× with DI water, and then incubated at 37° C. for 12 hours in a 5 μg/ml aqueous laminin (Sigma) solution. This solution was then aspirated away, the substrate washed 2× with PBS, and then seeded with adult rat neural stem cells (Chemicon) in Neurobasal media with B27 supplement (Chemicon), with and without 1% fetal bovine serum (Invitrogen) at varying cell densities (10-100×10$^3$ cells/ml). Cells were allowed to adhere and differentiate in media at 37 C in a sterile CO2 incubator for 3-7 days and were then immunofluorescently stained to reveal markers of neural cellular lineage (Nestin for NSC, MAP2 for neurons, GFAP for astrocytes, and RIP for oligodendrocytes each from abcam, with secondary antibodies from Jackson), fluorescently stained to show cytoskeleton structure (Alexa 488-phalloidin for F-actin, from Invitrogen) and stained with DAPI and calceinAM (Invitrogen) to show nuclear and cytoplasmic character of the differentiating cells. Cells were then imaged on a laser scanning confocal fluorescence microscope (Leica TCS SP5) and cellular staining yields quantified using Adobe Photoshop CS2.

Figure 58:
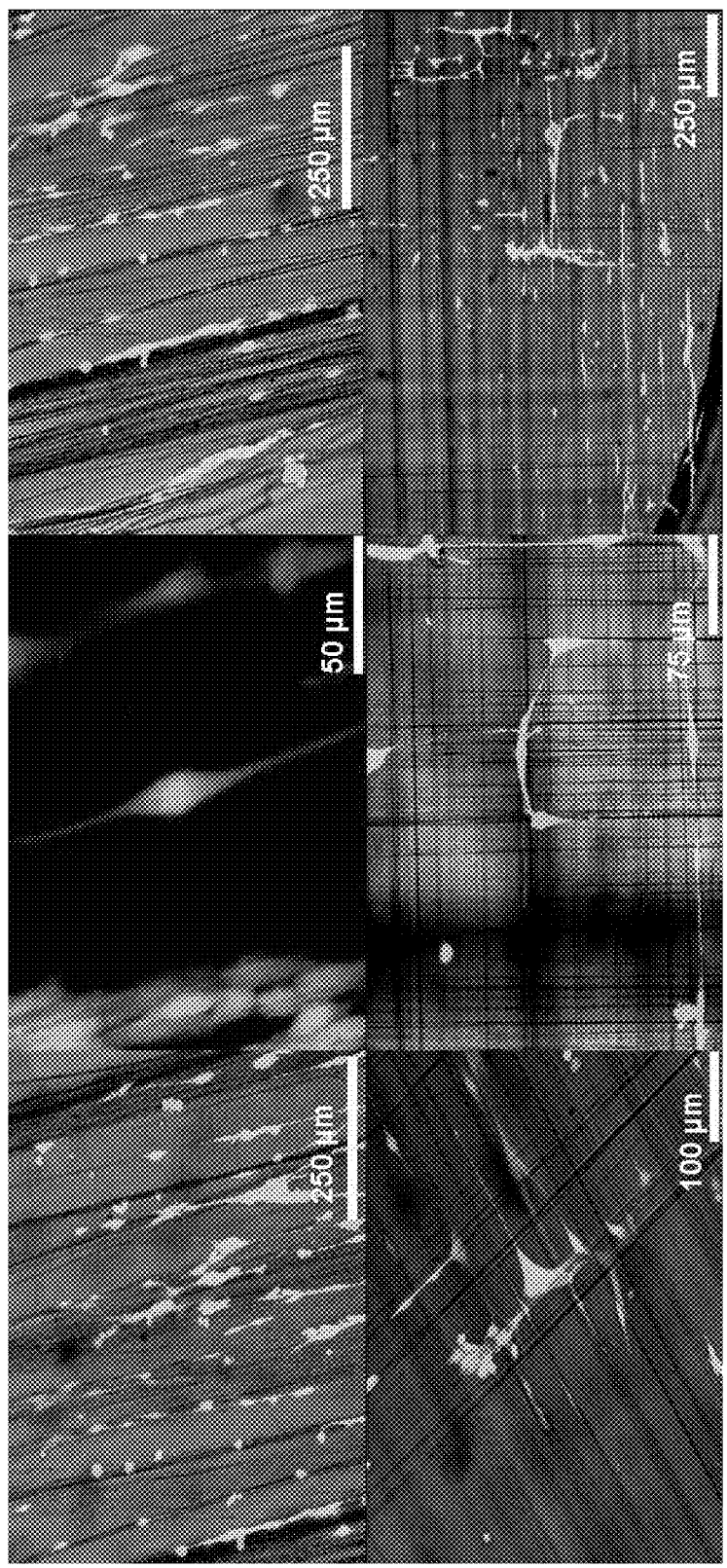
FIG. 58 are photomicrographs of rat neural stem cells seeded on single layer (top row) and crisscrossed (bottom row) scaffolds showing preferential alignment along fiber axis
Figure 59:
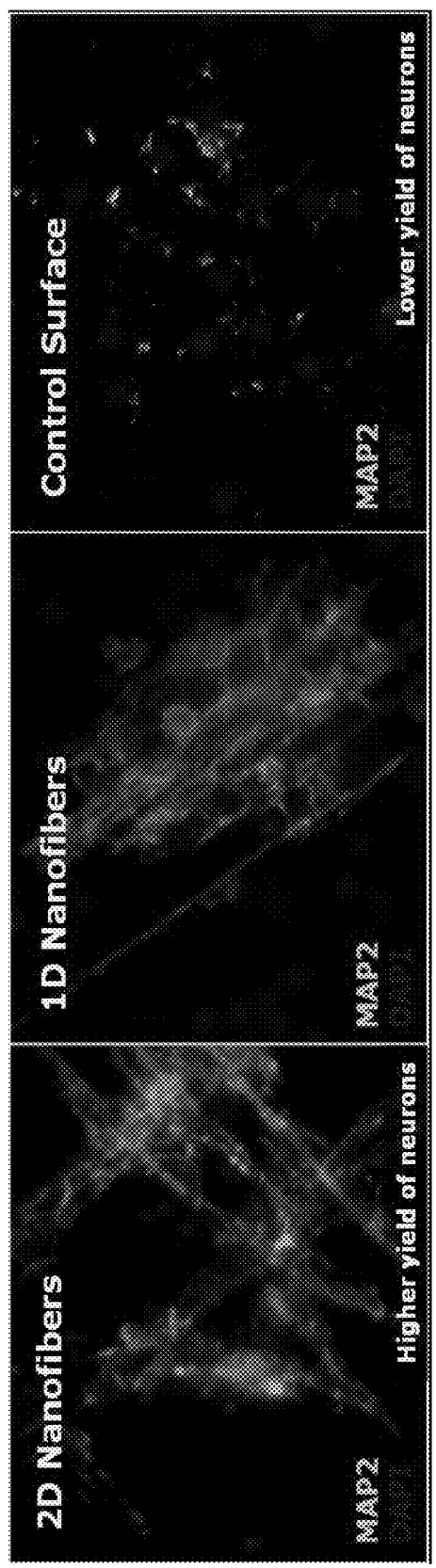
FIG. 59 shows fluorescence photomicrographs of neurons, where higher yield of neurons are obtained on crisscrossed scaffolds (labeled "2D Nanofibers) and single layer scaffolds (labeled "1D Nanofibers") compared to a flat substrate (labeled "Control Surface").

The cellular mechanical microenvironment has previously been shown to influence adult stem cell fate (A. J. Engler, S. Sen, H. L. Sweeney, D. E. Discher, Cell 126, 677 (Aug. 25, 2006)). To investigate the influence of nano-scale geometry on adult neural stem cell (NSC) differentiation and migration, a newly developed fabrication technique, "Spinneret-based Tunable Engineering Parameters" (STEP), was employed (A. S. Nain et al., Small 4, 1153 (August, 2008)). This technique enables precisely aligned single- and multi-layered nanofiber scaffolds with nano-scale control of fiber diameter and microscale control over fiber spacing. In particular, multiple highly aligned, poly-L-ornithine/laminin-coated polystyrene nanofiber and planar scaffolds were fabricated to probe NSC differentiation and migration. NSCs cultured on these substrates attach within 2 hours of seeding, extending membrane processes parallel to the direction of fiber alignment, assuming a polar morphology with microtubules aligning preferentially in the direction of fiber alignment, unlike on planar controls, within hours as shown in FIG. 58. Additionally, attached cells migrate almost exclusively in the direction of nanofiber alignment over at least 3 days, by time-lapse confocal microscopy. On these aligned substrates, in common media, degree of neuronal differentiation was greatly enhanced, by immunofluorescence staining; particularly, on approx. 800 nm dia. aligned, suspended nanofibers, NSCs differentiated with >80% of cells staining MAP2+ (neuronal marker), as compared to <15% staining positive on planar controls as shown in FIG. 59.

Whereas particular embodiments of this invention have been described above for purposes of illustration, it will be evident to those skilled in the art that numerous variations of the details of the present invention may be made without departing from the invention as defined in the appended claims.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values.

I claim:

1. A method of preparing a bead-free, high aspect ratio polymeric fiber comprising:
   determining an entanglement concentration ($C_e$) for a first polymer solution comprising a first polymer and a first good solvent for the first polymer;
   feeding the first polymer solution comprising the first polymer having a concentration of at least $C_e$ in the first good solvent for the first polymer through a spinneret to produce an extruded droplet of polymer solution at a tip of the spinneret;
   contacting the extruded droplet of polymer solution with a target at a contact point;

moving the contact point away from the spinneret, thereby pulling a high aspect ratio polymeric fiber from the extruded droplet of polymer solution at the tip of the spinneret; and further pulling the fiber from the extruded droplet of polymer solution at the tip of the spinneret and feeding the first polymer solution through the spinneret into the extruded droplet of polymer solution at the tip of the spinneret at a rate sufficient to compensate for an amount of the first polymer solution used to produce the fiber, thereby producing a bead-free, high aspect ratio polymeric fiber.

2. The method of claim 1 comprising determining a velocity to pull the fiber in order to obtain a desired fiber diameter and pulling the fiber at that velocity.

3. The method of claim 1, wherein the contact point is on a rotatable form and after the distance between the extruded droplet of polymer solution at the tip of the spinneret and the contact point is increased, the form is rotated to further pull the fiber and to wrap the fiber about the form.

4. The method of claim 3, in which, while the form is rotated, it is moved in a direction having a vector parallel to an axis of rotation of the form while the fiber is deposited to space apart each wrap of the fiber about the form.

5. The method of claim 3, in which, while the axis of rotation of the form is rotated in relation to the fiber to change the angle of deposition of the fiber on the form.

6. The method of claim 3, further comprising wrapping about the form a fiber of a second polymer from a second polymer solution that is either the same or different from the first polymer solution comprising a second polymer and a second good solvent for the second polymer from a second source, wherein the second polymer is at a concentration in the second polymer solution of at least $C_e$ for the second polymer solution.

7. The method of claim 6, in which the second polymer is wrapped about the form at the same time the first polymer is wrapped about the form.

8. The method of claim 3, in which the form is a frame comprising one or more perimeter elements defining an opening.

9. The method of claim 8, in which the frame comprises two substantially parallel perimeter elements and one or more perimeter elements connecting the two substantially parallel perimeter elements, the perimeter elements defining an opening, and the fiber is wrapped substantially perpendicularly to the two substantially parallel perimeter elements.

10. The method of claim 8, further comprising assembling the frame having the fiber wrapped about the frame into an assembly comprising a plurality of the frames.

11. The method of claim 8, further comprising assembling the frame having the fiber wrapped about the frame into a filtration assembly.

12. The method of claim 3, wherein one or more of the spinneret and the target are attached to a positionable stage.

13. The method of claim 12, wherein the positionable stage is movable in three-dimensions.

14. The method of claim 12, wherein movement of the one or more positionable stages is controlled by a computer.

15. The method of claim 12, in which the target is attached to an axle of a motor.

16. The method of claim 15, in which the motor is attached to a positionable stage.

17. The method of claim 3, in which the form is a solid structure having substantially no openings.

18. The method of claim 1, wherein the polymer is one or more of a polystyrene, a polyester, a polyurethane, a polyacrylamide, a poly(methyl methacrylate), a polylactic acid, a poly(lactic-co-glycolic acid), fibrinogen and mixtures and copolymers thereof.

19. The method of claim 1, wherein the polymer is a polystyrene.

20. The method of claim 1, further comprising after pulling the fiber from the polymer solution, depositing a particle onto the fiber.

21. The method of claim 20, wherein the particle is an activated carbon particle.

22. The method of claim 3, comprising forming a nonwoven mesh of fibers about the form.

23. The method of claim 1, further comprising depositing collagen onto the fibers.

24. The method of claim 1, further comprising placing the fiber onto a surface of a cell culture vessel.

25. The method of claim 1, further comprising depositing onto the form or fibers on the form, a second polymer that is the same or different from the first polymer in a solvent, in a second polymer solution in which the concentration of the polymer is below the $C_e$ for the second polymer in the solvent, thereby depositing a beaded structure onto the form or fibers on the form.

26. The method of claim 1, wherein a diameter of the high aspect ratio fiber is determined according to an equation that provides a scaling law that plots the diameter of the fiber as a function of normalized concentration.

27. The method of claim 1, comprising depositing cells onto the fiber.

28. The method of claim 27, comprising depositing collagen onto the fiber and depositing cells onto the fiber and culturing the cells in a suitable cell growth medium.

29. The method of claim 27, wherein the cells are totipotent, pluripotent or multipotent.

30. The method of claim 29, wherein the cells are muscle precursor cells.

31. The method of claim 29, wherein the cells are neural precursor cells.

32. The method of claim 29, wherein the cells are hepatocytes.

33. The method of claim 27, in which a plurality of fibers are formed into one or more bundles of substantially parallel fibers of the first polymer.

34. The method of claim 27, wherein the fiber is deposited onto the form in a first layer comprising the first polymer and a second layer in which fibers of the second layer cross fibers of the first layer, the second layer comprising a polymer that is the same or different from the first polymer.

35. The method of claim 1, further comprising:
depositing the fiber onto a substrate such that the fiber has fixed boundaries; and
breaking the fiber by striking the fiber with a probe.

36. The method of claim 35, in which the probe is an atomic force microscope using one of an atomic force microscope probe and a microprobe mounted to a stage.

37. The method of claim 35, in which the fiber is broken by lateral movement of the atomic force microscope probe or microprobe.

38. The method of claim 1, further comprising:
determining for a solvent and polymer combination a relationship between molecular weight and polymer concentration for the solvent and polymer combination for a diameter of fibers pulled from the solvent and polymer combination to determine a polymer concentration of the polymer in the solvent for preparing a polymer fiber of the diameter.

39. The method of claim 27, comprising orienting a plurality of the fibers in a geometrical configuration to direct migration of the cells.

40. The method of claim 39, in which a plurality of fibers are oriented in a substantially parallel configuration to direct cell growth along the fibers.

41. The method of claim 40, in which one or more fibers cross the plurality of fibers.

42. The method of claim 39, in which fibers are crossed to inhibit cell migration along the fibers.

43. The method of claim 39, in which polymer beads are contacted with the one or more fibers to inhibit cell migration along the fibers.

44. The method of claim 6, in which the second polymer is wrapped about the form after the first polymer is wrapped about the form.

45. The method of claim 1, further comprising depositing activated carbon particles onto the fiber.

* * * * *